(12) United States Patent
Feldmann et al.

(10) Patent No.: US 7,663,027 B2
(45) Date of Patent: Feb. 16, 2010

US007663027B2

(54) NUCLEOTIDE SEQUENCES AND CORRESPONDING POLYPEPTIDES CONFERRING MODULATED PLANT SIZE AND BIOMASS IN PLANTS

(75) Inventors: Kenneth Feldmann, Newbury Park, CA (US); Greg Nadzan, Woodland Hills, CA (US)

(73) Assignee: Ceres, Inc., Thousand Oaks, CA (US)

( * ) Notice: Subject to any disclaimer, the term of this patent is extended or adjusted under 35 U.S.C. 154(b) by 312 days.

(21) Appl. No.: 11/298,391

(22) Filed: Dec. 8, 2005

(65) Prior Publication Data

US 2006/0195943 A1    Aug. 31, 2006

Related U.S. Application Data

(60) Provisional application No. 60/635,115, filed on Dec. 8, 2004, provisional application No. 60/635,140, filed on Dec. 8, 2004.

(51) Int. Cl.
*C12N 15/82* (2006.01)
*C12N 5/04* (2006.01)
*A01H 5/00* (2006.01)
*A01H 5/10* (2006.01)

(52) U.S. Cl. ............... 800/298; 800/278; 800/290; 800/287; 435/419; 435/531

(58) Field of Classification Search ............ None
See application file for complete search history.

(56) References Cited

U.S. PATENT DOCUMENTS

2003/0150026 A1    8/2003    Chory et al.

FOREIGN PATENT DOCUMENTS

EP        1033405 A2         6/2000
WO    WO2005/019462 A1    3/2005
WO    WO2006/004955 A2    1/2006

OTHER PUBLICATIONS

Bowie et al, Science 247:1306-1310, 1990.*
McConnell et al, Nature 411 (6838):709-713, 2001.*
Oommenn et al (1994, The Plant Cell 6:1789-1803).*
Database EMBL [Online ] Jun. 14, 2002, "*Arabidopsis thaliana* clone 8161 mRNA, complete sequence." XP002389274, retrieved from EBI accession No. EM_PRO:AY088585, Database accession No. AY088585 abstract.
Database Geneseq [Online] Oct. 17, 2000, "*Arabidopsis thaliana* DNA fragment SEQ ID No. 540." XP002389275, retrieved from EBI accession No. GSN:AAC32758, Database accession No. AAC32758 abstract.
Database Geneseq [Online] Jan. 15, 2004, "Plant yield-related polynucleotide clone G12929." XP002389276, retrieved from EBI accession No. GSN:ADD30385, Database accession No. ADD30385 abstract.
Database EMBL [Online] Jun. 14, 2002, "*Arabidopsis thaliana* clone 37288 mRNA, complete sequence." XP002389277, retrieved from EBI accession No. EM_PRO:AY087639, database accession No. AY087639 abstract.
Database Geneseq [Online] Oct. 18, 2000, "*Arabidopsis thaliana* DNA fragment SEQ ID No. 71356," XP002389278 retreived from EBI accession No. GSN:AAC52442, Database accession No. AAC52442 abstract.
XP-002389274, EMBL-EBI, European Bioinformatics Institute, Nucleotide Sequences Browsing Jun. 7, 2006.
XP-002389277, EMBL-EBI, European Bioinformatics Institute, Nucleotide Sequences Browsing Jul. 7, 2006, pp. 1-6.

* cited by examiner

*Primary Examiner*—Stuart F. Baum
(74) *Attorney, Agent, or Firm*—Birch, Stewart, Kolasch & Birch, LLP

(57) ABSTRACT

The present invention relates to isolated nucleic acid molecules and their corresponding encoded polypeptides able confer the trait of modulated plant size, vegetative growth, organ number, plant architecture and/or biomass in plants. The present invention further relates to the use of these nucleic acid molecules and polypeptides in making transgenic plants, plant cells, plant materials or seeds of a plant having plant size, vegetative growth, organ number, plant architecture and/or biomass that are altered with respect to wild type plants grown under similar conditions.

21 Claims, No Drawings

NUCLEOTIDE SEQUENCES AND CORRESPONDING POLYPEPTIDES CONFERRING MODULATED PLANT SIZE AND BIOMASS IN PLANTS

This non-provisional application claims priority under 35 U.S.C. §119(e) on U.S. Provisional Application Nos. 60/635,115 and 60/635,140 filed on Dec. 8, 2005, the entire contents of which are hereby incorporated by reference.

FIELD OF THE INVENTION

The present invention relates to isolated nucleic acid molecules and their corresponding encoded polypeptides able to modulate plant size, vegetative growth, organ number, architecture and/or biomass in plants. The present invention further relates to using the nucleic acid molecules and polypeptides to make transgenic plants, plant cells, plant materials or seeds of a plant having modulated size, vegetative growth, organ number, architecture and/or biomass as compared to wild-type plants grown under similar conditions.

BACKGROUND OF THE INVENTION

Plants specifically improved for agriculture, horticulture, biomass conversion, and other industries (e.g. paper industry, plants as production factories for proteins or other compounds) can be obtained using molecular technologies. As an example, great agronomic value can result from modulating the size of a plant as a whole or of any of its organs or the number of any of its organs.

Similarly, modulation of the size and stature of an entire plant, or a particular portion of a plant, allows production of plants better suited for a particular industry. For example, reductions in the height of specific crops and tree species can be beneficial by allowing easier harvesting. Alternatively, increasing height, thickness or organ number may be beneficial by providing more biomass useful for processing into food, feed, fuels and/or chemicals (http://www.eere.energy.gov/biomass/publications.html). Other examples of commercially desirable traits include increasing the length of the floral stems of cut flowers, increasing or altering leaf size and shape or enhancing the size of seeds and/or fruits. Changes in organ size, organ number and biomass also result in changes in the mass of constituent molecules such as secondary products and convert the plants into factories for these compounds.

Availability and maintenance of a reproducible stream of food and feed to feed people has been a high priority throughout the history of human civilization and lies at the origin of agriculture. Specialists and researchers in the fields of agronomy science, agriculture, crop science, horticulture, and forest science are even today constantly striving to find and produce plants with an increased growth potential to feed an increasing world population and to guarantee a supply of reproducible raw materials. The robust level of research in these fields of science indicates the level of importance leaders in every geographic environment and climate around the world place on providing sustainable sources of food, feed and energy for the population.

Manipulation of crop performance has been accomplished conventionally for centuries through plant breeding. The breeding process is, however, both time-consuming and labor-intensive. Furthermore, appropriate breeding programs must be specially designed for each relevant plant species.

On the other hand, great progress has been made in using molecular genetics approaches to manipulate plants to provide better crops. Through introduction and expression of recombinant nucleic acid molecules in plants, researchers are now poised to provide the community with plant species tailored to grow more efficiently and produce more product despite unique geographic and/or climatic environments. These new approaches have the additional advantage of not being limited to one plant species, but instead being applicable to multiple different plant species (1).

Despite this progress, today there continues to be a great need for generally applicable processes that improve forest or agricultural plant growth to suit particular needs depending on specific environmental conditions. To this end, the present invention is directed to advantageously manipulating plant size, organ number, plant architecture and/or biomass to maximize the benefits of various crops depending on the benefit sought and the particular environment in which the crop must grow, characterized by expression of recombinant DNA molecules in plants. These molecules may be from the plant itself, and simply expressed at a higher or lower level, or the molecules may be from different plant species.

SUMMARY OF THE INVENTION

The present invention, therefore, relates to isolated nucleic acid molecules and polypeptides and their use in making transgenic plants, plant cells, plant materials or seeds of plants having life cycles, particularly plant size, vegetative growth, organ number, plant architecture and/or biomass, that are altered with respect to wild-type plants grown under similar or identical conditions.

Unless otherwise defined, all technical and scientific terms used herein have the same meaning as commonly understood by one of ordinary skill in the art to which this invention belongs.

DETAILED DESCRIPTION OF THE INVENTION

1. The Invention

The invention of the present application may be described by, but not necessarily limited to, the following exemplary embodiments.

The present invention discloses novel isolated nucleic acid molecules, nucleic acid molecules that interfere with these nucleic acid molecules, nucleic acid molecules that hybridize to these nucleic acid molecules, and isolated nucleic acid molecules that encode the same protein due to the degeneracy of the DNA code. Additional embodiments of the present application further include the polypeptides encoded by the isolated nucleic acid molecules of the present invention.

More particularly, the nucleic acid molecules of the present invention comprise: (a) a nucleotide sequence encoding an amino acid sequence that is at least 85% identical to any one of Leads 11, 17, 50, 58, 13/64 and 12/67, corresponding to SEQ ID Nos. 2, 10, 17, 22, 27 and 4, respectively, (b) a nucleotide sequence that is complementary to any one of the nucleotide sequences according to (a), (c) a nucleotide sequence according to any one of SEQ ID Nos. 1, 9, 16, 21, 26 and 3, (d) a nucleotide sequence that is in reverse order of any one of the nucleotide sequences according to (c) when read in the 5' to 3' direction, (e) a nucleotide sequence able to interfere with any one of the nucleotide sequences according to (a), (f) a nucleotide sequence able to form a hybridized nucleic acid duplex with the nucleic acid according to any one of paragraphs (a)-(e) at a temperature from about 40° C. to about 48° C. below a melting temperature of the hybridized nucleic acid duplex, and (g) a nucleotide sequence encoding any one of amino acid sequences of Leads 11, 17, 50, 58, 13/64 and 12/67, corresponding to SEQ ID Nos. 2, 10, 17, 22, 27 and 4, respectively.

Additional embodiments of the present invention include those polypeptide and nucleic acid molecule sequences disclosed in SEQ ID NOS: 1-30.

The present invention further embodies a vector comprising a first nucleic acid having a nucleotide sequence encoding a plant transcription and/or translation signal, and a second nucleic acid having a nucleotide sequence according to the isolated nucleic acid molecules of the present invention. More particularly, the first and second nucleic acids may be operably linked. Even more particularly, the second nucleic acid may be endogenous to a first organism, and any other nucleic acid in the vector may be endogenous to a second organism. Most particularly, the first and second organisms may be different species.

In a further embodiment of the present invention, a host cell may comprise an isolated nucleic acid molecule according to the present invention. More particularly, the isolated nucleic acid molecule of the present invention found in the host cell of the present invention may be endogenous to a first organism and may be flanked by nucleotide sequences endogenous to a second organism. Further, the first and second organisms may be different species. Even more particularly, the host cell of the present invention may comprise a vector according to the present invention, which itself comprises nucleic acid molecules according to those of the present invention.

In another embodiment of the present invention, the isolated polypeptides of the present invention may additionally comprise amino acid sequences that are at least 85% identical to any one of Leads 11, 17, 50, 58, 13/64 and 12/67, corresponding to SEQ ID Nos. 2, 10, 17, 22, 27 and 4, respectively.

Other embodiments of the present invention include methods of introducing an isolated nucleic acid of the present invention into a host cell. More particularly, an isolated nucleic acid molecule of the present invention may be contacted to a host cell under conditions allowing transport of the isolated nucleic acid into the host cell. Even more particularly, a vector as described in a previous embodiment of the present invention, may be introduced into a host cell by the same method.

Methods of detection are also available as embodiments of the present invention. Particularly, methods for detecting a nucleic acid molecule according to the present invention in a sample. More particularly, the isolated nucleic acid molecule according to the present invention may be contacted with a sample under conditions that permit a comparison of the nucleotide sequence of the isolated nucleic acid molecule with a nucleotide sequence of nucleic acid in the sample. The results of such an analysis may then be considered to determine whether the isolated nucleic acid molecule of the present invention is detectable and therefore present within the sample.

A further embodiment of the present invention comprises a plant, plant cell, plant material or seeds of plants comprising an isolated nucleic acid molecule and/or vector of the present invention. More particularly, the isolated nucleic acid molecule of the present invention may be exogenous to the plant, plant cell, plant material or seed of a plant.

A further embodiment of the present invention includes a plant regenerated from a plant cell or seed according to the present invention. More particularly, the plant, or plants derived from the plant, plant cell, plant material or seeds of a plant of the present invention preferably has increased size (in whole or in part), increased vegetative growth, increased organ number and/or increased biomass (sometimes hereinafter collectively referred to as increased biomass) as compared to a wild-type plant cultivated under identical conditions. Furthermore, the transgenic plant may comprise a first isolated nucleic acid molecule of the present invention, which encodes a protein involved in early flowering, and a second isolated nucleic acid molecule which encodes a promoter capable of driving expression in plants, wherein the increased biomass component and the promoter are operably linked. More preferably, the gene conferring increased biomass may be mis-expressed in the transgenic plant of the present invention, and the transgenic plant exhibits an increased biomass as compared to a progenitor plant devoid of the gene, when the transgenic plant and the progenitor plant are cultivated under identical environmental conditions. In another embodiment of the present invention increased biomass phenotype may be due to the inactivation of a particular sequence, using for example an interfering RNA.

A preferred embodiment consists of a plant, plant cell, plant material or seed of a plant according to the present invention which comprises an isolated nucleic acid molecule of the present invention, wherein the plant, or plants derived from the plant, plant cell, plant material or seed of a plant, has increased biomass as compared to a wild-type plant cultivated under identical conditions.

Another embodiment of the present invention includes methods of enhancing biomass in plants. More particularly, these methods comprise transforming a plant with an isolated nucleic acid molecule according to the present invention. Preferably, the method is a method of enhancing biomass in the transformed plant, whereby the plant is transformed with a nucleic acid molecule encoding the polypeptide of the present invention.

2. Definitions

The following terms are utilized throughout this application:

Biomass: As used herein, "biomass" refers to useful biological material including a product of interest, which material is to be collected and is intended for further processing to isolate or concentrate the product of interest. "Biomass" may comprise the fruit or parts of it or seeds, leaves, or stems or roots where these are the parts of the plant that are of particular interest for the industrial purpose. "Biomass", as it refers to plant material, includes any structure or structures of a plant that contain or represent the product of interest.

Transformation: Examples of means by which this can be accomplished are described below and include *Agrobacterium*-mediated transformation (of dicots (9-10), of monocots (11-13), and biolistic methods (14)), electroporation, in planta techniques, and the like. Such a plant containing the exogenous nucleic acid is referred to here as a $T_0$ for the primary transgenic plant and $T_1$ for the first generation.

Functionally Comparable Proteins or Functional Homologs: This term describes those proteins that have at least one functional characteristic in common. Such characteristics include sequence similarity, biochemical activity, transcriptional pattern similarity and phenotypic activity. Typically, the functionally comparable proteins share some sequence similarity or at least one biochemical. Within this definition, analogs are considered to be functionally comparable. In addition, functionally comparable proteins generally share at least one biochemical and/or phenotypic activity.

Functionally comparable proteins will give rise to the same characteristic to a similar, but not necessarily the same, degree. Typically, comparable proteins give the same characteristics where the quantitative measurement due to one of the comparables is at least 20% of the other; more typically, between 30 to 40%; even more typically, between 50-60%; even more typically between 70 to 80%; even more typically between 90 to 100% of the other.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Misexpression: The term "misexpression" refers to an increase or a decrease in the transcription of a coding region into a complementary RNA sequence as compared to the wild-type. This term also encompasses expression and/or translation of a gene or coding region or inhibition of such transcription and/or translation for a different time period as compared to the wild-type and/or from a non-natural location within the plant genome.

Percentage of sequence identity: As used herein, the term "percent sequence identity" refers to the degree of identity between any given query sequence and a subject sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment).

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

In case of the functional homolog searches, to ensure a subject sequence having the same function as the query sequence, the alignment has to be along at least 80% of the length of the query sequence so that the majority of the query sequence is covered by the subject sequence. To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Regulatory Regions: The term "regulatory region" refers to nucleotide sequences that, when operably linked to a sequence, influence transcription initiation or translation initiation or transcription termination of said sequence and the rate of said processes, and/or stability and/or mobility of a transcription or translation product. As used herein, the term "operably linked" refers to positioning of a regulatory region and said sequence to enable said influence. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Regulatory regions can be classified in two categories, promoters and other regulatory regions.

Stringency: "Stringency," as used herein is a function of nucleic acid molecule probe length, nucleic acid molecule probe composition (G+C content), salt concentration, organic solvent concentration and temperature of hybridization and/or wash conditions. Stringency is typically measured by the parameter $T_m$, which is the temperature at which 50% of the complementary nucleic acid molecules in the hybridization assay are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship between hybridization conditions and $T_m$ (in ° C.) is expressed in the mathematical equation:

$$T_m = 81.5 - 16.6(\log_{10}[\text{Na}^+]) + 0.41(\% \ G+C) - (600/N) \quad (I)$$

where N is the number of nucleotides of the nucleic acid molecule probe. This equation works well for probes 14 to 70 nucleotides in length that are identical to the target sequence. The equation below, for $T_m$ of DNA-DNA hybrids, is useful for probes having lengths in the range of 50 to greater than 500 nucleotides, and for conditions that include an organic solvent (formamide):

$$T_m = 81.5 + 16.6 \log \{[\text{Na}^+]/(1+0.7[\text{Na}^+])\} + 0.41(\% \ G+C) - 500/L \ 0.63(\% \ \text{formamide}) \quad (II)$$

where L represents the number of nucleotides in the probe in the hybrid (21). The $T_m$ of Equation II is affected by the nature of the hybrid: for DNA-RNA hybrids, $T_m$ is 10-15° C. higher than calculated; for RNA-RNA hybrids, $T_m$ is 20-25° C. higher. Because the $T_m$ decreases about 1° C. for each 1% decrease in homology when a long probe is used (22), stringency conditions can be adjusted to favor detection of identical genes or related family members.

Equation II is derived assuming the reaction is at equilibrium. Therefore, hybridizations according to the present invention are most preferably performed under conditions of probe excess and allowing sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction, or after hybridization has occurred, by altering the salt and temperature conditions of the wash solutions. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

$T_0$: The term "$T_0$" refers to the whole plant, explant or callus tissue, inoculated with the transformation medium.

$T_1$: The term $T_1$ refers to either the progeny of the $T_0$ plant, in the case of whole-plant transformation, or the regenerated seedling in the case of explant or callous tissue transformation.

$T_2$: The term $T_2$ refers to the progeny of the $T_1$ plant. $T_2$ progeny are the result of self-fertilization or cross-pollination of a $T_1$ plant.

$T_3$: The term $T_3$ refers to second generation progeny of the plant that is the direct result of a transformation experiment. $T_3$ progeny are the result of self-fertilization or cross-pollination of a $T_2$ plant.

3. Important Characteristics of the Polynuceotides and Polypeptides of the Invention The nucleic acid molecules and polypeptides of the present invention are of interest because when the nucleic acid molecules are mis-expressed (ie., when expressed at a non-natural location or in an increased or decreased amount relative to wild-type) they produce plants that exhibit modulated biomass as compared to wild-type plants, as evidenced by the results of various experiments disclosed below. This trait can be used to exploit or maximize plant products. For example, the nucleic acid molecules and polypeptides of the present invention are used to increase the expression of genes that cause the plant to have modulated biomass.

Because the disclosed sequences and methods increase vegetative growth, the disclosed methods can be used to enhance biomass production. For example, plants that grow vegetatively have an increase biomass production, compared to a plant of the same species that is not genetically modified for substantial vegetative growth. Examples of increases in biomass production include increases of at least 10%, at least 20%, or even at least 50%, when compared to an amount of biomass production by a plant of the same species not growing vegetatively.

The life cycle of flowering plants in general can be divided into three growth phases: vegetative, inflorescence, and floral (late inflorescence phase). In the vegetative phase, the shoot apical meristem (SAM) generates leaves that later will ensure the resources necessary to produce fertile offspring. Upon receiving the appropriate environmental and developmental signals the plant switches to floral, or reproductive, growth and the SAM enters the inflorescence phase (I) and gives rise to an inflorescence with flower primordia. During this phase the fate of the SAM and the secondary shoots that arise in the axils of the leaves is determined by a set of meristem identity genes, some of which prevent and some of which promote the development of floral meristems. Once established, the plant enters the late inflorescence phase (12) where the floral organs are produced. If the appropriate environmental and developmental signals the plant switches to floral, or reproductive, growth are disrupted, the plant will not be able to enter reproductive growth, therefore maintaining vegetative growth.

4. The Genes of the Invention

The polynucleotides of the present invention and the proteins expressed via translation of these polynucleotides are set forth in the Sequence Listing, specifically SEQ ID Nos. 1-30. The Sequence Listing consists of functionally comparable proteins. Polypeptides comprised of a sequence within and defined by one of the consensus sequences can be utilized for the purposes of the invention, namely to make transgenic plants with modulated biomass.

5. Use of the Genes to Make Transgenic Plants

To use the sequences of the present invention or a combination of them or parts and/or mutants and/or fusions and/or variants of them, recombinant DNA constructs are prepared that comprise the polynucleotide sequences of the invention inserted into a vector and that are suitable for transformation of plant cells. The construct can be made using standard recombinant DNA techniques (see, 16) and can be introduced into the plant species of interest by, for example, Agrobacterium-mediated transformation, or by other means of transformation, for example, as disclosed below.

The vector backbone may be any of those typically used in the field such as plasmids, viruses, artificial chromosomes, BACs, YACs, PACs and vectors such as, for instance, bacteria-yeast shuttle vectors, lamda phage vectors, T-DNA fusion vectors and plasmid vectors (see, 17-24).

Typically, the construct comprises a vector containing a nucleic acid molecule of the present invention with any desired transcriptional and/or translational regulatory sequences such as, for example, promoters, UTRs, and 3' end termination sequences. Vectors may also include, for example, origins of replication, scaffold attachment regions (SARs), markers, homologous sequences, and introns. The vector may also comprise a marker gene that confers a selectable phenotype on plant cells. The marker may preferably encode a biocide resistance trait, particularly antibiotic resistance, such as resistance to, for example, kanamycin, bleomycin, or hygromycin, or herbicide resistance, such as resistance to, for example, glyphosate, chlorosulfuron or phosphinotricin.

It will be understood that more than one regulatory region may be present in a recombinant polynucleotide, e.g., introns, enhancers, upstream activation regions, transcription terminators, and inducible elements. Thus, more than one regulatory region can be operably linked to said sequence.

To "operably link" a promoter sequence to a sequence, the translation initiation site of the translational reading frame of said sequence is typically positioned between one and about fifty nucleotides downstream of the promoter. A promoter can, however, be positioned as much as about 5,000 nucleotides upstream of the translation initiation site, or about 2,000 nucleotides upstream of the transcription start site. A promoter typically comprises at least a core (basal) promoter. A promoter also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell* 1:977-984 (1989).

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to said sequence.

Some suitable promoters initiate transcription only, or predominantly, in certain cell types. For example, a promoter that is active predominantly in a reproductive tissue (e.g., fruit, ovule, pollen, pistils, female gametophyte, egg cell, central cell, nucellus, suspensor, synergid cell, flowers, embryonic tissue, embryo sac, embryo, zygote, endosperm, integument, or seed coat) can be used. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et al., *Plant Cell*, 1:855-866 (1989); Bustos, et al., *Plant Cell*, 1:839-854 (1989); Green, et al., *EMBO J.* 7, 4035-4044 (1988); Meier, et al., *Plant Cell*, 3, 309-316 (1991); and Zhang, et al., *Plant Physiology* 110: 1069-1079 (1996).

Examples of various classes of promoters are described below. Some of the promoters indicated below are described in more detail in U.S. Patent Application Ser. Nos. 60/505, 689; 60/518,075; 60/544,771; 60/558,869; 60/583,691; 60/619,181; 60/637,140; 10/950,321; 10/957,569; 11/058, 689; 11/172,703; 11/208,308; and PCT/US05/23639. It will be appreciated that a promoter may meet criteria for one classification based on its activity in one plant species, and yet meet criteria for a different classification based on its activity in another plant species.

Other Regulatory Regions: A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

Various promoters can be used to drive expression of the genes of the present invention. Nucleotide sequences of such promoters are set forth in SEQ ID NOs: 31-109. Some of them can be broadly expressing promoters, others may be more tissue preferential.

A promoter can be said to be "broadly expressing" when it promotes transcription in many, but not necessarily all, plant tissues or plant cells. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326 (SEQ ID NO:106), YP0144 (SEQ ID NO:85), YP0190 (SEQ ID NO:89), p13879 (SEQ ID NO:105), YP0050 (SEQ ID NO:65), p32449 (SEQ ID NO:107), YP0158 (SEQ ID NO:87), YP0214 (SEQ ID NO:91), YP0380 (SEQ ID NO:100), PT0848 (SEQ ID NO:56), and PTO633 (SEQ ID NO:37). Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Root-active promoters drive transcription in root tissue, e.g., root endodermis, root epidermis, or root vascular tissues. In some embodiments, root-active promoters are root-preferential promoters, i.e., drive transcription only or predominantly in root tissue. Root-preferential promoters include the YP0128 (SEQ ID NO: 82), YP0275 (SEQ ID NO: 93), PT0625 (SEQ ID NO: 36), PT0660 (SEQ ID NO: 39), PT0683 (SEQ ID NO: 44), and PT0758 (SEQ ID NO: 52). Other root-preferential promoters include the PT0613 (SEQ ID NO: 35), PT0672 (SEQ ID NO: 41), PT0688 (SEQ ID NO: 45), and PT0837 (SEQ ID NO: 54), which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA* 86:7890-7894 (1989)), root cell specific promoters reported by Conkling et al., *Plant Physiol.* 93:1203-12311 (1990), and the tobacco RD2 gene promoter.

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin gene promoter (Bustos et al., *Plant Cell* 1(9):839-853 (1989)), the soybean trypsin inhibitor promoter (Riggs et al., *Plant Cell* 1(6):609-621 (1989)), the ACP promoter (Baerson et al., *Plant Mol Biol*, 22(2):255-267 (1993)), the stearoyl-ACP desaturase gene (Slocombe et al., *Plant Physiol* 104(4):167-176 (1994)), the soybean α' subunit of β-conglycinin promoter (Chen et al., *Proc Natl Acad Sci USA* 83:8560-8564 (1986)), the oleosin promoter (Hong et al., *Plant Mol Biol* 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.* 13:5829-5842 (1993)), the beta-amylase gene promoter, and the barley hordein gene promoter. Other maturing endosperm promoters include the YP0092 (SEQ ID NO: 68), PT0676 (SEQ ID NO: 42), and PT0708 (SEQ ID NO: 47).

Promoters that drive transcription in ovary tissues such as the ovule wall and mesocarp can also be useful, e.g., a polygalacturonidase promoter, the banana TRX promoter, and the melon actin promoter. Other such promoters that drive gene expression preferentially in ovules are YP0007 (SEQ ID NO: 60), YP0111 (SEQ ID NO: 76), YP0092 (SEQ ID NO: 68), YP0103 (SEQ ID NO: 73), YP0028 (SEQ ID NO: 63), YP0121 (SEQ ID NO: 81), YP0008 (SEQ ID NO: 61), YP0039 (SEQ ID NO: 64), YP0115 (SEQ ID NO: 77), YP0119 (SEQ ID NO: 62), YP0120 (SEQ ID NO: 80) and YP0374 (SEQ ID NO: 98).

In some other embodiments of the present invention, embryo sac/early endosperm promoters can be used in order drive transcription of the sequence of interest in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmycl (see, Urao (1996) *Plant Mol. Biol.,* 32:571-57; Conceicao (1994) *Plant,* 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics,* 142:1009-1020); maize Cat3 (see, GenBank No. L05934; Abler (1993) *Plant Mol. Biol.,* 22:10131-1038). Other promoters include the following *Arabidopsis* promoters: YP0039 (SEQ ID NO: 64), YP0101 (SEQ ID NO: 71), YP0102 (SEQ ID NO: 72), YP0110 (SEQ ID NO: 75), YP0117 (SEQ ID NO: 78), YP0119 (SEQ ID NO: 79), YP0137 (SEQ ID NO: 83), DME, YP0285 (SEQ ID NO: 94), and YP0212 (SEQ ID NO: 90). Other promoters that may be useful include the following rice promoters: p530c10, pOsFIE2-2, pOsMEA, pOsYp102, and pOsYp285.

Promoters that preferentially drive transcription in zygotic cells following fertilization can provide embryo-preferential expression and may be useful for the present invention. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654, YP0097 (SEQ ID NO: 70), YP0107 (SEQ ID NO: 74), YP0088 (SEQ ID NO: 67), YP0143 (SEQ ID NO: 84), YP0156 (SEQ ID NO: 86), PT0650 (SEQ ID NO: 38), PT0695 (SEQ ID NO: 46), PT0723 (SEQ ID NO: 49), PT0838 (SEQ ID NO: 55), PT0879 (SEQ ID NO: 58) and PT0740 (SEQ ID NO: 50).

Promoters active in photosynthetic tissue in order to drive transcription in green tissues such as leaves and stems are of particular interest for the present invention. Most suitable are promoters that drive expression only or predominantly such tissues. Examples of such promoters include the ribulose-1, 5-bisphosphate carboxylase (RbcS) promoters such as the RbcS promoter from eastern larch (*Larix laricina*), the pine cab6 promoter (Yamamoto et al., *Plant Cell Physiol.* 35:773-778 (1994)), the Cab-1 gene promoter from wheat (Fejes et al., *Plant Mol. Biol.* 15:921-932 (1990)), the CAB-1 promoter from spinach (Lubberstedt et al., *Plant Physiol.* 104:997-1006 (1994)), the cab1R promoter from rice (Luan et al., *Plant Cell* 4:971-981 (1992)), the pyruvate orthophosphate dikinase (PPDK) promoter from corn (Matsuoka et al., *Proc Natl Acad. Sci USA* 90:9586-9590 (1993)), the tobacco Lhcb1*2 promoter (Cerdan et al., *Plant Mol. Biol.* 33:245-255 (1997)), the *Arabidopsis thaliana* SUC2 sucrose-H+ symporter promoter (Truernit et al., *Planta* 196:564-570 (1995)), and thylakoid membrane protein promoters from spinach (psaD, psaF, psaE, PC, FNR, atpC, atpD, cab, rbcS. Other promoters that drive transcription in stems, leafs and green tissue are PT0535 (SEQ ID NO: 33), PT0668 (SEQ ID NO: 32), PT0886 (SEQ ID NO: 59), PR0924 (SEQ ID NO: 108), YP0144 (SEQ ID NO: 85), YP0380 (SEQ ID NO: 100) and PT0585 (SEQ ID NO: 34).

In some other embodiments of the present invention, inducible promoters may be desired. Inducible promoters drive transcription in response to external stimuli such as chemical agents or environmental stimuli. For example, inducible promoters can confer transcription in response to hormones such as giberellic acid or ethylene, or in response to light or drought. Examples of drought inedible promoters are YP0380 (SEQ ID NO: 100), PT0848 (SEQ ID NO: 56), YP0381 (SEQ ID NO: 101), YP0337 (SEQ ID NO: 96), YP0337 (SEQ ID NO: 96), PT0633 (SEQ ID NO: 37), YP0374 (SEQ ID NO: 98), PT0710 (SEQ ID NO: 48), YP0356 (SEQ ID NO: 97), YP0385 (SEQ ID NO: 103), YP0396 (SEQ ID NO: 104), YP0384 (SEQ ID NO: 102), YP0384 (SEQ ID NO: 102), PT0688 (SEQ ID NO: 45), YP0286 (SEQ ID NO: 95), YP0377 (SEQ ID NO: 99), and PD1367 (SEQ ID NO: 109). Examples of promoters induced by nitrogen are PT0863 (SEQ ID NO: 57), PT0829 (SEQ ID NO: 53), PT0665 (SEQ ID NO: 40) and PT0886 (SEQ ID NO: 59). An example of a shade inducible promoter is PR0924.

Other Promoters: Other classes of promoters include, but are not limited to, leaf-preferential, stem/shoot-preferential, callus-preferential, guard cell-preferential, such as PT0678 (SEQ ID NO: 43), and senescence-preferential promoters. Promoters designated YP0086 (SEQ ID NO: 66), YP0188 (SEQ ID NO: 88), YP0263 (SEQ ID NO: 92), PT0758 (SEQ ID NO: 52), PT0743 (SEQ ID NO: 51), PT0829 (SEQ ID NO: 53), YP0119 (SEQ ID NO: 79), and YP0096 (SEQ ID NO: 69), as described in the above-referenced patent applications, may also be useful.

Alternatively, misexpression can be accomplished using a two component system, whereby the first component consists of a transgenic plant comprising a transcriptional activator operatively linked to a promoter and the second component consists of a transgenic plant that comprise a nucleic acid molecule of the invention operatively linked to the target-binding sequence/region of the transcriptional activator. The two transgenic plants are crossed and the nucleic acid molecule of the invention is expressed in the progeny of the plant. In another alternative embodiment of the present invention, the misexpression can be accomplished by having the sequences of the two component system transformed in one transgenic plant line.

Another alternative consists in inhibiting expression of a biomass-modulating polypeptide in a plant species of interest. The term "expression" refers to the process of converting genetic information encoded in a polynucleotide into RNA through transcription of the polynucleotide (i.e., via the enzymatic action of an RNA polymerase), and into protein, through translation of mRNA. "Up-regulation" or "activation" refers to regulation that increases the production of expression products relative to basal or native states, while "down-regulation" or "repression" refers to regulation that decreases production relative to basal or native states.

A number of nucleic-acid based methods, including antisense RNA, ribozyme directed RNA cleavage, and interfering RNA (RNAi) can be used to inhibit protein expression in plants. Antisense technology is one well-known method. In this method, a nucleic acid segment from the endogenous gene is cloned and operably linked to a promoter so that the antisense strand of RNA is transcribed. The recombinant vector is then transformed into plants, as described above, and the antisense strand of RNA is produced. The nucleic acid segment need not be the entire sequence of the endogenous gene to be repressed, but typically will be substantially identical to at least a portion of the endogenous gene to be repressed. Generally, higher homology can be used to compensate for the use of a shorter sequence. Typically, a sequence of at least 30 nucleotides is used (e.g., at least 40, 50, 80, 100, 200, 500 nucleotides or more).

Thus, for example, an isolated nucleic acid provided herein can be an antisense nucleic acid to one of the aforementioned nucleic acids encoding a biomass-modulating polypeptide. A nucleic acid that decreases the level of a transcription or translation product of a gene encoding a biomass-modulating polypeptide is transcribed into an antisense nucleic acid similar or identical to the sense coding sequence of the biomass-modulating polypeptide. Alternatively, the transcription product of an isolated nucleic acid can be similar or identical to the sense coding sequence of a biomass-modulating polypeptide, but is an RNA that is unpolyadenylated, lacks a 5' cap structure, or contains an unsplicable intron.

In another method, a nucleic acid can be transcribed into a ribozyme, or catalytic RNA, that affects expression of an mRNA. (See, U.S. Pat. No. 6,423,885). Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman, et al., *Proc. Natl. Acad. Sci. USA,* 92(13): 6175-6179 (1995); de Feyter and Gaudron, Methods in Molecular Biology, Vol. 74, Chapter 43, "Expressing Ribozymes in Plants", Edited by Turner, P. C, Humana Press Inc., Totowa, N.J. RNA endoribonucleases such as the one that occurs naturally in *Tetrahymena thermophila*, and which have been described extensively by Cech and collaborators can be useful. See, for example, U.S. Pat. No. 4,987,071.

Methods based on RNA interference (RNAi) can be used. RNA interference is a cellular mechanism to regulate the expression of genes and the replication of viruses. This mechanism is thought to be mediated by double-stranded small interfering RNA molecules. A cell responds to such a double-stranded RNA by destroying endogenous mRNA having the same sequence as the double-stranded RNA. Methods for designing and preparing interfering RNAs are known to those of skill in the art; see, e.g., WO 99/32619 and WO 01/75164. For example, a construct can be prepared that includes a sequence that is transcribed into an interfering RNA. Such an RNA can be one that can anneal to itself, e.g., a double stranded RNA having a stem-loop structure. One strand of the stem portion of a double stranded RNA comprises a sequence that is similar or identical to the sense coding sequence of the polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of the biomass-modulating polypeptide of interest, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron. See, e.g., WO 99/53050.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.,* 7:187-195; Hyrup et al., 1996, *Bioorgan. Med. Chem.,* 4: 5-23. In addition, the deoxyphosphate backbone can be replaced with, for example, a phosphorothioate or phosphorodithioate backbone, a phosphoroamidite, or an alkyl phosphotriester backbone.

Transformation

Nucleic acid molecules of the present invention may be introduced into the genome or the cell of the appropriate host plant by a variety of techniques. These techniques, able to transform a wide variety of higher plant species, are well known and described in the technical and scientific literature (see, e.g., 28-29).

A variety of techniques known in the art are available for the introduction of DNA into a plant host cell. These techniques include transformation of plant cells by injection (30), microinjection (31), electroporation of DNA (32), PEG (33), use of biolistics (34), fusion of cells or protoplasts (35), and via T-DNA using *Agrobacterium tumefaciens* (36-37) or *Agrobacterium rhizogenes* (38) or other bacterial hosts (39), for example.

In addition, a number of non-stable transformation methods that are well known to those skilled in the art may be desirable for the present invention. Such methods include, but are not limited to, transient expression (40) and viral transfection (41).

Seeds are obtained from the transformed plants and used for testing stability and inheritance. Generally, two or more generations are cultivated to ensure that the phenotypic feature is stably maintained and transmitted.

A person of ordinary skill in the art recognizes that after the expression cassette is stably incorporated in transgenic plants and confirmed to be operable, it can be introduced into other plants by sexual crossing. Any of a number of standard breeding techniques can be used, depending upon the species to be crossed.

The nucleic acid molecules of the present invention may be used to confer the trait of an altered flowering time.

The nucleic acid molecules of the present invention encode appropriate proteins from any organism, but are preferably found in plants, fungi, bacteria or animals.

The methods according to the present invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belonging to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales, for example, are also suitable. Monocotyledonous plants belonging to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales also may be useful in embodiments of the present invention. Further examples include, but are not limited to, plants belonging to the class of the Gymnospermae are Pinales, Ginkgoales, Cycadales and Gnetales.

The methods of the present invention are preferably used in plants that are important or interesting for agriculture, horticulture, biomass for bioconversion and/or forestry. Non-limiting examples include, for instance, tobacco, oilseed rape, sugar beet, potatoes, tomatoes, cucumbers, peppers, beans, peas, citrus fruits, avocados, peaches, apples, pears, berries, plumbs, melons, eggplants, cotton, soybean, sunflowers, roses, poinsettia, petunia, guayule, cabbages, spinach, alfalfa, artichokes, sugarcane, mimosa, *Servicea lespedera*, corn, wheat, rice, rye, barley, sorghum and grasses such as switch grass, giant reed, Bermuda grass, Johnson grass or turf grass, millet, hemp, bananas, poplars, eucalyptus trees and conifers.

Homologues Encompassed by the Invention

It is known in the art that one or more amino acids in a sequence can be substituted with other amino acid(s), the charge and polarity of which are similar to that of the substituted amino acid, ie. a conservative amino acid substitution, resulting in a biologically/functionally silent change. Conservative substitutes for an amino acid within the polypeptide sequence can be selected from other members of the class to which the amino acid belongs. Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

Nucleic acid molecules of the present invention can comprise sequences that differ from those encoding a protein or fragment thereof selected from the group consisting of [leads 11, 17, 50, 58, 64, and 67, nucleotides] due to the fact that the different nucleic acid sequence encodes a protein having one or more conservative amino acid changes.

Biologically functional equivalents of the polypeptides, or fragments thereof, of the present invention can have about 10 or fewer conservative amino acid changes, more preferably about 7 or fewer conservative amino acid changes, and most preferably about 5 or fewer conservative amino acid changes. In a preferred embodiment of the present invention, the polypeptide has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Identification of Useful Nucleic Acid Molecules and Their Corresponding Nucleotide Sequences The nucleic acid molecules, and nucleotide sequences thereof, of the present invention were identified by use of a variety of screens that are predictive of nucleotide sequences that provide plants with altered size, vegetative growth, organ number, plant architecture and/or biomass. One or more of the following screens were, therefore, utilized to identify the nucleotide (and amino acid) sequences of the present invention.

The present invention is further exemplified by the following examples. The examples are not intended to in any way limit the scope of the present application and its uses.

6. Experiments Confirming the Usefulness of the Polynucleotides and Polypeptides of the Invention General Protocols

*Agrobacterium*—Mediated Transformation of *Arabidopsis*

Wild-type *Arabidopsis thaliana* Wassilewskija (WS) plants are transformed with Ti plasmids containing clones in the sense orientation relative to the 35S promoter. A Ti plasmid vector useful for these constructs, CRS 338, contains the Ceres-constructed, plant selectable marker gene phosphinothricin acetyltransferase (PAT), which confers herbicide resistance to transformed plants.

Ten independently transformed events are typically selected and evaluated for their qualitative phenotype in the $T_1$ generation.

Preparation of Soil Mixture: 24L SunshineMix #5 soil (Sun Gro Horticulture, Ltd., Bellevue, Wash.) is mixed with 16L Therm-O-Rock vermiculite (Therm-O-Rock West, Inc., Chandler, Ariz.) in a cement mixer to make a 60:40 soil mixture. To the soil mixture is added 2 Tbsp Marathon 1% granules (Hummert, Earth City, Mo.), 3 Tbsp OSMOCOTE® 14-14-14 (Hummert, Earth City, Mo.) and 1 Tbsp Peters fertilizer 20-20-20 (J. R. Peters, Inc., Allentown, Pa.), which are first added to 3 gallons of water and then added to the soil and mixed thoroughly. Generally, 4-inch diameter pots are filled with soil mixture. Pots are then covered with 8-inch squares of nylon netting.

Planting: Using a 60 mL syringe, 35 mL of the seed mixture is aspirated. 25 drops are added to each pot. Clear propagation domes are placed on top of the pots that are then placed under 55% shade cloth and subirrigated by adding 1 inch of water.

Plant Maintenance: 3 to 4 days after planting, lids and shade cloth are removed. Plants are watered as needed. After 7-10 days, pots are thinned to 20 plants per pot using forceps. After 2 weeks, all plants are subirrigated with Peters fertilizer at a rate of 1 Tsp per gallon of water. When bolts are about 5-10 cm long, they are clipped between the first node and the base of stem to induce secondary bolts. Dipping infiltration is performed 6 to 7 days after clipping.

Preparation of *Agrobacterium*: To 150 mL fresh YEB is added 0.1 mL each of carbenicillin, spectinomycin and rifampicin (each at 100 mg/ml stock concentration). *Agrobacterium* starter blocks are obtained (96-well block with *Agrobacterium* cultures grown to an $OD_{600}$ of approximately 1.0) and inoculated one culture vessel per construct by transferring 1 mL from appropriate well in the starter block. Cultures are then incubated with shaking at 27° C. Cultures are spun down after attaining an $OD_{600}$ of approximately 1.0 (about 24 hours). 200 mL infiltration media is added to resuspend *Agrobacterium* pellets. Infiltration media is prepared by adding 2.2 g MS salts, 50 g sucrose, and 5 μl 2 mg/ml benzylaminopurine to 900 ml water.

Dipping Infiltration: The pots are inverted and submerged for 5 minutes so that the aerial portion of the plants are in the *Agrobacterium* suspension. Plants are allowed to grow normally and seed is collected.

High-throughput Phenotypic Screening of Misexpression Mutants: Seed is evenly dispersed into water-saturated soil in pots and placed into a dark 4° C. cooler for two nights to promote uniform germination. Pots are then removed from the cooler and covered with 55% shade cloth for 4-5 days. Cotyledons are fully expanded at this stage. FINALE® (Sanofi Aventis, Paris, France) is sprayed on plants (3 ml FINALE® diluted into 48 oz. water) and repeated every 3-4 days until only transformants remain.

Screening: Screening is routinely performed at four stages: Seedling, Rosette, Flowering, and Senescence.

Seedling—the time after the cotyledons have emerged, but before the $3^{rd}$ true leaf begins to form.

Rosette—the time from the emergence of the $3^{rd}$ true leaf through just before the primary bolt begins to elongate.

Flowering—the time from the emergence of the primary bolt to the onset of senescence (with the exception of noting the flowering time itself, most observations should be made at the stage where approximately 50% of the flowers have opened).

Senescence—the time following the onset of senescence (with the exception of "delayed senescence", most observations should be made after the plant has completely dried). Seeds are then collected.

Screens: Screening for increased size, vegetative growth and/or biomass is performed by taking measurements, specifically $T_2$ measurements were taken as follows:

Days to Bolt=number of days between sowing of seed and emergence of first inflorescence.

Rosette Leaf Number at Bolt=number of rosette leaves present at time of emergence of first inflorescence.

Rosette Area=area of rosette at time of initial inflorescence emergence, using formula $((L \times W) * 3.14)/4$.

Height=length of longest inflorescence from base to apex. This measurement was taken at the termination of flowering/onset of senescence.

Primary Inflorescence Thickness=diameter of primary inflorescence 2.5 cm up from base. This measurement was taken at the termination of flowering/onset of senescence.

Inflorescence Number=total number of unique inflorescences. This measurement was taken at the termination of flowering/onset of senescence.

PCR was used to amplify the cDNA insert in one randomly chosen $T_2$ plant. This PCR product was then sequenced to confirm the sequence in the plants.

7. Results

EXAMPLE 1

Lead 11; (ME01795; Ceres cDNA 5662747; Clone 8161)

Ten independently transformed events were selected and evaluated for their qualitative phenotype in the $T_1$ generation as per standard protocol. Three events showing the strongest $T_1$ phenotypes were chosen for evaluation in the $T_2$ generation. The $T_2$ growth conditions followed the above $T_1$ protocol. The experimental design differed from the $T_1$ planting in that each $T_2$ plant was contained with its own pot, and no herbicide selection was used. All the pots for each $T_2$ event were contained within the same flat and the plants were randomly distributed within each flat. The controls for each set of measurements were the segregating progeny of other $T_1$ events which did not contain this gene (internal controls). All analyses were done via soil-based experiments under long day light conditions (16 hours) in the Ceres greenhouse.

All ten events showed a variety of phenotypes different from wild-type transgenic controls (Table 1. The most pronounced variant phenotype was that of reduced secondary inflorescence formation, slightly delayed flowering time, larger rosettes with more leaves, and tall, thick inflorescences.

TABLE 1

Qualitative phenotypes observed in 35S::cDNA 5662747 $T_1$ events

| Event | Increased Rosette Size Increased Rosette Leaf Number | Late Flowering | Reduced Secondary Inflor. Formation | Tall & Thick | Fertility Defects |
|---|---|---|---|---|---|
| ME01795-01 | x | X | x | x | |
| ME01795-02 | | X | x | x | |
| ME01795-03 | | | | | x |
| ME01795-04 | x | X | x | x | |
| ME01795-05 | | | x | | |
| ME01795-06 | x | X | x | x | |
| ME01795-07 | | X | x | x | |
| ME01795-08 | | | x | | |
| ME01795-09 | | | x | | |
| ME01795-10 | x | X | x | x | |

Events 01, 04, and 10 were evaluated in greater detail in the $T_2$ generation. Fourteen individuals were sown for each event. The transgenic plants of all 3 events showed increased height, primary inflorescence thickness, and delay of flowering time to a 0.01 level of statistical significance (Table 2). These plants also had qualitatively larger rosettes which contained more leaves (data not shown). All plants, noted in the table as ME01795-01, ME01795-04, or ME01795-10, were segregating progeny of the $T_1$ event which we had confirmed to contain the transgene under test. All plants noted in the table as -01 Control, -04 Control, or -10 Controls were segregating progeny of the $T_1$ event which did not contain the transgene under test (internal controls).

One item of note in the $T_2$ analysis is that the reduced secondary inflorescence formation observed in $T_1$ plants is no longer present in $T_2$ plants. In addition, the delay in flowering time appears to have increased in severity from the $T_1$ to $T_2$ generation.

Segregation frequencies of the transgene under test suggest that each event contains a single insert, as determined by a Chi-square test (data not shown).

TABLE 2

Quantitative phenotypes seen in 35S::cDNA 5662747 $T_2$ events

| Event/Control | Number of Observations | Height (cm) | Primary Inflorescence Thickness (mm) | Days to Bolt |
|---|---|---|---|---|
| ME01795-01 | 8 | 64.3* | 1.062* | 29.8* |
| -01 Control | 6 | 48.3 | 1.048 | 24.5 |
| ME01795-04 | 9 | 70.9* | 1.065* | 35.8* |
| -04 Control | 5 | 42.4 | 1.047 | 25.8 |
| ME01795-10 | 8 | 67.9* | 1.069* | 31.3* |
| -10 Control | 6 | 43.3 | 1.049 | 25.3 |

*significantly different from control at 0.01 level, via t-test

Summary of results:
  The ectopic expression of cDNA 5662747 with a strong constitutive promoter (35S) results in taller plants, with thicker inflorescences, a larger rosette, and more rosette leaves.
  5662747 is normally expressed in shoot and root apices, suggesting that the encoded protein may help to regulate meristem function.
  The increase in plant size seen by this expression is accompanied by a delay in flowering time, but no reduction in fertility.
  As the $T_1$ plants had a much less severe delay in flowering than the $T_2$ plants, but still produced the large-plant phenotype, it may be possible to use a promoter of different strength or with a different spatial expression pattern with the cDNA to maintain an increase in plant height and stem/inflorescence thickness without any increase in flowering time.
  It may also be a useful gene to increase root growth, given the similar expression pattern in shoot meristems and root tip cells.
  As a result, this gene is useful to increase vegetative biomass to give an improved source:sink ratio and improved fixation of carbon to sucrose and starch. Taller inflorescences give the opportunity for more flowers and therefore more seeds. The combination of improved biomass and inflorescence stature can give a significant improvement in yield. Thicker inflorescences can prevent against "snap" against wind, rain or drought and there was no detectable difference in fertility factors such as silique number and seed fill.

EXAMPLE 2

Lead 12/67; ME03459 and ME04358; Ceres cDNA 12337825/14296577; Clone 8490/96

Experiments were performed substantially as described in Example 1, but with different seeds. Ten independently transformed events were selected and evaluated for their qualitative phenotype in the $T_1$ generation as per standard protocol. Two events showing the most advantageous $T_1$ phenotypes (large, late-flowering) were chosen for evaluation in the $T_2$ generation. The $T_2$ growth conditions follow the above $T_1$ protocol. The experimental design differs from the $T_1$ planting in that each $T_2$ plant is contained within its own pot, and no herbicide selection is used. All pots for each $T_2$ event are contained within the same flat and the plants are randomly distributed within each flat. The controls for each set of measurements are the segregating progeny of the given $T_1$ event which do not contain the T-DNA (internal controls). All analyses are done via soil-based experiments under long day light conditions (16 hours) in the Ceres greenhouse.

All ten events were late flowering, produced larger rosettes with more leaves and tall, thick inflorescences compared to the controls (Table 3). The transgenic "control" was a set of different 35S cDNA expressing plants which were indistinguishable from the untransformed WS wild type.

TABLE 3

Qualitative phenotypes observed in 35S::cDNA 12337825 $T_1$ events

| Event | Increased Rosette Size Increased Rosette Leaf Number | Late Flowering | Tall & Thick |
|---|---|---|---|
| ME03459-01 | x | X | X |
| ME03459-02 | x | X | X |
| ME03459-03 | x | X | x |
| ME03459-04 | x | X | x |
| ME03459-05 | x | X | x |
| ME03459-06 | x | X | x |
| ME04358-01 | x | X | x |
| ME04358-02 | x | X | x |
| ME04358-03 | x | X | x |
| ME04358-04 | x | X | x |

Events ME03459-01 and ME03459-04 were evaluated in greater detail in the $T_2$ generation. Seventeen individuals were sown and observed for event 01, whereas 18 individuals were sown and observed for event 04. The transgenic plants for both events showed increased height, increased primary inflorescence thickness, increased number of rosette leaves, a larger rosette, and delay of flowering time to a 0.05 level of statistical significance (Table 4). Both events had normal fertility. All plants noted in the table as ME03459-01 or ME03459-04 were segregating progeny of the $T_1$ event which we had confirmed to contain the transgene under test. All plants noted in the table as -01 Control or -04 Control were segregating progeny of the given T1 event, which did not contain the transgene (internal controls).

Both events produce significantly more seeds than the control, as would be expected for a typical, fertile, late flowering plant.

Event ME03459-01 exhibited the strongest as noted in Table 4. The rosette area, number of leaves, thickness of the inflorescence and days to bolt are all greater than event -04.

Segregation frequencies of the transgene under test suggest that each event contains a single insert, as calculated by a Chi-square test.

TABLE 4

Quantitative phenotypes observed in 35S::cDNA 12337825 T$_2$ events

| Event/Control | Number of Observations | Rosette Area (mm$^2$) | Number of Leaves | Height (cm) | Primary Inflorescence Thickness (inches) | Days to Bolt |
|---|---|---|---|---|---|---|
| ME03459-01 | 14 | 7023.0* | 11.0* | 75.6* | 0.068* | 21.9* |
| -01 Control | 3 | 2348.5 | 8.0 | 52.2 | 0.050 | 19.0 |
| ME03459-04 | 9 | 4977.7* | 9.4* | 68.9* | 0.055* | 20.8* |
| -04 Control | 5 | 2521.1 | 7.5 | 54.0 | 0.051 | 18.1 |

*significantly different from control at 0.05 level, via t-test

Summary of Results:

The ectopic expression of cDNA 12337825 with a strong constitutive promoter (35S) results in taller plants, with thicker inflorescences, a larger rosette, and increased number of rosette leaves.

12337825 is normally regulated in shoot and root apices, suggesting that the encoded protein may help to regulate meristem function.

The increase in plant size observed by this expression is accompanied by a delay in flowering time, but no reduction in fertility.

It is also a useful gene to increase root growth, given the similar expression pattern in shoot meristems and root tip cells.

As a result, this gene is useful to increase vegetative biomass and give an improved source:sink ratio and improved fixation of carbon to sucrose and starch, and to improved yield. Taller inflorescences give the opportunity for more flowers and therefore more seeds. The combination of improved biomass and inflorescence sure can give a significant improvement in yield. In addition, thicker inflorescences can prevent "snap" against wind, rain or drought.

ME04358 was identified from a T$_1$ screen looking for mutant developmental and morphological phenotypes. All four independent transgenic events containing Clone 96 (ME04358) were screened in the T$_1$ generation for the presence of mutant developmental and morphological phenotypes. All events were taller with larger rosettes than wild-type.

Events ME04358-01 and -02 show 3:1 and 15:1 (R:S) segregation for Finale™, respectively. Event ME04358-01 showed a Mendelian segregation of 3:1 (R:S) for Finale™ in the T$_2$ generation. Event ME04358-02 segregated 15:1 (R:S) for Finale™ in the T$_2$ generation.

Both T$_2$ events of ME04358 show increased rosette/leaf size and inflorescence height compared to controls. Events ME04358-01 and -02 were tested for the quantitative traits of Plant Size. When grown under constant light, both events had significantly larger rosettes and taller inflorescences with a p-value less than or equal to 0.05 (Table 5). Both events were also slightly, yet statistically significantly later flowering than controls. Both events trended toward having slightly thicker inflorescences than the controls, but these data were not statistically significant at p≦0.05. Under long-day conditions, the plants were larger than controls but had an exaggerated delay in flowering time.

TABLE 5

Analysis of Rosette Area, Primary Inflorescence Thickness, Plant Height, and Days to Flowering for ME04358-01 & -02. Both events had statistically larger rosettes, taller inflorescences, and a slight delay in flowering. All values denote the mean of the population.

| Event/Control | Number of Observations | Rosette Area (mm$^2$) | Primary Inflorescence Thickness (mm) | Height (cm) | Days to Flowering |
|---|---|---|---|---|---|
| ME04358-01 | 12 | 5922* | 1.548 | 65.1* | 24.0* |
| -01 Control | 14 | 4602 | 1.481 | 55.4 | 21.6 |
| ME04358-02 | 11 | 5403* | 1.576 | 62.3* | 23.2* |
| -02 Control | 14 | 4602 | 1.481 | 55.4 | 21.6 |

*Indicates statistical significance with p ≦ 0.05, via t-test

Summary of Results:

The four T$_1$ plants were larger and taller than the controls. Events ME04358-01 and -02 were screened.

Germination—No detectable reduction in germination rate

General morphology/architecture—Plants were larger than the controls

Days to flowering—A statistical delay in flowering was observed for both events

Rosette area 7 days post-bolting—The rosettes of both events were larger than controls Plant height—An increase in height was observed for both events Fertility (silique number and seed fill)—No observable differences between experimentals and controls.

EXAMPLE 3

Lead 13/64; ME01990; Ceres cDNA
12420510/1434106; Clone 258241/25821

Four independently transformed events were selected and evaluated for their qualitative phenotype in the T$_1$ generation as per standard protocol. Two events showing the most advantageous T$_1$ phenotypes (large plants with larger rosettes, more leaves and tall, thick inflorescences) were chosen for evaluation in the T$_2$ generation. The T$_2$ growth conditions follow the above T$_1$ protocol. The experimental design differs from the T$_1$ planting in that each T$_2$ plant is contained within its own pot, and no herbicide selection is used. All pots for each T$_2$ event are contained within the same flat and the plants are randomly distributed within each flat. The controls for each set of measurements are the segregating progeny of the given T$_1$ event which do not contain the T-DNA (internal controls). All analyses are done via soil-based experiments under long day light conditions (16 hours) in the Ceres greenhouse.

Two of the 4 events produced larger rosettes with more leaves and tall, thick inflorescences (Table 6) compared to the controls. The transgenic "control" was a set of different 35S::cDNA expressing plants which were indistinguishable from the untransformed WS wildtype.

TABLE 6

Qualitative phenotypes observed in 35S::cDNA 12420510 $T_1$ events

| Event | Increased Rosette Size Increased Rosette Leaf Number | Tall & Thick Inflorescence |
|---|---|---|
| ME01990-01 | | |
| ME01990-02 | x | x |
| ME01990-03 | x | x |
| ME01990-04 | | |

Events ME01990-02 and ME01990-03 were evaluated in greater detail in the $T_2$ generation. Eighteen individuals were sown and observed for each event. The transgenic plants for both events showed increased height, increased number of rosette leaves, a larger rosette, and delay of flowering time to a 0.05 level of statistical significance (Table 7). Although both events had visibly thicker inflorescences in the T1 generation, only event -03- proved to be quantitatively thicker to a 0.05 level of statistical significance (Table 7). Both events had normal fertility. All plants noted in the table as ME01990-02 and ME01990-03 were segregating progeny of the $T_1$ event which we had confirmed to contain the transgene under test. All plants noted in the table as -02 Control or -03 Control were segregating progeny of given T1 events which did not contain the transgene (internal controls).

Both events produce significantly more seeds than the control, as would be expected for a typical, fertile, late flowering plant.

Event ME01991-02 had 6 transgene-containing plants which exhibited the beneficial phenotype and 8 transgene-containing plants which appeared wild-type (not included in the statistical analysis in Table 7). Event ME01991-03 had 7 transgene-containing plants which exhibited the beneficial phenotype and 1 transgene-containing plant which appeared wild-type. Our statistical analyses compared the internal controls to those plants with the beneficial phenotype which contained the transgene.

Segregation frequencies of the transgene under test suggest that each event contains a single insert, as calculated by a Chi-square test.

tion in fertility. This would be a particularly useful gene to employ in crop plants because flowering time is only slightly delayed.

As a result, this gene is useful to increase vegetative biomass and give an improved source:sink ratio and improved fixation of carbon to sucrose and starch, and to improved yield. Taller inflorescences give the opportunity for more flowers and therefore more seeds. The combination of improved biomass and inflorescence stature can give a significant improvement in yield. In addition, thicker inflorescences can prevent "snap" against wind, rain or drought.

ME01990-01, -03; Ceres cDNA 14301106; Clone 25821

$T_2$ plants were scored quantitatively for the previously observed Plant Size phenotype and statistical significance was determined, as per protocol, with one exception. Twelve segregating experimentals and 12 external controls were sown per flat per event.

ME01990 was identified from a $T_1$ screen looking for mutant developmental and morphological phenotypes. All 4 independent transgenic events containing Clone 258241 (ME01990) were screened in the $T_1$ generation for the presence of mutant developmental and morphological phenotypes. Events -02 and -03 appeared larger than the rest of the population.

Both events of ME01990 show 3:1 segregation for Finale™.

Both $T_2$ events of ME01990 show increased rosette/leaf size and inflorescence thickness compared to controls. ME01593, containing the same construct yielded similar results. Events ME01990-02 and -03 were tested for the quantitative traits of Plant Size. Both events had significantly larger rosettes and thicker inflorescences with a p-value less than or equal to 0.05 (Table 8). Event -03 was also slightly, yet statistically significantly later flowering than controls. However, the degree of flowering delay falls within the window of acceptable flowering time as negative phenotypes are defined. Both events trended toward being slightly taller than the controls, but these data were not statistically significant at p≦0.05. When the two events of ME01990 were grown in constant light, they were wildtype in appearance.

In an unrelated experiment, events of ME01593 (also 35S::258241) were tested for the noted quantitative plant size traits under long day conditions. The results of this experiment were equivalent to those of ME01990. ME01593 events had larger rosettes, thicker inflorescences, and were delayed in time to flowering.

TABLE 7

Quantitative phenotypes observed in 35S::cDNA 12420510 $T_2$ events

| Event/Control | Number of Observations | Rosette Area (mm²) | Number of Leaves | Height (cm) | Primary Inflorescence Thickness (inches) | Days to Bolt |
|---|---|---|---|---|---|---|
| ME01990-02 | 6 | 4589.4* | 10.8* | 59.3* | 0.056 | 21.5* |
| -02 Control | 4 | 2628.0 | 8.8 | 54.3 | 0.053 | 19.3 |
| ME01990-03 | 7 | 5589.0* | 11.3* | 57.3* | 0.057* | 22.9* |
| -03 Control | 10 | 1905.2 | 7.9 | 48.6 | 0.048 | 18.9 |

*significantly different from control at 0.05 level, via t-test

Summary of Results:

The ectopic expression of cDNA 12420510 with a strong constitutive promoter (35S) results in taller plants, a larger rosette, and more rosette leaves.

The increase in plant size seen by this expression is accompanied by a slight delay in flowering time, but no reduc- From the $T_1$ analyses of the degree of biomass and late flowering, 14 of the large late flowering lines were tested in the $T_2$ generation under long day and constant light conditions. Most of the 14 lines were severely delayed in flowering under long day and constant light conditions, but several, while delayed in flowering under long day conditions, exhibited a wildtype phenotype under constant light. As such, ME01990 is a late flowering line that has an increased biomass but less than four days delay in flowering under long day conditions.

TABLE 8

Analysis of Rosette Area, Primary Inflorescence Thickness, Plant Height, and Day to Flowering for ME01990-02 & -03. Both events had statistically larger rosettes and thicker inflorescences. All values denote the mean of the population.

| Event/Control | Number of Observations | Rosette Area (mm$^2$) | Primary Inflorescence Thickness (mm) | Height (cm) | Days to Flowering |
|---|---|---|---|---|---|
| ME01990-02 | 9 | 5377* | 1.377* | 47.8 | 24.2 |
| -02 Control | 13 | 4097 | 1.168 | 46.2 | 23.3 |
| ME01990-03 | 9 | 4784* | 1.302* | 49.4 | 27.1* |
| -03 Control | 13 | 3295 | 1.142 | 46.8 | 23.7 |

*Indicates statistical significance with $p \leq 0.05$, via t-test

Events -02 and -03 of ME01990 were screened. Twelve segregating transformants from each event were screened instead of 18, and 12 external wild-type controls were screened instead of 6.

Summary of Results:

Germination—no detectable reduction in germation rate

General morphology/architecture—plants were larger than the controls

Days to flowering—A statistical delay in flowering was observed for Event -03 but not for -02.

Rosette area 7 days post-bolting—The rosettes of both events were larger than controls Plant height—No observable differences between experimentals and controls Fertility (silique number and seed fill)—No observable differences between experimentals and controls.

EXAMPLE 4

Lead 17; ME04249; Ceres cDNA 13495746; Clone 37288

Ten independently transformed events were selected and evaluated for their qualitative phenotype in the $T_1$ generation as per standard protocol. Two events showing the most advantageous $T_1$ phenotypes (plants with larger rosettes, more leaves and thick inflorescences) were chosen for evaluation in the $T_2$ generation. The $T_2$ growth conditions follow the above $T_1$ protocol. The experimental design differs from the $T_1$ planting in that each $T_2$ plant is contained within its own pot, and no herbicide selection is used. All pots for each $T_2$ event are contained within the same flat and the plants are randomly distributed within each flat. The controls for each set of measurements are the segregating progeny of the given $T_1$ event which do not contain the T-DNA (internal controls). All analyses are done via soil-based experiments under long day light conditions (16 hours) in the Ceres.

Five of the 10 events produced larger rosettes with more leaves and thicker inflorescences compared to the controls. These plants were also delayed in flowering time but exhibited normal fertility. Four other events were smaller and/or had fertility defects (Table 9). The transgenic "control" was a set of plants expressing a different 35S::cDNA and which were indistinguishable from the untransformed WS wildtype.

TABLE 9

Qualitative phenotypes observed in $T_1$ events containing 35S::cDNA 13495746 (highlighted events were chosen for $T_2$ evaluation)

| Event | Increased Rosette Size Increased Inflorescence Thickness | Late Flowering | Small | Fertility Defects |
|---|---|---|---|---|
| ME04249-01 |  |  | x |  |
| ME04249-02 |  |  | x | x |
| ME04249-03 | x | x |  |  |
| ME04249-04 | x | x |  |  |
| ME04249-05 | x | x |  |  |
| ME04249-06 | x | x |  | x |
| ME04249-07 | x | x |  |  |
| ME04249-08 | x | x |  | x |
| ME04249-09 | x | x |  |  |
| ME04249-10 |  |  |  |  |

Events ME04249-03 and ME04249-07 were evaluated in greater detail in the $T_2$ generation. Eighteen individuals were sown and observed for each event. The transgenic plants showed increased primary inflorescence thickness, increased number of rosette leaves, a larger rosette, and delay of flowering time to a 0.05 level of statistical significance (Table 10). ME04249-07 was also significantly taller than the controls. All plants noted in Table 10 were segregating progeny of the $T_1$ event which had been confirmed to contain the transgene under test. However, all plants noted in the table as -03 or -07 Control were $T_2$ plants which did not contain the transgene under test (internal controls).

In event ME04249-03 all 11 transgene-containing plants exhibited the beneficial phenotypes. Event ME04249-07 had 5 transgene-containing plants which exhibited the beneficial phenotype and 2 transgene-containing plants which appeared wild-type. Our statistical analyses compared the internal controls to those plants with the beneficial phenotype which contained the transgene; all transgene-containing (as confirmed by PCR) but wild-type appearing plants were omitted from the statistical analyses in Table 10.

Segregation frequencies of the transgene under test suggest that each event contains a single insert, as calculated by a Chi-square test.

TABLE 10

Quantitative phenotypes observed in 35S::cDNA 13495746 $T_2$ events

| Event/Control | Number of Observations | Rosette Area (mm$^2$) | Number of Leaves | Height (cm) | Primary Inflorescence Thickness (inches) | Days to Bolt |
|---|---|---|---|---|---|---|
| ME04249-03 | 11 | 3718.4* | 11.0* | 55.9 | 0.060* | 22.7* |
| -03 Control | 7 | 1094.7 | 7.0 | 52.0 | 0.045 | 18.3 |
| ME04249-07 | 5 | 4336.2* | 12.8* | 79.6* | 0.055* | 23.6* |
| -07 Control | 11 | 1787.8 | 6.8 | 47.9 | 0.045 | 17.4 |

*significantly different from control at 0.05 level, via t-test

Summary of Results:

The ectopic expression of cDNA 13495746 with a strong constitutive promoter (35S) results in plants with thicker inflorescences, a larger rosette, and more rosette leaves.

In the events studied, the increase in plant size seen by this expression is accompanied by a delay in flowering time, but no reduction in fertility.

As a result, this gene/protein is especially useful for controlling the rate of cell divisions in meristems without disturbing overall plant morphology. It can be used in crops with an appropriate promoter to regulate size and growth rate of many individual organs. The protein may be used for creating sturdier stems in corn and preventing "snap". Increased vegetative biomass gives an improved source:sink ratio and improved fixation of carbon to sucrose and starch.

EXAMPLE 5

Lead 50; ME07495-03; ME07495-05; Ceres cDNA 12420535; Clone 2835

Eight independently transformed events were selected and evaluated for their qualitative phenotype in the $T_1$ generation as per standard protocol. Two events showing the most advantageous $T_1$ phenotypes were chosen for evaluation in the $T_2$ generation. The $T_2$ growth conditions follow the above $T_1$ protocol. The experimental design differs from the $T_1$ planting in that each $T_2$ plant is contained within its own pot and no herbicide selection is used. All pots for each $T_2$ event are contained within the same flat, and the plants are randomly distributed within each flat. The controls for each set of measurements are the segregating progeny of the given $T_1$ event which do not contain the T-DNA (internal controls). All analyses are done via soil-based experiments under long daylight conditions (16 hours) in the Ceres greenhouse.

This transgene produced a qualitative increase in overall plant size/biomass in 6 of 8 events with no fertility defects. These plants appeared to be delayed in flowering time by several days (Table 11). The transgenic "control" was a set of plants expressing a different 35S:cDNA fusion and were indistinguishable from the untransformed Ws wildtype.

TABLE 11

Qualitative phenotypes observed in 35S::cDNA 12420535 $T_1$ events (all mutant phenotypes were equivalent, so the 2 highlighted events were randomly chosen for $T_2$ analyses).

| Event | Increase in overall plant size/biomass, delayed flowering time |
|---|---|
| ME07495-01 | X |
| ME07495-02 | X |
| ME07495-03 | X |
| ME07495-04 | X |
| ME07495-05 | X |
| ME07495-06 | X |
| ME07495-07 |   |
| ME07495-08 |   |

Events ME07495-03 and ME07495-05 were evaluated in greater detail in the $T_2$ generation. Eighteen individuals for both events were sown and analyzed. Segregation frequencies of the plants under test suggest that each event contains a single insert, as calculated by a Chi-square test.

After detailed $T_2$ analyses, the following observations were determined regarding the transgenics (results below noted with a "*" are statistically significant to a 0.05 level or better via t-test unless otherwise noted):

Flowering time (days to bolt) was approximately 6 days later than controls.

Rosette leaf number at bolting was increased by approximately 3-4 leaves.

Rosette area was approximately 3.5 times larger than controls.

Height was increased approximately 20% (12 cm).

Primary inflorescence thickness was increased approximately 30%.

Details can be found in Tables 12-13.

TABLE 12

Quantitative phenotypes observed in 35S::cDNA 12420535 $T_2$ plants.

| Event/Control | Number of Observations | Day to Bolt | Number of Leaves | Rosette Area (mm$^2$) | Height (cm) |
|---|---|---|---|---|---|
| ME07495-03 | 13 | 30.1* | 11.7* | 4757.4* | 61* |
| -03 Control | 5 | 24 | 7.4 | 1434.5 | 46.8 |
| ME07495-05 | 10 | 30.9* | 11.1* | 4001.9* | 57.1* |
| -05 Control | 8 | 24.4 | 8.4 | 1077.8 | 47.4 |

*significantly different from control at 0.05 level, via t-test

TABLE 13

Quantitative phenotypes observed in 35S::cDNA 12420535 $T_2$ plants.

| Event/Control | Number of Observations | Primary Inflorescence Thickness (mm) | Number of Inflorescences |
|---|---|---|---|
| ME07495-03 | 13 | 1.464* | 6* |
| -03 Control | 5 | 0.996 | 3.2 |
| ME07495-05 | 10 | 1.69* | 6 |
| -05 Control | 8 | 1.16 | 5.25 |

*significantly different from control at 0.05 level, via t-test

Summary of Results:

The ectopic expression of cDNA 12420535 with a strong constitutive promoter (35S) results in taller plants with thicker inflorescences, larger rosettes, and more rosette leaves.

The increase in plant size seen by this expression is accompanied by a delay in flowering time but no reduction in fertility.

As a result, this gene/sequence can provide Increased vegetative biomass to give an improved source:sink ratio to improve yield. Taller inflorescences give the opportunity for more flowers and, therefore, more seeds. The combination of improved biomass and inflorescence stature can give a significant improvement in yield. Thicker inflorescences can prevent "snap" caused by wind, rain, or drought.

EXAMPLE 6

Lead 58; ME07957-01, 02 and -06; Ceres cDNA 1241656; Clone 235672

Ten independently transformed events were selected and evaluated for their qualitative phenotype in the $T_1$ generation as per standard protocol. Three events showing the most advantageous $T_1$ phenotypes were chosen for evaluation in the $T_2$ generation. The $T_2$ growth conditions follow the above $T_1$ protocol. The experimental design differs from the $T_1$ planting in that each $T_2$ plant is contained within its own pot and no herbicide selection is used. All pots for each $T_2$ event are contained within the same flat, and the plants are randomly distributed within each flat. The controls for each set of measurements are the segregating progeny of the given T$_1$ event which do not contain the T-DNA (internal controls). All analyses are done via soil-based experiments under long daylight conditions (16 hours) in the greenhouse.

This transgene produced an increase in overall plant size/biomass in 9 of 10 events with no fertility defects. These plants appeared to be delayed in flowering time by several days (Table 14). The transgenic "control" was a set of plants expressing a different 35S::cDNA fusion and were indistinguishable from the untransformed Ws wildtype (this method of scoring phenotypes is typical for our large-scale morphological phenotyping project).

TABLE 14

Qualitative phenotypes observed in 35S::cDNA 12414656 T$_1$ events (all mutant phenotypes were equivalent, so the 3 highlighted events were randomly chosen for T$_2$ analyses).

| Event | Increase in overall plant size/biomass, delayed flowering time |
|---|---|
| ME07957-01 | x |
| ME07957-02 | x |
| ME07957-03 | |
| ME07957-04 | x |
| ME07957-05 | x |
| ME07957-06 | x |
| ME07957-07 | x |
| ME07957-08 | x |
| ME07957-09 | x |
| ME07957-10 | x |

Events ME07957-01, ME07957-02, and ME07957-06 were evaluated in greater detail in the T$_2$ generation. Eighteen individuals for each event were sown and analyzed. Segregation frequencies of the plants under test suggest that each event contains a single insert, as calculated by a Chi-square test.

After detailed T$_2$ analyses, we determined the following regarding the transgenics (results below noted with a "*" are statistically significant to a 0.05 level or better via t-test unless otherwise noted):

Flowering time (days to bolt) was approximately 10 days later than controls.
Rosette leaf number at bolting was increased by approximately 10 leaves.
Rosette area was approximately 4.7 times larger than controls.
Height was increased approximately 20% (12 cm).
Primary inflorescence thickness was increased approximately 12%.
Inflorescence number increased by approximately 2.1 more branches than controls.
Details can be found in Tables 15-16.

TABLE 15

Quantitative phenotypes observed in 35S::cDNA 12414656 T$_2$ plants.

| Event/Control | Number of Observations | Day to Bolt | Number of Leaves | Rosette Area (mm$^2$) | Height (cm) |
|---|---|---|---|---|---|
| ME07957-01 | 12 | 31.8* | 17.1* | 9086.5* | 59.0* |
| -01 Control | 6 | 21.5 | 8.0 | 1670.9 | 45.5 |
| ME07957-02 | 10 | 31.0* | 16.4* | 8404.7* | 59.7* |
| -02 Control | 8 | 21.4 | 7.6 | 2022.8 | 47.3 |
| ME07957-06 | 12 | 32.0* | 18.6* | 10312.9* | 60.1* |
| -06 Control | 6 | 21.5 | 7.8 | 2278.6 | 50.5 |

*significantly different from control at 0.05 level, via t-test

TABLE 16

Quantitative phenotypes observed in 35S::cDNA 12414656 T$_2$ plants.

| Event/Control | Number of Observations | Primary Inflorescence Thickness (mm) | Number of Inflorescences |
|---|---|---|---|
| ME07957-01 | 12 | 1.50* | 8.2* |
| -01 Control | 6 | 1.34 | 6.0 |
| ME07957-02 | 10 | 1.57* | 8.3* |
| -02 Control | 8 | 1.42 | 5.8 |
| ME07957-06 | 12 | 1.63* | 7.3* |
| -06 Control | 6 | 1.40 | 5.7 |

*significantly different from control at 0.05 level, via t-test

Summary of Results:

The mis-expression of cDNA 12414656 with a strong constitutive promoter (35S) results in taller plants with thicker inflorescences, larger rosettes, and more rosette leaves.

The increase in plant size seen by this expression is accompanied by a delay in flowering time but no reduction in fertility.

Since TxP experiments show that this gene is up-regulated under drought and SA application, this gene may be useful for stress tolerance.

As a result, this cDNA 12414656 can be used to increase vegetative biomass to give an improved source:sink ratio and improve yield. Taller inflorescences give the opportunity for more flowers and, therefore, more seeds. The combination of improved biomass and inflorescence stature can give a significant improvement in yield. Thicker inflorescences can prevent "snap" caused by wind, rain, or drought. This gene/protein can be especially useful for controlling the number/rate of cell divisions in meristems without disturbing overall plant morphology and could be developed in crops with an appropriate promoter to regulate size and growth rate of many individual organs.

EXAMPLE 7

Determination of Functional Homolog Sequences

The "Lead" sequences described in above Examples 1-6 are utilized to identify functional homologs of the lead sequences and, together with those sequences, are utilized to determine a consensus sequence for a given group of lead and functional homolog sequences.

A subject sequence is considered a functional homolog of a query sequence if the subject and query sequences encode proteins having a similar function and/or activity. A process known as Reciprocal BLAST (Rivera et al, *Proc. Natl Acad. Sci. USA*, 1998, 95:6239-6244) is used to identify potential functional homolog sequences from databases consisting of all available public and proprietary peptide sequences, including NR from NCBI and peptide translations from Ceres clones.

Before starting a Reciprocal BLAST process, a specific query polypeptide is searched against all peptides from its source species using BLAST in order to identify polypeptides having sequence identity of 80% or greater to the query polypeptide and an alignment length of 85% or greater along the shorter sequence in the alignment. The query polypeptide and any of the aforementioned identified polypeptides are designated as a cluster.

The main Reciprocal BLAST process consists of two rounds of BLAST searches; forward search and reverse search. In the forward search step, a query polypeptide sequence, "polypeptide A," from source species $S^A$ is BLASTed against all protein sequences from a species of interest. Top hits are determined using an E-value cutoff of $10^{-5}$ and an identity cutoff of 35%. Among the top hits, the sequence having the lowest E-value is designated as the best hit, and considered a potential functional homolog. Any other top hit that had a sequence identity of 80% or greater to the best hit or to the original query polypeptide is considered a potential functional homolog as well. This process is repeated for all species of interest.

In the reverse search round, the top hits identified in the forward search from all species are used to perform a BLAST search against all protein or polypeptide sequences from the source species $S^A$. A top hit from the forward search that returned a polypeptide from the aforementioned cluster as its best hit is also considered as a potential functional homolog.

Functional homologs are identified by manual inspection of potential functional homolog sequences.

The present invention further encompasses nucleotides that encode the above described polypeptides, as well as the complements thereof, and including alternatives thereof based upon the degeneracy of the genetic code.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

REFERENCES (1) Zhang et al. (2004) *Plant Physiol.* 135:615.
(2) Salomon et al. (1984) *EMBO J.* 3:141.
(3) Herrera-Estrella et al. (1983) *EMBO J.* 2:987.
(4) Escudero et al. (1996) *Plant J.* 10:355.
(5) Ishida et al. (1996) *Nature Biotechnology* 14:745.
(6) May et al. (1995) *Bio/Technology* 13:486)
(7) Armaleo et al. (1990) *Current Genetics* 17:97.
(8) Smith. T. F. and Waterman, M. S. (1981) *Adv. App. Math.* 2:482.
(9) Needleman and Wunsch (1970) *J. Mol. Biol.* 48:443.
(10) Pearson and Lipman (1988) *Proc. Natl. Acad. Sci.* (*USA*) 85: 2444.
(11) Yamauchi et al. (1996) *Plant Mol. Biol.* 30:321-9.
(12) Xu et al. (1995) *Plant Mol. Biol.* 27:237.
(13) Yamamoto et al. (1991) *Plant Cell* 3:371.
(14) P. Tijessen, "Hybridization with Nucleic Acid Probes" In Laboratory Techniques in Biochemistry and Molecular Biology, P. C. vand der Vliet, ed., c. 1993 by Elsevier, Amsterdam.
(15) Bonner et al., (1973) *J. Mol. Biol.* 81:123.
(16) Sambrook et al., Molecular Cloning: A Laboratory Manual, Second Edition, Cold Spring Harbor Laboratory Press, 1989, New York.
(17) Shizuya et al. (1992) *Proc. Natl. Acad. Sci. USA*, 89: 8794-8797.
(18) Hamilton et al. (1996) *Proc. Natl. Acad. Sci. USA*, 93: 9975-9979.
(19) Burke et al. (1987) *Science*, 236:806-812.
(20) Sternberg N. et al. (1990) *Proc Natl Acad Sci USA.*, 87:103-7.
(21) Bradshaw et al. (1995) *Nucl Acids Res*, 23: 4850-4856.
(22) Frischauf et al. (1983) *J. Mol Biol*, 170: 827-842.
(23) Huynh et al., Glover N M (ed) DNA Cloning: A practical Approach, Vol. 1 Oxford: IRL Press (1985).
(24) Walden et al. (1990) *Mol Cell Biol* 1: 175-194.
(25) Vissenberg et al. (2005) *Plant Cell Physiol* 46:192.
(26) Husebye et al. (2002) *Plant Physiol* 128:1180.
(27) Plesch et al. (2001) *Plant J.* 28:455.
(28) Weising et al. (1988) *Ann. Rev. Genet.*, 22:421.
(29) Christou (1995) *Euphytica*, v. 85, n.1-3:13-27.
(30) Newell (2000)
(31) Griesbach (1987) *Plant Sci.* 50:69-77.
(32) Fromm et al. (1985) *Proc. Natl. Acad Sci USA* 82:5824.
(33) Paszkowski et al. (1984) *EMBO J.* 3:2717.
(34) Klein et al. (1987) *Nature* 327:773.
(35) Willmitzer, L. (1993) Transgenic Plants. In: iotechnology, A Multi-Volume Comprehensive treatise (H. J. Rehm, G. Reed, A. Püler, P. Stadler, eds., Vol. 2, 627-659, VCH Weinheim-New York-Basel-Cambridge).
(36) *Crit. Rev. Plant. Sci.* 4:1-46.
(37) Fromm et al. (1990) *Biotechnology* 8:833-844.
(38) Cho et al. (2000) *Planta* 210:195-204.
(39) Brootghaerts et al. (2005) *Nature* 433:629-633.
(40) Lincoln et al. (1998) *Plant Mol. Biol. Rep.* 16:1-4.
(41) Lacomme et al. (2001), "Genetically Engineered Viruses" (C. J. A. Ring and E. D. Blair, Eds). Pp. 59-99, BIOS Scientific Publishers, Ltd. Oxford, UK.

What is claimed is:

1. A method of increasing plant size, vegetative growth, plant biomass and/or modulated plant architecture, said method comprising:
   a) introducing into a plant cell a vector construct, said vector construct comprising:
      a first nucleotide sequence that is a regulatory sequence which causes transcription in a plant; and
      a second nucleotide sequence encoding an amino acid sequence that is at least 85% identical to SEQ ID NO:17
      wherein said first and second nucleotide sequences are operably linked,
   b) generating from said plant cell a transformed plant in which said second nucleotide sequence is overexpressed; and
   c) selecting from a plurality of said transformed plants a plant having increased plant size, vegetative growth, biomass and/or modulated plant architecture as compared to a control plant that does not comprise said nucleic acid.

2. The method of claim 1, wherein said transformed plant has an increase in the level of plant size, vegetative growth, organ number and/or biomass.

3. The method of claim 1, wherein said regulatory region is a promoter selected from the group consisting of YP0092 (SEQ ID NO:68), PT0676 (SEQ ID NO:42), PT0708 (SEQ ID NO:47), PT0613 (SEQ ID NO:35), PT0672 (SEQ ID NO:41), PT0678 (SEQ ID NO:43), PT0688 (SEQ ID NO:45), PT0837 (SEQ ID NO:54), the napin promoter, the Arcelin-5 promoter, the phaseolin gene promoter, the soybean trypsin inhibitor promoter, the ACP promoter, the stearoyl-ACP desaturase gene, the soybean .alpha.[1] subunit of .beta.-conglycinin promoter, the oleosin promoter, the 15 kD zein promoter, the 16 kD zein promoter, the 19 kD zein promoter, the 22 kD zein promoter, the 27 kD zein promoter, the Osgt-1 promoter, the beta-amylase gene promoter, and the barley hordein gene promoter.

4. The method of claim 1, wherein said regulatory region is a promoter selected from the group consisting of p326 (SEQ ID NO:106), YP0144 (SEQ ID NO:85), YP0190 (SEQ ID NO:89), p13879 (SEQ ID NO:105), YP0050 (SEQ ID NO:65), p32449 (SEQ ID NO:107), YP0158 (SEQ ID NO:87), YP0214 (SEQ ID NO:91), YP0380 (SEQ ID NO:100), PT0848 (SEQ ID NO:56), and PT0633 (SEQ ID NO:37), the cauliflower mosaic virus (CaMV) 35S promoter, the mannopine synthase (MAS) promoter, the 1' or 2' promoters derived from T-DNA of Agrobacterium tumefaciens, the figwort mosaic virus 34S promoter, actin promoters such as the rice actin promoter, and ubiquitin promoters such as the maize ubiquitin-1 promoter.

5. The method of claim 1, wherein said regulatory region is a promoter selected from the group consisting of ribulose-1, 5-bisphosphate carboxylase (RbcS) promoters such as the RbcS promoter from eastern larch (Larix laricina), the pine cab6 promoter the Cab-1 gene promoter from wheat, the CAB-1 promoter from spinach, the cabIR promoter from rice, the pyruvate orthophosphate dikinase (PPDK) promoter from corn, the tobacco Lhcb1*2 promoter, the *Arabidopsis thaliana* SUC2 sucrose-H+ symporter promoter, and thylakoid membrane protein promoters from spinach (psad, psaF, psaE, PC, FNR, atpC, atpD, cab, rbcS, PT0535 (SEQ ID NO:33), PT0668 (SEQ ID NO:32), PT0886 (SEQ ID NO:59), PRO924 (SEQ ID NO:108), YP0144 (SEQ ID NO:85), YP0380 (SEQ ID NO:100) and PT0585 (SEQ ID NO:34).

6. A plant cell comprising a vector construct, said vector construct comprising:
   a) a first nucleotide sequence that is a regulatory sequence which causes transcription in a plant; and
   b) a second nucleotide sequence encoding an amino acid sequence that is at least 85% identical to SEQ ID NO:17;
wherein said first nucleotide sequence is operatively linked to said second nucleotide sequence and overexpression of said second nucleotide sequence causes a plant generated from the plant cell to possess increased plant size, vegetative growth, biomass and/or modulated plant architecture as compared to a control plant that does not comprise said vector construct.

7. A transgenic plant comprising the plant cell of claim 6.

8. Progeny of the plant of claim 7, wherein said progeny contains said vector construct and has increased plant size, vegetative growth, biomass and/or modulated plant architecture as compared to a control plant that does not comprise said nucleic acid.

9. Seed from a transgenic plant according to claim 7, wherein said seed contains said vector construct.

10. Vegetative tissue from a transgenic plant according to claim 7.

11. A food product comprising vegetative tissue from a transgenic plant according to claim 7.

12. A feed product comprising vegetative tissue from a transgenic plant according to claim 7.

13. A product comprising vegetative tissue from a transgenic plant according to claim 7 used for the conversion into fuel or chemical feedstocks.

14. A method for promoting increased biomass in a plant, comprising:
   (a) transforming a plant with a nucleic acid molecule comprising a nucleotide sequence encoding SEQ ID NO: 17 and
   (b) expressing said nucleotide sequence in said transformed plant, whereby said transformed plant has an increased biomass as compared to a plant that has not been transformed with said nucleotide sequence.

15. A method for increasing the biomass of a plant, said method comprising altering the level of expression in said plant of a nucleic acid molecule according to claim 1.

16. The method according to claim 1, wherein said second nucleotide sequence encodes the amino acid sequence of SEQ ID NO:17.

17. The method according to claim 16, wherein said second nucleotide sequence is the sequence set forth in SEQ ID NO:16.

18. The plant cell of claim 6, wherein said second nucleotide sequence encodes the amino acid sequence of SEQ ID NO:17.

19. The plant cell of claim 18, wherein said second nucleotide sequence is the sequence set forth in SEQ ID NO:16.

20. A plant comprising a vector construct, said vector construct comprising:
   (a) a first nucleotide sequence that is a regulatory sequence which causes transcription in a plant; and
   (b) a second nucleotide sequence encoding an amino acid sequence that is at least 85% identical to SEQ ID NO:17,
wherein said first and second nucleotide sequences are operably linked and wherein said plant is produced by a process comprising:
   (1) introducing into a plant cell said vector construct;
   (2) generating from said plant cell a transformed plant in which said second nucleotide sequence is overexpressed; and
   (3) selecting from a plurality of said transformed plants a plant having increased plant size, vegetative growth, biomass and/or modulated plant architecture as compared to a control plant that does not comprise said overexpressed second nucleotide sequence.

21. The plant according to claim 20, wherein said second nucleotide sequence encodes an amino acid sequence according to SEQ ID NO:17.

* * * * *

SEQUENCE LISTING

```
<160> NUMBER OF SEQ ID NOS: 109

<210> SEQ ID NO 1
<211> LENGTH: 1014
<212> TYPE: DNA
<213> ORGANISM: Arabidopsis thaliana
<220> FEATURE:
<221> NAME/KEY: misc_feature
<222> LOCATION: (1)..(1014)
<223> OTHER INFORMATION: Ceres CLONE ID no. 8161
```

```
<220> FEATURE:
<221> NAME/KEY: CDS
<222> LOCATION: (112)..(766)
<223> OTHER INFORMATION: Referenced by SEQ ID NO: 2

<400> SEQUENCE: 1
ctctctctct taaagctctc ttctttggct ctttcgaaga agaaccattt ttatttccta      60
agagagacga cggagttctt ttctaaagca ccggagagga ggagaagcaa cgatggagaa     120
tgattgcacg gtgaatattg tctctctgga aaggatcgc gatgtttcgg aggcgtcggc     180
tgaatctcag agcgagtcga ctcttcgaa ctcgctcgat tccggtgtta cggctgagac     240
ctctcgttct gatgctgatt ccaaactgga tgaatgtact gcttggacga atgagaaaca     300
caactcatat cttgattatt tagagagctc gtttgttagg caattatact ccttgcttgg     360
aggtgggact cagagacttt ctagaactcg tgatgtgcag tctaactctc ataaatcagc     420
tgatcagttt accgtcctac aaaatggttg ctggcagaag gttaactttg gaaagaaaca     480
atcttgtttg gagacttcat ctgagtttcg ttttcacaga aattcattga aaataagcc     540
tgaaaattcc aacggaaatt acaccatggg aactactgtc caaggagatg tgttatgtca     600
tgacgaaacc aaacactcag aggcgtcagg gcagaatttc agagaagaag aagaagaaga     660
agagaaggga gaggtgagca aaaaacgaga agagaagca aataacgatg atagttcatt     720
gaaggaggat caggttgtgc cggtaaggat ggtgaagccc agaacgtgaa agcattagga     780
agtgtagatg aaatactatg aatagagata aagaaataga agaaggtgtg gttacgaatg     840
tggagagggt tttgtttgtt gtatagcgtg aggctaaaga gagccttcct tataaaggga     900
tccaatggga tatggaaata ggattggtgt ttgttttcgt taaatttgt ctaatgttaa     960
ctaggggaaa agttatctga tagtattagc atcttatggc aattttattc tttt         1014

<210> SEQ ID NO 2
<211> LENGTH: 218
<212> TYPE: PRT
<213> ORGANISM: Arabidopsis thaliana

<400> SEQUENCE: 2

Met Glu Asn Asp Cys Thr Val Asn Ile Val Ser Leu Glu Lys Asp Arg
1               5                   10                  15

Asp Val Ser Glu Ala Ser Ala Glu Ser Gln Ser Glu Ser Thr Leu Ser
            20                  25                  30

Asn Ser Leu Asp Ser Gly Val Thr Ala Glu Thr Ser Arg Ser Asp Ala
        35                  40                  45

Asp Ser Lys Leu Asp Glu Cys Thr Ala Trp Thr Asn Glu Lys His Asn
    50                  55                  60

Ser Tyr Leu Asp Tyr Leu Glu Ser Ser Phe Val Arg Gln Leu Tyr Ser
65                  70                  75                  80

Leu Leu Gly Gly Gly Thr Gln Arg Leu Ser Arg Thr Arg Asp Val Gln
                85                  90                  95

Ser Asn Ser His Lys Ser Ala Asp Gln Phe Thr Val Leu Gln Asn Gly
            100                 105                 110

Cys Trp Gln Lys Val Asn Phe Gly Lys Lys Gln Ser Cys Leu Glu Thr
        115                 120                 125

Ser Ser Glu Phe Arg Phe His Arg Asn Ser Leu Arg Asn Lys Pro Glu
    130                 135                 140

Asn Ser Asn Gly Asn Tyr Thr Met Gly Thr Thr Val Gln Gly Asp Val
145                 150                 155                 160
```

```
Leu Cys His Asp Glu Thr Lys His Ser Glu Ala Ser Gly Gln Asn Phe
            165                 170                 175

Arg Glu Glu Glu Glu Glu Lys Gly Glu Val Ser Lys Lys Arg
        180                 185                 190

Glu Arg Glu Ala Asn Asn Asp Asp Ser Ser Leu Lys Gly Asp Gln Val
    195                 200                 205

Val Pro Val Arg Met Val Lys Pro Arg Thr
    210                 215
```

```
<210> SEQ ID NO 3
<211> LENGTH: 960
<212> TYPE: DNA
<213> ORGANISM: Arabidopsis thaliana
<220> FEATURE:
<221> NAME/KEY: misc_feature
<222> LOCATION: (1)..(960)
<223> OTHER INFORMATION: Ceres CLONE ID no. 8490
<220> FEATURE:
<221> NAME/KEY: CDS
<222> LOCATION: (76)..(817)
<223> OTHER INFORMATION: Referenced by SEQ ID NO: 4

<400> SEQUENCE: 3
atttttgttt ctctctttct ctctgatatt tttcattttc ttcttcttct ctctctctct    60
ccacaaagat aagccaacaa tggttggtga ttacagagga cgctttagta gccgtcgttt   120
ctccgatgac tctgacgatt cttccgacga tgcttcttcc gtggagggag agaccacttc   180
ttccatgtac tctgcgggga aagagtatat ggaaacagaa tggactaatg agaagcatag   240
tttatatctt aaatctatgg aagcttcatt cgtagatcag ttatataact cgctcggagc   300
tctcgggaag aacgagaatg tatccgaatc aacgaggttc ggtagcggta aaaaccgtc   360 tcaagaacag ttcaaggttc ttcatgatgg tttctggcag aagattaatg tgaaacaacc   420
tgaacatcgg attaacggaa ggcacggtgg taattctcat gagtttctta ggagtccatg   480
gattaagcat tataaacctt tagtaaagac acaaatcccg gtaacggatg agcccgaaaa   540
tcaagttgtt agcagctcta atgggaagaa gggaatatgc agctctggct cagcctctag   600
tctcaagcag ctaagctctc attcgcgtga ccacgaccaa atcagcgttg agaagcaga   660 ggtatcggat cagaactttg ttaacgaagg aataaaaggc gaaaacgaa gctcgaagaa   720 gatgaagacg gtgatgatga gtgaatcgtc gagtaccgat caggttgttc cactcaataa   780
actcttgcaa catgacgtaa atttgaagtc tgtttcttga gaggtcagat ggtgaagctt   840
tatatgagga gagaattttg taatgtatat atatttgcat aacttataag tcaaatatac   900
tatccttagt tacaagtttc ttcatcatat atccctaact ataaatatat ttatatgccc   960
```

```
<210> SEQ ID NO 4
<211> LENGTH: 246
<212> TYPE: PRT
<213> ORGANISM: Arabidopsis thaliana

<400> SEQUENCE: 4

Met Val Gly Asp Tyr Arg Gly Arg Phe Ser Ser Arg Arg Phe Ser Asp
1               5                   10                  15

Asp Ser Asp Asp Ser Ser Asp Asp Ala Ser Ser Val Glu Gly Glu Thr
            20                  25                  30

Thr Ser Ser Met Tyr Ser Ala Gly Lys Glu Tyr Met Glu Thr Glu Trp
        35                  40                  45

Thr Asn Glu Lys His Ser Leu Tyr Leu Lys Ser Met Glu Ala Ser Phe
    50                  55                  60
```

```
Val Asp Gln Leu Tyr Asn Ser Leu Gly Ala Leu Gly Lys Asn Glu Asn
 65                  70                  75                  80

Val Ser Glu Ser Thr Arg Phe Gly Ser Gly Arg Lys Pro Ser Gln Glu
                 85                  90                  95

Gln Phe Lys Val Leu His Asp Gly Phe Trp Gln Lys Ile Asn Val Lys
            100                 105                 110

Gln Pro Glu His Arg Ile Asn Gly Arg His Gly Asn Ser His Glu
            115                 120                 125

Phe Leu Arg Ser Pro Trp Ile Lys His Tyr Lys Pro Leu Val Lys Thr
        130                 135                 140

Gln Ile Pro Val Thr Asp Glu Pro Glu Asn Gln Val Val Ser Ser Ser
145                 150                 155                 160

Asn Gly Lys Lys Gly Ile Cys Ser Ser Gly Ser Ala Ser Ser Leu Lys
                165                 170                 175

Gln Leu Ser Ser His Ser Arg Asp His Asp Gln Ile Ser Val Gly Glu
            180                 185                 190

Ala Glu Val Ser Asp Gln Asn Phe Val Asn Glu Gly Ile Lys Gly Glu
        195                 200                 205

Asn Gly Ser Ser Lys Lys Met Lys Thr Val Met Met Ser Glu Ser Ser
210                 215                 220

Ser Thr Asp Gln Val Val Pro Leu Asn Lys Leu Leu Gln His Asp Val
225                 230                 235                 240

Asn Leu Lys Ser Val Ser
                245
```

<210> SEQ ID NO 5
<211> LENGTH: 792
<212> TYPE: DNA
<213> ORGANISM: Oryza sativa subsp. indica
<220> FEATURE:
<221> NAME/KEY: misc_feature
<222> LOCATION: (1)..(792)
<223> OTHER INFORMATION: GDNA ANNOT ID no. 1443850
<220> FEATURE:
<221> NAME/KEY: misc_feature
<222> LOCATION: (1)..(792)
<223> OTHER INFORMATION: CDNA ID no. 37078836

<400> SEQUENCE: 5

```
atgcaaaaat cccgagaaga gaggcaaaac gatgccgtaa agaaagtga aagtcgaacg      60
agatcagaaa cgtctgggtt aactggtcac gagtcagtcg agttggctca attacaggat   120
tcaccgatga tagaatccat gtcttcagaa tggacagatg agaagcacaa actttatctt   180
aaatccatgg aggcttcatt tgttaatcaa ttatacaatt cgatagatct tcttggttgg   240
cgttcccaga aggggaggcc agttccaaac ttgtctgggg aagtcaattg tagcacctgt   300
agaccttctg ccagtttaa ggttcttcga cgtggcggct ggcagaaaat caattttcga   360
agacatgaat ctcaactaag ctcagcgaag gactcccgtg gtatttaac aagcccatgg   420
attcaacaat ttacgcctgc aagaaaacca gaaggtgcaa catctcctgc tcttcaagaa   480
tgtgctatcc aaagtcgagg aatcaattta agtggaaga aagcagttct ctgctgtcca   540
gcaactaatt caaactttc tcattttggc aactcttttt catgtcatcg tgatttcgtt   600
gaaagcaaca cagagatgtc aggccagaac tttgttgacg aagacatcga aagtgaaagt   660
gcaagcagtt ctttcagctc aaaaaggttt aaaactctga aactgatcc ttcgagtagt   720
gaccaggttg ttccccacag caagactcct gtggaagaag aggttactga gtgtatttct   780
```

```
gcagctaaat aa                                                            792
```

<210> SEQ ID NO 6
<211> LENGTH: 263
<212> TYPE: PRT
<213> ORGANISM: Oryza sativa subsp. indica
<220> FEATURE:
<221> NAME/KEY: misc_feature
<222> LOCATION: (1)..(263)
<223> OTHER INFORMATION: GDNA ANNOT ID no. 1443850
<220> FEATURE:
<221> NAME/KEY: misc_feature
<222> LOCATION: (1)..(263)
<223> OTHER INFORMATION: CDNA ID no. 37078836

<400> SEQUENCE: 6

Met Gln Lys Ser Arg Glu Glu Arg Gln Asn Asp Ala Val Lys Glu Ser
1               5                   10                  15

Glu Ser Arg Thr Arg Ser Glu Thr Ser Gly Leu Thr Gly His Glu Ser
            20                  25                  30

Val Glu Leu Ala Gln Leu Gln Asp Ser Pro Met Ile Glu Ser Met Ser
        35                  40                  45

Ser Glu Trp Thr Asp Glu Lys His Lys Leu Tyr Leu Lys Ser Met Glu
    50                  55                  60

Ala Ser Phe Val Asn Gln Leu Tyr Asn Ser Ile Asp Leu Leu Gly Trp
65                  70                  75                  80

Arg Ser Gln Lys Gly Arg Pro Val Pro Asn Leu Ser Gly Glu Val Asn
                85                  90                  95

Cys Ser Thr Cys Arg Pro Ser Gly Gln Phe Lys Val Leu Arg Arg Gly
            100                 105                 110

Gly Trp Gln Lys Ile Asn Phe Arg Arg His Glu Ser Gln Leu Ser Ser
        115                 120                 125

Ala Lys Asp Ser Arg Gly Tyr Leu Thr Ser Pro Trp Ile Gln Gln Phe
    130                 135                 140

Thr Pro Ala Arg Lys Pro Glu Gly Ala Thr Ser Pro Ala Leu Gln Glu
145                 150                 155                 160

Cys Ala Ile Gln Ser Arg Gly Ile Asn Leu Lys Trp Lys Lys Ala Val
                165                 170                 175

Leu Cys Cys Pro Ala Thr Asn Ser Lys Leu Ser His Phe Gly Asn Ser
            180                 185                 190

Phe Ser Cys His Arg Asp Phe Val Glu Ser Asn Thr Glu Met Ser Gly
        195                 200                 205

Gln Asn Phe Val Asp Glu Asp Ile Glu Ser Glu Ser Ala Ser Ser Ser
    210                 215                 220

Phe Ser Ser Lys Arg Leu Lys Thr Leu Lys Thr Asp Pro Ser Ser Ser
225                 230                 235                 240

Asp Gln Val Val Pro His Ser Lys Thr Pro Val Glu Glu Val Thr
                245                 250                 255

Glu Cys Ile Ser Ala Ala Lys
            260

<210> SEQ ID NO 7
<211> LENGTH: 759
<212> TYPE: DNA
<213> ORGANISM: Arabidopsis thaliana
<220> FEATURE:
<221> NAME/KEY: misc_feature
<222> LOCATION: (1)..(759)
<223> OTHER INFORMATION: GDNA ANNOT ID no. 1496794
<220> FEATURE:

```
<221> NAME/KEY: misc_feature
<222> LOCATION: (1)..(759)
<223> OTHER INFORMATION: Ceres CDNA ID no. 37078800

<400> SEQUENCE: 7
atgcaaaaat cccgagaaga gaggcaaaac gatgccgtaa agaaagtga aagtcgaacg      60 agatcagaaa cgtctgggtt aactggtcac gagtcagtcg agttggctca attacaggat    120
tcaccgatga tagaatccat gtcttcagaa tggacagatg agaagcacaa actttatctt    180
aaatccatgg aggcttcatt tgttaatcaa ttatacaatt cgatagatct tcttggttgg    240
cgttcccaga aggggaggcc agttccaaac ttgtctgggg aatttaaggt tcttcgacgt    300
ggcggctggc agaaaatcaa ttttcgaaga catgaatctc aactaagctc agcgaaggac    360
tcccgtgggt atttaacaag cccatggatt caacaattta cgcctgcaag aaaaccagaa    420
ggtgcaacat ctcctgctct tcaagaatgt gctatccaaa gtcgaggaat caatttaaag    480
tggaagaaag cagttctctg ctgtccagca actaattcaa actttctca ttttggcaac     540 tcttttcat gtcatcgtga tttcgttgaa agcaacacag atgtcagg ccagaacttt       600 gttgacgaag acatcgaaag tgaaagtgca agcagttctt tcagctcaaa aaggttgaaa    660
actctgaaaa ctgatccttc gagtagtgac caggttgttc cccacagcaa gactcctgtg    720
gaagaagagg ttactgagtg tatttctgca gctaaataa                            759
```

```
<210> SEQ ID NO 8
<211> LENGTH: 252
<212> TYPE: PRT
<213> ORGANISM: Arabidopsis thaliana
<220> FEATURE:
<221> NAME/KEY: misc_feature
<222> LOCATION: (1)..(252)
<223> OTHER INFORMATION: GDNA ANNOT ID no. 1496794
<220> FEATURE:
<221> NAME/KEY: misc_feature
<222> LOCATION: (1)..(252)
<223> OTHER INFORMATION: Ceres CDNA ID no. 37078800

<400> SEQUENCE: 8

Met Gln Lys Ser Arg Glu Glu Arg Gln Asn Asp Ala Val Lys Glu Ser
1               5                   10                  15

Glu Ser Arg Thr Arg Ser Glu Thr Ser Gly Leu Thr Gly His Glu Ser
            20                  25                  30

Val Glu Leu Ala Gln Leu Gln Asp Ser Pro Met Ile Glu Ser Met Ser
        35                  40                  45

Ser Glu Trp Thr Asp Glu Lys His Lys Leu Tyr Leu Lys Ser Met Glu
    50                  55                  60

Ala Ser Phe Val Asn Gln Leu Tyr Asn Ser Ile Asp Leu Leu Gly Trp
65                  70                  75                  80

Arg Ser Gln Lys Gly Arg Pro Val Pro Asn Leu Ser Gly Glu Phe Lys
                85                  90                  95

Val Leu Arg Arg Gly Gly Trp Gln Lys Ile Asn Phe Arg Arg His Glu
            100                 105                 110

Ser Gln Leu Ser Ser Ala Lys Asp Ser Arg Gly Tyr Leu Thr Ser Pro
        115                 120                 125

Trp Ile Gln Gln Phe Thr Pro Ala Arg Lys Pro Glu Gly Ala Thr Ser
    130                 135                 140

Pro Ala Leu Gln Glu Cys Ala Ile Gln Ser Arg Gly Ile Asn Leu Lys
145                 150                 155                 160

Trp Lys Lys Ala Val Leu Cys Cys Pro Ala Thr Asn Ser Lys Leu Ser
```

```
                165                 170                 175
His Phe Gly Asn Ser Phe Ser Cys His Arg Asp Phe Val Glu Ser Asn
                180                 185                 190

Thr Glu Met Ser Gly Gln Asn Phe Val Asp Glu Asp Ile Glu Ser Glu
        195                 200                 205

Ser Ala Ser Ser Ser Phe Ser Ser Lys Arg Leu Lys Thr Leu Lys Thr
        210                 215                 220

Asp Pro Ser Ser Ser Asp Gln Val Val Pro His Ser Lys Thr Pro Val
225                 230                 235                 240

Glu Glu Glu Val Thr Glu Cys Ile Ser Ala Ala Lys
            245                 250

<210> SEQ ID NO 9
<211> LENGTH: 1153
<212> TYPE: DNA
<213> ORGANISM: Arabidopsis thaliana
<220> FEATURE:
<221> NAME/KEY: misc_feature
<222> LOCATION: (1)..(1153)
<223> OTHER INFORMATION: Ceres CLONE ID no. 37288
<220> FEATURE:
<221> NAME/KEY: CDS
<222> LOCATION: (210)..(975)
<223> OTHER INFORMATION: Referenced by SEQ ID NO: 8

<400> SEQUENCE: 9 agccccttc  ccaatatttg atcaatttct aaagaaaacc ccttcctcta ctagtcctcc    60
tcctatatat acaaaatctt aagaaatctc tctacttgtt tcctctgtta tcataatctc   120
ttctctctat atctcttctc ttcttctttt accctgtttt tttttttcat tccacagagc   180
ccaggttgat tgattttgtt attcagagat atggggagag aaggattga gattaagaag    240 attgagaata tcaacagtcg tcaagtcact ttctctaaga gacgaaacgg tttgatcaag   300
aaggctaaag agctttcgat tctctgtgac gccgaggttg ctcttatcat cttctccagc   360
accggcaaga tttacgattt ctccagcgtc tgtatggagc aaattctttc tagatatgga   420
tacactactg cgtccactga gcataaacaa caaagagaac accaacttct aatttgtgct   480
tcacatggaa atgaagctgt gttgcgaaat gatgattcta tgaaggtgga acttgaaaga   540
ttacagcttg caattgagag acttaagggt aaggagcttg aaggtatgag tttcccggat   600 cttattctt tgaaaaacca gttgaacgag agcttgcata tgtcaagga tcaaaagaca   660 caaatcctgc tcaaccagat tgagagatcc aggatacagg agaaaaagc attggaagaa   720 aaccaaatct tgcgcaaaca ggttgagatg ttggggagag gttcaggacc aaaagtgttg   780
aatgaaaggc ctcaagattc tagcccagaa gccgatcccg agagctcttc atcagaagag   840
gatgagaatg acaacgagga gcaccattcc gacacttcct tgcagttggg gttgtcgtcg   900
acggggtatt gcacaaagag aaagaagccg aagatcgaac tggtctgcga taactctggg   960
agtcaagtgg cttctgattg atggaatcga ttattttct aattctggtt gtttaggggt   1020
ctctatgtgt cttcttgttt ctggctgttc ttttgcttta tttcatctca agtagagttt   1080
tcttaatgtt taggtggaac attttttccat aatcaagaag ggatttgatc aatcaataac   1140
attagatttt ctt                                                      1153

<210> SEQ ID NO 10
<211> LENGTH: 255
<212> TYPE: PRT
<213> ORGANISM: Arabidopsis thaliana
<220> FEATURE:
```

```
<221> NAME/KEY: misc_feature
<222> LOCATION: (81)..(180)
<223> OTHER INFORMATION: Pfam Name: K-box; Pfam Description: K-box
      region
<220> FEATURE:
<221> NAME/KEY: misc_feature
<222> LOCATION: (9)..(59)
<223> OTHER INFORMATION: Pfam Name: SRF-TF; Pfam Description: SRF-type
      transcription factor (DNA-binding and dimerisation domain)

<400> SEQUENCE: 10

Met Gly Arg Gly Arg Ile Glu Ile Lys Lys Ile Glu Asn Ile Asn Ser
 1               5                  10                  15

Arg Gln Val Thr Phe Ser Lys Arg Arg Asn Gly Leu Ile Lys Lys Ala
            20                  25                  30

Lys Glu Leu Ser Ile Leu Cys Asp Ala Glu Val Ala Leu Ile Ile Phe
        35                  40                  45

Ser Ser Thr Gly Lys Ile Tyr Asp Phe Ser Ser Val Cys Met Glu Gln
    50                  55                  60

Ile Leu Ser Arg Tyr Gly Tyr Thr Thr Ala Ser Thr Glu His Lys Gln
65                  70                  75                  80

Gln Arg Glu His Gln Leu Leu Ile Cys Ala Ser His Gly Asn Glu Ala
                85                  90                  95

Val Leu Arg Asn Asp Asp Ser Met Lys Val Glu Leu Glu Arg Leu Gln
            100                 105                 110

Leu Ala Ile Glu Arg Leu Lys Gly Lys Glu Leu Glu Gly Met Ser Phe
        115                 120                 125

Pro Asp Leu Ile Ser Phe Glu Asn Gln Leu Asn Glu Ser Leu His Ser
    130                 135                 140

Val Lys Asp Gln Lys Thr Gln Ile Leu Asn Gln Ile Glu Arg Ser
145                 150                 155                 160

Arg Ile Gln Glu Lys Lys Ala Leu Glu Glu Asn Gln Ile Leu Arg Lys
                165                 170                 175

Gln Val Glu Met Leu Gly Arg Gly Ser Gly Pro Lys Val Leu Asn Glu
            180                 185                 190

Arg Pro Gln Asp Ser Ser Pro Glu Ala Asp Pro Glu Ser Ser Ser Ser
        195                 200                 205

Glu Glu Asp Glu Asn Asp Asn Glu Glu His His Ser Asp Thr Ser Leu
    210                 215                 220

Gln Leu Gly Leu Ser Ser Thr Gly Tyr Cys Thr Lys Arg Lys Lys Pro
225                 230                 235                 240

Lys Ile Glu Leu Val Cys Asp Asn Ser Gly Ser Gln Val Ala Ser

<210> SEQ ID NO 11
<211> LENGTH: 254
<212> TYPE: PRT
<213> ORGANISM: Gossypium hirsutum
<220> FEATURE:
<221> NAME/KEY: misc_feature
<222> LOCATION: (1)..(254)
<223> OTHER INFORMATION: GI no. 52789958

<400> SEQUENCE: 11

Met Gly Arg Gly Lys Ile Glu Ile Lys Arg Ile Glu Asn Ala Asn Ser
 1               5                  10                  15

Arg Gln Val Thr Phe Ser Lys Arg Arg Ala Gly Leu Leu Lys Lys Ala
            20                  25                  30

Lys Glu Leu Ala Ile Leu Cys Asp Ala Glu Val Ala Val Ile Ile Phe
        35                  40                  45
```

```
Ser Asn Thr Gly Lys Leu Phe Glu Phe Ser Ser Gly Met Asn Lys
    50                  55                  60

Thr Ile Ser Arg Tyr Lys Ser Ala Gln Gly Ser Pro Glu Ile Ala Gln
 65                  70                  75                  80

Val Glu His Lys Ala Glu Lys Gln Asp Ser Lys Glu Ala Asp His Leu
                 85                  90                  95

Lys Asp Glu Ile Ala Lys Leu Gln Met Lys Gln Leu Gln Leu Leu Gly
                100                 105                 110

Lys Asn Leu Thr Ser Met Ser Leu Lys Glu Leu Gln Leu Leu Glu Gln
                115                 120                 125

Gln Leu Asn Glu Gly Leu Leu Ser Val Lys Glu Lys Lys Glu Gln Leu
            130                 135                 140

Leu Met Gln Gln Leu Glu Gln Ser Arg Leu Gln Glu Gln Arg Ala Met
145                 150                 155                 160

Leu Glu Asn Glu Thr Leu Arg Arg Gln Val Glu Glu Leu Arg Gly Phe
                165                 170                 175

Phe Pro Thr Thr Asp His Pro Ile Gln Pro Tyr Leu Glu Cys Tyr Pro
                180                 185                 190

Val Glu Arg Lys Asn Ser Leu Met Ser His Ser Ile Pro Ser Pro Asp
                195                 200                 205

Leu Thr Cys Asn Cys Thr Val Glu Lys Gly Asp Ser Asp Thr Thr Leu
                210                 215                 220

Tyr Leu Gly Leu Pro Ser Asp Tyr His Lys Arg Lys Pro Glu Ile
225                 230                 235                 240

Glu Ser His Ser Asn Glu Ser Glu Ser Gln Leu Gly Leu Leu
                245                 250

<210> SEQ ID NO 12
<211> LENGTH: 247
<212> TYPE: PRT
<213> ORGANISM: Glycine max
<220> FEATURE:
<221> NAME/KEY: misc_feature
<222> LOCATION: (1)..(247)
<223> OTHER INFORMATION: Ceres CLONE ID no. 523628

<400> SEQUENCE: 12

Met Gly Arg Gly Lys Ile Glu Ile Lys Lys Ile Glu Asn Leu Asn Ser
 1               5                  10                  15

Arg Gln Val Thr Phe Ser Lys Arg Arg Asn Gly Leu Leu Lys Lys Ala
                 20                  25                  30

Lys Glu Leu Ser Val Leu Cys Asp Ala Glu Val Ala Val Ile Ile Phe
             35                  40                  45

Ser Ser Thr Gly Lys Leu Tyr Glu Phe Ser Asn Thr Ser Met Glu His
    50                  55                  60

Thr Leu Ser Arg Tyr Ser Lys Gly Ala Glu Ser Asp Ser Ala Glu Gln
 65                  70                  75                  80

Pro Ile Asp Val Pro Pro Thr Asp Val Met Ala Val Glu Pro Asp Thr
                 85                  90                  95

Asn Leu Leu Met Glu Glu Ile Thr Lys Leu Arg Ser Ala Tyr Leu Arg
                100                 105                 110

Met Met Gly Lys Glu Leu Asp Gly Leu Ser Leu Lys Asp Leu Gln Gln
            115                 120                 125

Leu Glu Asn Gln Leu Ser Glu Gly Met Gln Ser Val Lys Asp Lys Lys
        130                 135                 140
```

Glu Gln Val Leu Val Glu Gln Leu Arg Lys Ser Arg Ile Gln Glu Gln
145                 150                 155                 160

Lys Ala Met Leu Glu Asn Val Leu Arg Lys Gln Leu Glu Glu Ile
                165                 170                 175

Gln Asn Lys Thr Lys Ser Gln Phe Leu Glu Phe Ser Ser Leu Asp Arg
            180                 185                 190

Thr Phe Ser Lys Asn Gly Ser Lys Ser Leu Phe Asn Cys Ala Ser Glu
            195                 200                 205

Glu Asn Asp Leu Ser Asp Thr Ser Leu Gln Leu Gly Leu Ser Thr Asp
            210                 215                 220

Tyr Gly Arg Gln Arg Lys Ala Leu Lys Met Glu Pro Cys Asn Asp Ser
225                 230                 235                 240

Gly Ser Gln Val Ala Ser His
                245

<210> SEQ ID NO 13
<211> LENGTH: 269
<212> TYPE: PRT
<213> ORGANISM: Petunia x hybrida
<220> FEATURE:
<221> NAME/KEY: misc_feature
<222> LOCATION: (1)..(269)
<223> OTHER INFORMATION: GI no. 34452081

<400> SEQUENCE: 13

Met Gly Arg Gly Lys Ile Asp Ile Lys Leu Ile Glu Asn Val Asn Asn
1               5                   10                  15

Arg Gln Val Thr Phe Ser Lys Arg Arg Ala Gly Leu Leu Lys Lys Ala
                20                  25                  30

Asn Glu Leu Ser Val Leu Cys Asp Ala Glu Val Ala Val Ile Ile Phe
            35                  40                  45

Ser Ser Thr Gly Lys Leu Phe Glu Phe Ser Ser Thr Ser Met Lys Gln
    50                  55                  60

Thr Leu Ser Arg Tyr Asn Arg Cys Leu Ala Ser Thr Glu Thr Ser Ala
65                  70                  75                  80

Ile Glu Lys Lys Leu Glu Asp Asn Glu Gln Pro Gln Pro Leu Gln Thr
                85                  90                  95

Tyr Val Pro Lys Gln Glu Gln Lys Glu Met Asp Ile Leu Lys Asp Glu
            100                 105                 110

Leu Ser Lys Leu Lys Met Asp Gln Leu Arg Leu Leu Gly Lys Asp Leu
        115                 120                 125

Ser Gly Met Gly Leu Asn Glu Leu Arg Leu Leu Glu His Gln Leu Asn
    130                 135                 140

Glu Gly Leu Leu Ala Ile Lys Asp Arg Lys Glu Glu Leu Leu Ile Gln
145                 150                 155                 160

Gln Leu Glu Gln Ser Arg Arg Gln Glu Glu Arg Ala Ala Leu Glu Ser
                165                 170                 175

Glu Thr Leu Arg Arg Gln Leu Glu Glu Leu Arg Gly Leu Phe Pro Leu
            180                 185                 190

Ser Thr Ser Leu Pro Pro Pro Tyr Leu Glu Tyr His Pro Leu Glu Gln
        195                 200                 205

Lys Tyr Pro Ile Leu Lys Glu Gly Glu Ser Leu Asp Ser Asp Thr
    210                 215                 220

Ala Cys Glu Asp Gly Val Asp Asp Glu Asp Ser Asn Thr Thr Leu Gln
225                 230                 235                 240

Leu Gly Leu Pro Ile Val Gly Arg Lys Arg Lys Lys Pro Glu Gln Asp

```
                        245                 250                 255
Ser Pro Ser Ser Asn Ser Glu Asn Gln Val Gly Ser Lys
            260                 265

<210> SEQ ID NO 14
<211> LENGTH: 265
<212> TYPE: PRT
<213> ORGANISM: Brassica napus
<220> FEATURE:
<221> NAME/KEY: misc_feature
<222> LOCATION: (1)..(265)
<223> OTHER INFORMATION: Ceres CLONE ID no. 1251169

<400> SEQUENCE: 14

Met Asp Arg Gly Lys Ile Glu Ile Lys Arg Ile Glu Asn Ala Asn Ser
1               5                   10                  15

Arg Gln Val Thr Phe Ser Lys Arg Arg Ala Gly Leu Leu Lys Lys Ala
            20                  25                  30

His Glu Leu Ser Val Leu Cys Asp Ser Glu Val Ala Val Ile Val Phe
        35                  40                  45

Ser Lys Ser Gly Lys Leu Phe Glu Phe Ser Ser Thr Gly Met Lys Arg
50                  55                  60

Thr Val Leu Arg Tyr Glu Asn Tyr Gln Arg Ser Ser Asp Ala Pro Leu
65                  70                  75                  80

Ile Lys Tyr Lys Pro Glu Asn Gln Glu Asp Cys Thr Glu Val Asp
                85                  90                  95

Phe Leu Lys Asn Glu Ile Ser Lys Leu Gln Glu Lys His Leu Gln Met
            100                 105                 110

Gln Gly Lys Gly Leu Asn Ala Leu Cys Leu Lys Glu Leu Gln His Leu
        115                 120                 125

Glu Gln Gln Leu Asn Val Ser Leu Ile Ser Val Arg Glu Arg Lys Glu
130                 135                 140

Leu Leu Leu Thr Lys Gln Ile Glu Glu Ser Arg Ile Arg Glu Gln Arg
145                 150                 155                 160

Ala Glu Leu Glu Asn Glu Thr Leu Arg Arg Gln Val Gln Glu Leu Arg
                165                 170                 175

Asn Phe Leu Pro Ser Ile Asn Gln Asn Tyr Val Pro Ser Tyr Ile Thr
            180                 185                 190

Cys Phe Ala Ile Asp Pro Lys Asn Ser Pro Val Asn Asn Ser Gly Leu
        195                 200                 205

Asp Asp Thr Asn Tyr Ser Leu Gln Lys Thr Asn Ser Asp Thr Thr Leu
210                 215                 220

Gln Leu Gly Leu Pro Gly Glu Ala Gln Ala Arg Arg Ser Glu Ala
225                 230                 235                 240

Asn Arg Glu Ser Pro Ser Ser Asp Ser Val Thr Thr Ser Thr Thr Lys
                245                 250                 255

Ala Thr Pro Gln Arg Ile Asn Leu Val
            260                 265

<210> SEQ ID NO 15
<211> LENGTH: 235
<212> TYPE: PRT
<213> ORGANISM: Zea mays
<220> FEATURE:
<221> NAME/KEY: misc_feature
<222> LOCATION: (1)..(235)
<223> OTHER INFORMATION: Ceres CLONE ID no. 244916

<400> SEQUENCE: 15
```

```
Met Val Gly Thr Gly Lys Arg Glu Arg Ile Ala Ile Arg Ile Asp
1               5                   10                  15

Asn Leu Ala Ala Arg Gln Val Thr Phe Ser Lys Arg Arg Gly Leu
                20                  25                  30

Phe Lys Lys Ala Glu Glu Leu Ser Ile Leu Cys Asp Ala Glu Val Gly
            35                  40                  45

Leu Val Val Phe Ser Ala Thr Gly Lys Leu Phe His Phe Ala Ser Ser
    50                  55                  60

Ser Met Lys Gln Val Ile Asp Arg Tyr Asp Ser His Ser Lys Thr Leu
65                  70                  75                  80

Gln Arg Ser Glu Pro Gln Ser Ser Gln Leu Gln Ser His Met Asp Asp
                85                  90                  95

Gly Thr Cys Ala Arg Leu Lys Glu Glu Leu Ala Glu Thr Ser Leu Lys
            100                 105                 110

Leu Arg Gln Met Arg Gly Glu Glu Leu Gln Arg Leu Ser Val Glu Gln
            115                 120                 125

Leu Gln Glu Leu Glu Lys Thr Leu Glu Ser Gly Leu Gly Ser Val Leu
130                 135                 140

Lys Thr Lys Ser Gln Lys Ile Leu Asp Glu Ile Ser Gly Leu Glu Arg
145                 150                 155                 160

Lys Arg Thr Arg Leu Ile Glu Glu Asn Ser Arg Leu Lys Glu Gln Leu
                165                 170                 175

Gln Val Thr Arg Met Ser Arg Met Glu Thr Gln Leu Gly Ala Asp Pro
            180                 185                 190

Glu Phe Val Tyr Glu Glu Gly Gln Ser Ser Glu Ser Val Thr Asn Thr
            195                 200                 205

Ser Tyr Pro Arg Pro Ser Thr Asp Thr Asp Cys Ser Asp Thr Ser
210                 215                 220

Leu Arg Leu Gly Leu Pro Leu Phe Ser Ser Lys
225                 230                 235
```

<210> SEQ ID NO 16
<211> LENGTH: 640
<212> TYPE: DNA
<213> ORGANISM: Arabidopsis thaliana
<220> FEATURE:
<221> NAME/KEY: misc_feature
<222> LOCATION: (1)..(640)
<223> OTHER INFORMATION: Ceres CLONE ID no. 2835
<220> FEATURE:
<221> NAME/KEY: CDS
<222> LOCATION: (96)..(516)
<223> OTHER INFORMATION: Referenced by SEQ ID NO: 15

<400> SEQUENCE: 16

```
tgaacaccga atctctcaac acaaacaaaa tcacacatct ctcttcatct ttttgtttcc      60
tgcaagaatc tgaatctgct ttactattgt gtcatcatga tgaacatcga cgatacgacg    120
tctccaatgg cccacccgat cggtccatct cagcctcctt ccgaccaaac caaacaagat    180
ccgccaagtt tgcccaaga agcagcttct tctgtttcgg ccgacaagaa agatctagct    240
ttgcttgaag agaaaccgaa gcagagtcaa gaagaagata gagtggacac tgggagagag    300
aggttaaaga agcatcggag agagatcgct ggtagggttt ggataccgga gatatgggga    360
caagaagagc ttcttaagga ttggatcgat tgttcaacgt tgacacgtg tctagtccct    420
gccggaatct cgtctgcacg tactgctctc gtagaggaag ctaggcgagc tgcttcagct    480
tctggtgggt tacataatcg ttgcttgatc ttacgttgaa tttaatataa taagataaca    540
```

```
tacttataaa tgtggttctt gttcctcaat aatataaggc actattgtta cattgttgat    600
aatattctaa ctcattttac tcgtaacttt atgaaacatt                          640
```

```
<210> SEQ ID NO 17
<211> LENGTH: 140
<212> TYPE: PRT
<213> ORGANISM: Arabidopsis thaliana

<400> SEQUENCE: 17
```

Met Met Asn Ile Asp Asp Thr Thr Ser Pro Met Ala His Pro Ile Gly
1               5                   10                  15

Pro Ser Gln Pro Pro Ser Asp Gln Thr Lys Gln Asp Pro Pro Ser Leu
            20                  25                  30

Pro Gln Glu Ala Ala Ser Ser Val Ser Ala Asp Lys Lys Asp Leu Ala
        35                  40                  45

Leu Leu Glu Glu Lys Pro Lys Gln Ser Gln Glu Glu Asp Arg Val Asp
50                  55                  60

Thr Gly Arg Glu Arg Leu Lys Lys His Arg Arg Glu Ile Ala Gly Arg
65                  70                  75                  80

Val Trp Ile Pro Glu Ile Trp Gly Gln Glu Glu Leu Leu Lys Asp Trp
                85                  90                  95

Ile Asp Cys Ser Thr Phe Asp Thr Cys Leu Val Pro Ala Gly Ile Ser
            100                 105                 110

Ser Ala Arg Thr Ala Leu Val Glu Glu Ala Arg Arg Ala Ala Ser Ala
        115                 120                 125

Ser Gly Gly Leu His Asn Arg Cys Leu Ile Leu Arg
    130                 135                 140

```
<210> SEQ ID NO 18
<211> LENGTH: 126
<212> TYPE: PRT
<213> ORGANISM: Brassica napus
<220> FEATURE:
<221> NAME/KEY: misc_feature
<222> LOCATION: (1)..(126)
<223> OTHER INFORMATION: Ceres CLONE ID no. 1085655

<400> SEQUENCE: 18
```

Met Lys Asn Ile Asp Asp Thr Thr Ser Pro Met Thr Arg Val Ile Asp
1               5                   10                  15

Pro Ser Gln Pro Pro Ser Asp Gln Ser Gln Gln Glu Pro Ser Leu Thr
            20                  25                  30

Asn Glu Ala Ser Ser Val Ser Asp Lys Lys Asp Gln Ala Leu Pro Glu
        35                  40                  45

Glu Lys Pro Lys Gln Asn Gln Glu Asn Glu Arg Ala Val Thr Gly Arg
50                  55                  60

Glu Lys Leu Lys His His Arg Arg Glu Met Ala Gly Arg Val Trp Ile
65                  70                  75                  80

Pro Glu Ile Trp Gly Gln Glu Glu Leu Leu Lys Asp Trp Ile Asp Cys
                85                  90                  95

Ser Thr Phe Asp Thr Cys Leu Val Pro Asn Gly Ile Ser Ser Ala Arg
            100                 105                 110

Ala Ala Leu Val Glu Glu Ala Arg Arg Ala Ala Ser Ala Ser
        115                 120                 125

```
<210> SEQ ID NO 19
<211> LENGTH: 135
```

```
<212> TYPE: PRT
<213> ORGANISM: Brassica napus
<220> FEATURE:
<221> NAME/KEY: misc_feature
<222> LOCATION: (1)..(135)
<223> OTHER INFORMATION: Ceres CLONE ID no. 1087946
<220> FEATURE:
<221> NAME/KEY: misc_feature
<222> LOCATION: (7)..(7)
<223> OTHER INFORMATION: Xaa is any aa, unknown, or other

<400> SEQUENCE: 19

Met Leu His Phe Ser Trp Xaa Met Lys Asn Ile Asp Asp Thr Thr Ser
1               5                   10                  15

Pro Met Thr His Leu Ile Asn Pro Ser Gln Pro Ser Asp Lys Thr
            20                  25                  30

Gln Gln Asp Pro Ser Leu Ser Thr Glu Ala Cys Ile Val Ser Asp Lys
        35                  40                  45

Lys Asp Gln Ala Leu Pro Glu Glu Lys Pro Lys Gln Asn Gln Glu Ala
    50                  55                  60

Ile Ile Gly Arg Asp Lys Leu Lys Gln His Arg Arg Glu Met Ala Gly
65                  70                  75                  80

Arg Val Trp Ile Pro Glu Arg Trp Gly Gln Glu Asp Leu Leu Lys Asp
                85                  90                  95

Trp Ile Asp Cys Ser Lys Phe Asp Thr Cys Leu Val Pro Asn Gly Ile
            100                 105                 110

Ser Ser Ala Arg Ser Ala Leu Val Glu Glu Ala Arg Arg Ala Ala Ser
        115                 120                 125

Ala Ser Gly Gly Leu His Asn
    130                 135

<210> SEQ ID NO 20
<211> LENGTH: 180
<212> TYPE: PRT
<213> ORGANISM: Glycine max
<220> FEATURE:
<221> NAME/KEY: misc_feature
<222> LOCATION: (1)..(180)
<223> OTHER INFORMATION: Ceres CLONE ID no. 635536

<400> SEQUENCE: 20

Met Lys Glu Lys Thr Leu Ser Met Ala His Gln Tyr Ser Ser Ser Asn
1               5                   10                  15

Glu Ser Asp Ser Gln Ile Ile Pro Pro Gln Pro Phe Lys Leu Lys Lys
            20                  25                  30

Pro His Gln Pro Lys Gly Lys Gln Met Gly Gln Glu Gln Glu Asn Glu
        35                  40                  45

Ser Gln Tyr Leu Glu Glu Leu Val Ser Asp Ser Arg Pro Arg Lys Tyr
    50                  55                  60

Ser Gly Lys Asp Asn Asn Asn Ile Leu Gly Gln Ile Pro Ser Ala Ser
65                  70                  75                  80

Lys Ile His Asn Lys Val Glu Ile Ala Leu Asp His Asn Ala Thr Lys
                85                  90                  95

Glu Gly Ile Thr Ser Val Glu Gly Asp His Gln Asp Ser Gly Arg Glu
            100                 105                 110

Lys Leu Lys Arg His Arg Val Glu Val Ala Gly Arg Val Trp Ile Pro
        115                 120                 125

Asp Ile Trp Gly Gln Glu Glu Ile Leu Lys Asp Trp Ile Asp Cys Thr
    130                 135                 140
```

```
Ala Phe Asp Ala Pro Leu Val Pro Ser Arg Ile Val Met Arg Thr
145                 150                 155                 160

Ala Leu Val Glu Glu Gly Arg Arg Ala Thr Ser Gly Gly Leu Arg Ile
            165                 170                 175

Glu Asn Arg Cys
            180

<210> SEQ ID NO 21
<211> LENGTH: 1025
<212> TYPE: DNA
<213> ORGANISM: Zea mays
<220> FEATURE:
<221> NAME/KEY: misc_feature
<222> LOCATION: (1)..(1025)
<223> OTHER INFORMATION: Ceres CLONE ID no. 235672
<220> FEATURE:
<221> NAME/KEY: misc_feature
<222> LOCATION: (321)..(321)
<223> OTHER INFORMATION: n is a, c, t, g, unknown, or other
<220> FEATURE:
<221> NAME/KEY: CDS
<222> LOCATION: (114)..(580)
<223> OTHER INFORMATION: Referenced by SEQ ID NO: 22

<400> SEQUENCE: 21
acagagcgcc acgaggcgag cagtcgagtg ttccctagag tccccgttcc tccgccgccg      60
cctgcaaccg cttcacgtgc cctgatccat cgcaggtccc ctttctgacc ccaaatggag     120
ccgaagaagt cctctgctca gcaccagccc cacgccatgg aacccaagaa gtcctctcca     180
cgcggcgccg gggccgtcgc cgccaccgcc actgaagccg agtccccgtt gagcagcttg     240
ttctacccgc cggcgcccgc ggcaaatggg aaagatcagg agttgtacag cattatttac     300
aaagggcaga gcgggagcgc nacaagctgg cgcgacaggt aatggtaaac cgcaatgggc     360
tccttccaaa agtcataccg cgtacgcaaa ggacggtaaa cattcaccac cttatgatac     420
gtcatgtttt gggtcatctg tgcattatgg tggtcgagat tatttctacg gcagctctac     480
aaccaagaaa gcgacagaat cctccactga ctacaaaggg gacaagaaag atccagtcgc     540
agattctcat ggcgactggt ggcaaggctc attttattac taagagaacc tggtggcctc     600
tccttggaga acaaggaaca gaaggagggg cagtgaagct cggtttcctt gattgctagc     660
agtattatct tgtgtcatag tggacccgct ttcgtccagt ggtggtgcgc caatatttag     720
aagcgtcacc tggcctgggc agatgtagtg tgcgtcttat agtctctgct ttagatgtgc     780
aatgtaacga agctttagca cagtatgaac tagaccgcat aaaagaatcc atgtccattc     840
cgccagtaat atgagcgggt tggtatctga ctccttagag tcaaaattct gtacaattgg     900
atcgtcgctc caaagcaaaa aaaaaaaaca ataataatgt gctggagaag cggcgatgac     960
ttcacattgt acacctttac cagctggaat ttgacagaag tttggaaact gttcttgtca    1020
attgc                                                                1025

<210> SEQ ID NO 22
<211> LENGTH: 155
<212> TYPE: PRT
<213> ORGANISM: Zea mays

<400> SEQUENCE: 22

Met Glu Pro Lys Lys Ser Ser Ala Gln His Gln Pro His Ala Met Glu
1               5                   10                  15

Pro Lys Lys Ser Ser Pro Arg Gly Ala Gly Ala Val Ala Ala Thr Ala
            20                  25                  30
```

```
Thr Glu Ala Glu Ser Pro Leu Ser Ser Leu Phe Tyr Pro Pro Ala Pro
            35                  40                  45

Ala Ala Asn Gly Lys Asp Gln Glu Leu Tyr Ser Ile Ile Tyr Lys Gly
 50                  55                  60

Gln Ser Gly Ser Ala Gln Ala Gly Ala Thr Gly Asn Gly Lys Pro Gln
 65                  70                  75                  80

Trp Ala Pro Ser Lys Ser His Thr Ala Tyr Ala Lys Asp Gly Lys His
                 85                  90                  95

Ser Pro Pro Tyr Asp Thr Ser Cys Phe Gly Ser Val His Tyr Gly
            100                 105                 110

Gly Arg Asp Tyr Phe Tyr Gly Ser Thr Thr Lys Ala Thr Glu
            115                 120                 125

Ser Ser Thr Asp Tyr Lys Gly Asp Lys Lys Asp Pro Val Ala Asp Ser
130                 135                 140

His Gly Asp Trp Trp Gln Gly Ser Phe Tyr Tyr
145                 150                 155

<210> SEQ ID NO 23
<211> LENGTH: 156
<212> TYPE: PRT
<213> ORGANISM: Oryza sativa subsp. japonica
<220> FEATURE:
<221> NAME/KEY: misc_feature
<222> LOCATION: (1)..(156)
<223> OTHER INFORMATION: GI no. 56784045

<400> SEQUENCE: 23

Met Glu Pro Lys Arg Ser Pro Ala Leu Pro Gln Pro Asn Val Glu Thr
 1               5                  10                  15

Lys Lys Ser Pro Pro Arg Ala Ala Gly Gly Gly Gly Gly Thr
             20                  25                  30

Ala Ala Val Gly Gly Glu Ser Pro Leu Ser Ser Leu Phe His Gln Pro
             35                  40                  45

Ser His Gly Ala Lys Gly Lys Glu Asp Ile Tyr Ser Ile Phe Tyr Lys
 50                  55                  60

Gly Gln Asn Gly Thr Ala Gln Ala Gly Thr Ala Asp Gly Lys Ser Gln
 65                  70                  75                  80

Trp Thr Pro Pro Lys Ser Arg Thr Val Tyr Thr Lys Asp Asn Lys Gln
                 85                  90                  95

Ser Asn Gln Tyr Asp Ser Val Asp Thr Ser Cys Phe Gly Ser Ser Val
            100                 105                 110

Asn Tyr Gly Gly Arg Asp Tyr Tyr Gly Ile Ser Gly His Lys Gln Ser
            115                 120                 125

Thr Glu Ser Asn Asp Tyr Lys Ala Asp Lys Lys Asp Pro Ser Thr Asp
130                 135                 140

Ser His Gly Asp Trp Trp Gln Gly Ser Phe Tyr Tyr
145                 150                 155

<210> SEQ ID NO 24
<211> LENGTH: 137
<212> TYPE: PRT
<213> ORGANISM: Zea mays
<220> FEATURE:
<221> NAME/KEY: misc_feature
<222> LOCATION: (1)..(137)
<223> OTHER INFORMATION: Ceres CLONE ID no. 688400

<400> SEQUENCE: 24

Met Glu Ala Lys Lys Ser Gly Pro Ala Ala Ala Gly Ala Ala Ala Pro
```

```
                1               5                    10                  15
Pro Pro Ala Asn Gly Tyr Phe Ser Thr Val Phe Ser Ala Ser Pro Ala
                    20                  25                  30

Gly Ser Ala Asn Asp Ala Lys Gln Ala Asp Leu Tyr Thr Met Leu Asn
                    35                  40                  45

Lys Gln Thr Ser Arg Gly Gln Asn Gly Ser Gly Ile Thr Asp Gly Lys
    50                  55                  60

Ser His Gly Arg Pro Thr Tyr Lys Asp Gly Lys His Ala Tyr Pro Asn
65                  70                  75                  80

Asp Ser Ser Glu Ser Pro Tyr Phe Gly Ser Val His Tyr Gly Gly
                    85                  90                  95

Arg Glu Phe Tyr Ser Asn Thr Leu Gln Lys Gln Pro Ala Asn Glu Pro
                    100                 105                 110

Gln Thr Lys Tyr Lys Glu Asp Lys Pro Asp Gly Ser Ala Thr Arg Gly
            115                 120                 125

Asp Trp Trp Gln Gly Ser Leu Tyr Tyr
        130                 135

<210> SEQ ID NO 25
<211> LENGTH: 147
<212> TYPE: PRT
<213> ORGANISM: Triticum aestivum
<220> FEATURE:
<221> NAME/KEY: misc_feature
<222> LOCATION: (1)..(147)
<223> OTHER INFORMATION: Ceres CLONE ID no. 630099

<400> SEQUENCE: 25

Met Asp Ala Lys Lys Arg Ser Pro Pro Ala Pro Ser Ala Ala Gly Ala
1               5                   10                  15

Ala Pro Pro Ala Ala Asn Gly Tyr Phe Asn Ser Val Phe Ser Ala Pro
                    20                  25                  30

Ala Ser Pro Ala Ala Asn Pro Arg Asp Ala Arg Gln Met Asp Leu Tyr
                    35                  40                  45

Thr Ile Leu Asn Lys Gln Asn Pro Lys Gly Gln Ser Gly Gly Gly Ile
    50                  55                  60

Ala Gly Asn Ala Lys Ser His Gly Ser Pro Thr Ile Gly Arg Val Ala
65                  70                  75                  80

Tyr Gln Asp Gly Lys Gln Phe Tyr Pro Asn Glu Ser Ser Glu Ser Pro
                    85                  90                  95

Tyr Phe Gly Ser Ser Val His Tyr Gly Gly Arg Asp Phe Tyr Asp Ser
                    100                 105                 110

Ser Pro His Lys Gln Ala Asp Glu Ser Pro Arg Asn Tyr Lys Glu Asp
            115                 120                 125

Asn Ala Asp Gly Ser Leu Ala Thr Arg Gly Asp Trp Trp Gln Gly Ser
        130                 135                 140

Leu Tyr Tyr
145

<210> SEQ ID NO 26
<211> LENGTH: 568
<212> TYPE: DNA
<213> ORGANISM: Arabidopsis thaliana
<220> FEATURE:
<221> NAME/KEY: misc_feature
<222> LOCATION: (1)..(568)
<223> OTHER INFORMATION: Ceres CLONE ID no. 258241
<220> FEATURE:
<221> NAME/KEY: CDS
```

<222> LOCATION: (70)..(433)
<223> OTHER INFORMATION: Referenced by SEQ ID NO: 25

<400> SEQUENCE: 26

```
aaatcttctt tcctcaatat cacccagaag aaagagaaag tgaaacagat caagaaagag    60
attgagaaaa atgtgtagag gcttgaataa tgaagagagc agaagaagtg acggaggagg   120
ttgccggagt ctctgcacga gaccgagtgt tccggtaagg tgtgagcttt gcgacggaga   180
cgcctccgtg ttctgtgaag cggactcggc gttcctctgt agaaaatgtg accggtgggt   240
tcatggagcg aattttctag cttggagaca cgtaaggcgc gtgctatgca cttcttgtca   300
gaaactcacg cgccggtgcc tcgtcggaga tcatgacttc cacgttgttt taccgtcggt   360
gacgacggtc ggagaaacca ccgtggagaa tagaagtgaa caagataatc atgaggttcc   420
gtttgttttt ctctgattat tagattttt tggtgtaagc tataaatatt ctagggtttt    480
tatgcaattt tcttttaaga aaatctgaa aattttaatt ttatgaagct tagaatttta    540
agaaatgtgt aatgaaaaaa aaaaaga                                      568
```

<210> SEQ ID NO 27
<211> LENGTH: 121
<212> TYPE: PRT
<213> ORGANISM: Arabidopsis thaliana
<220> FEATURE:
<221> NAME/KEY: misc_feature
<222> LOCATION: (28)..(72)
<223> OTHER INFORMATION: Pfam Name: zf-B_box; Pfam Description: B-box zinc finger

<400> SEQUENCE: 27

Met Cys Arg Gly Leu Asn Asn Glu Glu Ser Arg Arg Ser Asp Gly Gly
1               5                   10                  15

Gly Cys Arg Ser Leu Cys Thr Arg Pro Ser Val Pro Val Arg Cys Glu
            20                  25                  30

Leu Cys Asp Gly Asp Ala Ser Val Phe Cys Glu Ala Asp Ser Ala Phe
        35                  40                  45

Leu Cys Arg Lys Cys Asp Arg Trp Val His Gly Ala Asn Phe Leu Ala
    50                  55                  60

Trp Arg His Val Arg Arg Val Leu Cys Thr Ser Cys Gln Lys Leu Thr
65                  70                  75                  80

Arg Arg Cys Leu Val Gly Asp His Asp Phe His Val Val Leu Pro Ser
                85                  90                  95

Val Thr Thr Val Gly Glu Thr Thr Val Glu Asn Arg Ser Glu Gln Asp
            100                 105                 110

Asn His Glu Val Pro Phe Val Phe Leu
        115                 120

<210> SEQ ID NO 28
<211> LENGTH: 117
<212> TYPE: PRT
<213> ORGANISM: Arabidopsis thaliana
<220> FEATURE:
<221> NAME/KEY: misc_feature
<222> LOCATION: (1)..(117)
<223> OTHER INFORMATION: Ceres CLONE ID no. 803247
<220> FEATURE:
<221> NAME/KEY: misc_feature
<222> LOCATION: (82)..(82)
<223> OTHER INFORMATION: Xaa is any aa, unknown, or other
<220> FEATURE:
<221> NAME/KEY: misc_feature
<222> LOCATION: (92)..(92)
<223> OTHER INFORMATION: Xaa is any aa, unknown, or other

```
<220> FEATURE:
<221> NAME/KEY: misc_feature
<222> LOCATION: (101)..(101)
<223> OTHER INFORMATION: Xaa is any aa, unknown, or other
<220> FEATURE:
<221> NAME/KEY: misc_feature
<222> LOCATION: (102)..(102)
<223> OTHER INFORMATION: Xaa is any aa, unknown, or other

<400> SEQUENCE: 28

Met Cys Arg Gly Phe Glu Lys Glu Glu Arg Arg Ser Asp Asn Gly
1               5                   10                  15

Gly Cys Gln Arg Leu Cys Thr Glu Ser His Lys Ala Pro Val Ser Cys
            20                  25                  30

Glu Leu Cys Gly Glu Asn Ala Thr Val Tyr Cys Glu Ala Asp Ala Ala
        35                  40                  45

Phe Leu Cys Arg Lys Cys Asp Arg Trp Val His Ser Ala Asn Phe Leu
    50                  55                  60

Ala Arg Arg His Leu Arg Arg Val Ile Cys Thr Thr Cys Arg Lys Leu
65                  70                  75                  80

Thr Xaa Arg Cys Leu Val Gly Asp Asn Phe Asn Xaa Val Leu Pro Glu
                85                  90                  95

Ile Arg Met Ile Xaa Xaa Ile Glu Glu His Ser Ser Asp His Lys Ile
            100                 105                 110

Pro Phe Val Phe Leu
        115

<210> SEQ ID NO 29
<211> LENGTH: 492
<212> TYPE: DNA
<213> ORGANISM: Arabidopsis thaliana
<220> FEATURE:
<221> NAME/KEY: misc_feature
<222> LOCATION: (1)..(492)
<223> OTHER INFORMATION: GDNA ANNOT ID no. 1488021
<220> FEATURE:
<221> NAME/KEY: misc_feature
<222> LOCATION: (1)..(492)
<223> OTHER INFORMATION: Ceres CDNA ID no. 37167642

<400> SEQUENCE: 29
atgtgtagag gtaatcagga gagaagtaac caaggcagtt cttgtaacaa ggaggctgtt      60
tcacctaatg caacctcaag attcgtttgt tgtgagctat gtggctcgag ggcaacattg     120
tattgtcaag cagatcatgc atttctatgt caaaaatgtg acggatgggt gcatggagct     180
aatttcttag ccctcaggca tgttagaaac atgttatgca acacatgcca aaatcttaca     240
cagagatgtc tcattggggc ttcaactgag gtgatgcttt caactattca tatccaaatt     300
cagagaccac agcagcttta ttcctggaaa gaggagggag acacagacag gataaatggg     360
tggcactttc ctataaaatt ccaagtgaga agtgctttta agcagaagca gcatattcta     420
cacgtcatta acagcagcaa ccatcaacat aaatggcatg acatcacata taggagagat     480
gaagaatggt ag                                                         492

<210> SEQ ID NO 30
<211> LENGTH: 163
<212> TYPE: PRT
<213> ORGANISM: Arabidopsis thaliana
<220> FEATURE:
<221> NAME/KEY: misc_feature
<222> LOCATION: (1)..(163)
<223> OTHER INFORMATION: GDNA ANNOT ID no. 1488021
<220> FEATURE:
```

```
<221> NAME/KEY: misc_feature
<222> LOCATION: (1)..(163)
<223> OTHER INFORMATION: Ceres cDNA ID no. 37167642

<400> SEQUENCE: 30

Met Cys Arg Gly Asn Gln Glu Arg Ser Asn Gln Gly Ser Ser Cys Asn
1               5                   10                  15

Lys Glu Ala Val Ser Pro Asn Ala Thr Ser Arg Phe Val Cys Cys Glu
            20                  25                  30

Leu Cys Gly Ser Arg Ala Thr Leu Tyr Cys Gln Ala Asp His Ala Phe
        35                  40                  45

Leu Cys Gln Lys Cys Asp Gly Trp Val His Gly Ala Asn Phe Leu Ala
    50                  55                  60

Leu Arg His Val Arg Asn Met Leu Cys Asn Thr Cys Gln Asn Leu Thr
65                  70                  75                  80

Gln Arg Cys Leu Ile Gly Ala Ser Thr Glu Val Met Leu Ser Thr Ile
                85                  90                  95

His Ile Gln Ile Gln Arg Pro Gln Gln Leu Tyr Ser Trp Lys Glu Glu
            100                 105                 110

Gly Asp Thr Asp Arg Ile Asn Gly Trp His Phe Pro Ile Lys Phe Gln
        115                 120                 125

Val Arg Ser Ala Phe Lys Gln Lys Gln His Ile Leu His Val Ile Asn
    130                 135                 140

Ser Ser Asn His Gln His Lys Trp His Asp Ile Thr Tyr Arg Arg Asp
145                 150                 155                 160

Glu Glu Trp

<210> SEQ ID NO 31
<211> LENGTH: 1823
<212> TYPE: DNA
<213> ORGANISM: Arabidopsis thaliana
<220> FEATURE:
<221> NAME/KEY: misc_feature
<222> LOCATION: (1)..(1823)
<223> OTHER INFORMATION: Ceres Promoter 21876

<400> SEQUENCE: 31
gtctcttaaa aaggatgaac aaacacgaaa ctggtggatt atacaaatgt cgccttatac      60
atatatcggt tattggccaa aagagctatt ttaccttatg gataatggtg ctactatggt     120
tggagttgga ggtgtagttc aggcttcacc ttctggttta agccctccaa tgggtaatgg     180
taaatttccg gcaaaaggtc ctttgagatc agccatgttt ccaatgttg aggtcttata     240 ttccaagtat gagaaggta aaataaatgc gtttcctata gtggagttgc tagatagtag     300
tagatgttat gggctacgaa ttggtaagag agttcgattt tggactagtc cactcggata     360 cttttttcaat tatggtggtc ctggaggaat ctcttgtgga gtttgatatt tgcgagtata     420
atctttgaac ttgtgtagat tgtacccaaa accgaaaaca tatcctatat aaatttcatt     480
atgagagtaa aattgtttgt tttatgtatc atttctcaac tgtgattgag ttgactattg     540
aaaacatatc ttagataagt ttcgttatga gagttaatga tgattgatga catacacact     600
cctttatgat ggtgattcaa cgttttggag aaaattatt tataatctct cataaattct     660
ccgttattag ttgaataaaa tcttaaatgt ctcctttaac catagcaaac caacttaaaa     720
atttagattt taaagttaag atggatattg tgattcaacg attaattatc gtaatgcata     780
ttgattatgt aaaataaaat ctaactaccg gaatttattc ataactcca ttgtgtgact     840 gcatttaaat atatgtttta tgtcccatta attaggctgt aatttcgatt tatcaattta     900
```

-continued

| | |
|---|---|
| tatactagta ttaatttaat tccatagatt tatcaaagcc aactcatgac ggctagggtt | 960 |
| ttccgtcacc ttttcgatca tcaagagagt ttttttataa aaaaatttat acaattatac | 1020 |
| aatttcttaa ccaaacaaca cataattata agctatttaa catttcaaat tgaaaaaaaa | 1080 |
| aatgtatgag aattttgtgg atccattttt gtaattcttt gttgggtaaa ttcacaacca | 1140 |
| aaaaaataga aaggcccaaa acgcgtaagg gcaaattagt aaaagtagaa ccacaaagag | 1200 |
| aaagcgaaaa ccctagacac ctcgtagcta aagtaccct cgagtcgacc aggattaggg | 1260 |
| tgcgctctca tatttctcac attttcgtag ccgcaagact cctttcagat tcttacttgc | 1320 |
| aggttagata ttttctctct ttagtgtctc cgatcttcat cttcttatga ttattgtagc | 1380 |
| tgtttagggt ttagattctt agtttttagct ctatattgac tgtgattatc gcttattctt | 1440 |
| tgctgttgtt atactgcttt tgattctcta gctttagatc cgtttactcg tcgatcaata | 1500 |
| ttgttcctat tgagtctgat gtataatcct ctgattaatt gatagcgttt agttttgata | 1560 |
| tcgtcttcgc atgtttttta tcatgtcgat ctgtatctgc tctggttata gttgattctg | 1620 |
| atgtatttgg ttggtgatgt tccttagatt tgatatacct gttgtctcgt ggtttgatat | 1680 |
| gatagctcaa ctggtgatat gtggttttgt ttcagtggat ctgtgtttga ttatattgtt | 1740 |
| gacgttttgg ttgttgtatg gttgatggtt gatgtatttt tgttgattct gatgtttcga | 1800 |
| tttttgtttt tgttttgaca gct | 1823 |

<210> SEQ ID NO 32
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0668

<400> SEQUENCE: 32

| | |
|---|---|
| atagagtttt actatgcttt tggaatctttt cttctaatgt gccaactaca gagaaataca | 60 |
| tgtattacca ctaggaatcg gaccatatca tagatatcag gattagataa ctagttctcg | 120 |
| tcgctatcac ttcgcattaa gttctagtaa ttgttaaaga ttctaatttt ttactaaaca | 180 |
| aaaactaaat caacatcaaa tatgcaaagt gtgtgttgtc cacacaagtg actcaaagta | 240 |
| tacgcaggtg ggattggacc atattattgc aaatcgtttc cgaaccactc atatttcttt | 300 |
| ttttctctcc ttttttttatc cggagaatta tggaaccact tcatttcaac ttcaaaacta | 360 |
| attttttggt tcagtgatca aatacaaaaa aaaaaaaaaa gttatagata ttaaatagaa | 420 |
| aactattcca atcttaaaaa tacaaatgaa accataattt taatttatac aaaactattt | 480 |
| aattagctaa gggttgtctt aacgtttaga aaataaaaaa ttatgattgt ctgtttaaaa | 540 |
| ttacaatgaa tgaataaaaa aaatatgcaa tgaatgaaag aataaatttt gtacatccga | 600 |
| tagaatgaga aaatgaattt tgtacaaacc actcaagaat tcaaaacaat tgtcaaagtt | 660 |
| ttcttctcag ccgtgtgtcc tcctctccta gccgccacat ctcacacact aatgctaacc | 720 |
| acgcgatgta accgtaagcg ctgagttttt gcatttcaga tttcacttcc accaaacaaa | 780 |
| actcgccacg tcatcaatac gaatcattcc gtataaacgt ctagattctt tacagcctac | 840 |
| aatgttctct tctttggtcg gccattattt aacgctttga acctaaatct agcccagcca | 900 |
| acgaagaaga cgaagcaaat ccaaaccaaa gttctccatt ttcgtagctt ctttaagctt | 960 |
| tttcagtatc atagagacac ttttttttttt ttgattagaa | 1000 |

<210> SEQ ID NO 33
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0535

<400> SEQUENCE: 33

| | | | | | |
|---|---|---|---|---|---|
| ttagtgaaat | tatgacatta | agtaaggttt | tcttagttag | ctaatgtatg | gctattcaat | 60 |
| tgttatgtta | ggctatttta | gttagtatat | gaatttaggc | agtctatgca | aatgatttcg | 120 |
| ttttcatttt | ttcatatgta | aacatcaaga | tcaagtaacg | ccattcgagt | tgatattttt | 180 |
| tttttaaatt | agtgtgtgta | aattttggac | cgcttatttg | agtttgctaa | tgaagttgca | 240 |
| tatatattac | gttaaaccat | aggcaaacta | atttgaaaca | tccgattcga | tttcctgtaa | 300 |
| tttttcttgg | ttaattgacc | aaaatcaaga | tcttcagaaa | taaaataaaa | gacgaaagaa | 360 |
| agctgtcgca | aagcagattg | tgttaaaaaa | aagtggattg | ggctcaaacg | caacttgtcc | 420 |
| agcccgtgac | aattacccta | tacgcaagta | agagtaacgt | atcactggca | aaagttggta | 480 |
| ttagttacga | tatctttgtc | atgggggcat | gcatgggcat | ggcttaagag | ttaagcctta | 540 |
| agaagagtcc | cacactcgtg | actctcatga | tcacttgttg | tttcttacgg | gcaaatacat | 600 |
| ttaactttat | tcttcattta | ttcacctata | ttcttttgga | taataacttt | tctctatata | 660 |
| aaataacaaa | catcgtacgt | ttcatttatt | tacaacaagc | gatgagaatt | aaaaggagac | 720 |
| cttaattgat | gatactcttc | ttttctctcg | gttacaacgg | gattattaca | gataatgata | 780 |
| atctatatgg | atgctgacgt | ggaaaaacaa | aatttggtga | aacacgtcaa | ttaagcacga | 840 |
| cttttccatg | gctagtggct | aagatcgttt | catcacatgg | ctatatcata | taatacttgg | 900 |
| atgaattcaa | aataaacgac | tgagaaaatg | tccacgtcac | ggcgcaccgc | tttggactta | 960 |
| agtctcctat | aataaataca | acaccaaaca | ttgcattcca | | | 1000 |

<210> SEQ ID NO 34
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter PT0585

<400> SEQUENCE: 34

| | | | | | |
|---|---|---|---|---|---|
| tgaagtcatt | taatatgagt | ttgacattag | gtaaacctaa | tctatgagat | tatagaatgt | 60 |
| agcaaaacta | tcaatgtttc | ttttccaaaa | tattttgtgg | tttttctttt | tggttcatta | 120 |
| tgttttgtta | tttgtgaatt | attttaatat | gaagtaatta | tattgatttt | atatgatata | 180 |
| catattattt | tgatataaaa | tttaacactt | atccattaaa | atagcatggg | cataatcaaa | 240 |
| atcgggacta | ttacgatgaa | aaagatagtt | aaattgtatg | ataaaataaa | atgtgtaaga | 300 |
| ttaaaatttt | gggttttaga | aaattactaa | acaaaatata | gacaaagtat | gttgactatt | 360 |
| atttaaaatt | taaatatcat | caataagata | tagttaaagt | cattaagtgt | atagcaaaat | 420 |
| gaaaattcta | agattaaaat | tcgattaaaa | ttttttttac | taaattaaat | atttaaaaat | 480 |
| agggattatc | atttactatt | tacaattcta | atatcatggg | taaaaattga | taactttttt | 540 |
| taaacccgcc | tatctaggtg | ggcctaacct | agttactaaa | ttactatatg | attaacttat | 600 |
| taccactttt | acttcttctt | ttttggtcaa | attactttat | tgtttttat | aaagtcaaat | 660 |

```
tactctttgc attgtaaata atagtagtaa ctaaaatctt aaaacaaaat attcaacctt      720
tcccattatt ggaatggtaa tgtcttcaac accattgacc aacgttaagg aatgtctttt      780 aatattttg gaacctaaat gctaatactg tataccacaa tcacttatga gtattgaagt       840
tgagatagag gaggtacaag gagaccttat ctgcagaaga caaaaagcca ttttagcaa       900 aactaaagaa agaaaaaaga ttgaaacaca aatatgcgcc actcgtagtc caccccctatc    960 tctttggcaa aagccacttc actcttttc ccttttat                              999

<210> SEQ ID NO 35
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0613

<400> SEQUENCE: 35
ttaatactaa cattgtagaa agccacaaaa aagaaattga aatgtgagta gatgctgagt      60
cagaggtttg gtcaatacac aacagctaat tgagataata ttatacacgt cacgatgact      120
tgttttttct cctcccaact tgttaatttc tttattctta aaattaaacc atcgcaaaaa      180
cagaagaaca cagctgtttt tctcgactcc caatttctat tttgctgcta aggacatttc      240
atttcattat ttcccaattc aggactcctt agattttcct aaatttgttt tcctaacttg      300
ctctctctca ttctaacatt ttctcatttt tttagattat cttgtacttt ttagtagatt      360
attttatcag gttttacaaa catacattga cattctaaaa agggcttcta aaaattcagt      420
gtggaatgct gatatactaa aaaaaggtca tgcaaaatta tctacgattt atctaaaatt      480 agataaatttg ccatatataa ctattaacta ataatcgatc ctttgatttt ttgtttagat     540
aaaacgaaac agctatatct ttttttttg ttatcggatt ttaatcgaat aaaagctgaa      600
aaataacagt tatatcttct tctttttaa ctaatgaaac agttatatct taaacaaaca      660
acagaaacag taaatatta atgcaaatcc gcgtcaagag ataaatttta acaaactaat      720
aacaattgag ataagattag cgcaaaagaa actctaattt tagagcgtgt aaacacaaac     780
acgtcttgaa agtaaacgtg aattacacgc ttctaaaacg agcgtgagtt ttggttataa     840
cgaagatacg gtgaagtgtg acacctttct acgttaattt cagtttgagg acacaactca    900
agttatgttt gatatctaag gacttgcact gtctccaaat ctgcaggaag gacttttga     960 ttggatcaat ataaatacca tctccattct cgtctccttc                           1000

<210> SEQ ID NO 36
<211> LENGTH: 351
<212> TYPE: DNA
<213> ORGANISM: Arabidopsis thaliana
<220> FEATURE:
<221> NAME/KEY: misc_feature
<222> LOCATION: (1)..(351)
<223> OTHER INFORMATION: Ceres Promoter PT0625

<400> SEQUENCE: 36
gatcatgatc agtttcaact cgctgtgccc acgtgtcgag agatcggcac gtgcctgagc      60
tctcagccgc tcataaatac acttgtttag tagcaacagt atactatagt agtcctctcc     120
tgtttggctt ttagcttgca tcgatggatg gatggatgga tcgcatgaga gggcttcgcg     180
aaggtacgga accttacaca acgcgtgtcc tttctacgtg gccatcgtgt aggcgtctcg     240
```

-continued ccatgctacg tgtcccggag gatgtctcga tgccaaccct tataaatact gttccattcc   300
aatcccatcg ccacagccag tgcaaatctg atcgatcaag ataatcgagc a           351

<210> SEQ ID NO 37
<211> LENGTH: 1022
<212> TYPE: DNA
<213> ORGANISM: Arabidopsis thaliana
<220> FEATURE:
<221> NAME/KEY: misc_feature
<222> LOCATION: (1)..(1022)
<223> OTHER INFORMATION: Ceres Promoter PT0633

<400> SEQUENCE: 37
cccgatcggc cttaatctga gtcctaaaaa ctgttatact taacagttaa cgcatgattt    60
gatggaggag ccatagatgc aattcaatca aactgaaatt tctgcaagaa tctcaaacac   120
ggagatctca aagtttgaaa gaaaatttat ttcttcgact caaaacaaac ttacgaaatt   180
taggtagaac ttatatacat tatattgtaa ttttttgtaa caaaatgttt ttattattat   240
tatagaattt tactggttaa attaaaaatg aatagaaaag gtgaattaag aggagagagg   300
aggtaaacat tttcttctat tttttcatat tttcaggata aattattgta aaagtttaca   360
agatttccat ttgactagtg taaatgagga atattctcta gtaagatcat tatttcatct   420
acttctttta tcttctacca gtagaggaat aaacaatatt tagctccttt gtaaatacaa   480
attaattttc gttcttgaca tcattcaatt ttaattttac gtataaaata aaagatcata   540
cctattagaa cgattaagga gaaatacaat tcgaatgaga aggatgtgcc gtttgttata   600
ataaacagcc acacgacgta aacgtaaaat gaccacatga tgggccaata gacatggacc   660
gactactaat aatagtaagt tacattttag gatggaataa atatcatacc gacatcagtt   720
tgaaagaaaa gggaaaaaaa gaaaaaataa ataaaagata tactaccgac atgagttcca   780
aaaagcaaaa aaaagatca agccgacaca gacacgcgta gagagcaaaa tgactttgac   840
gtcacaccac gaaaacagac gcttcatacg tgtcccttta tctctctcag tctctctata   900
aacttagtga gaccctcctc tgttttactc acaaatatgc aaactagaaa acaatcatca   960
ggaataaagg gtttgattac ttctattgga aagaaaaaaa tctttggaaa aggcctgcag  1020
gg                                                                 1022

<210> SEQ ID NO 38
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0650

<400> SEQUENCE: 38
catacttaat tctaaaaaaa caacacttat agtttataag cagctcttat gataaaaatc    60
tttctgagtt atagctctgt taaacttgta ttcaccccaa aaacggatgt ttcatttctt   120
attttttact tggagtattt tattgtaatt tgtaaaaaaa aatgtaaagt gggggatatc   180
atgaaaaaca acgtcacttt gtttggtcac aatatacatt tgataaaata atggtcgtcg   240
cgtgatttag ttgattttt ttttatcaac cacgtgtttc acttgatgag tagtttatat   300
agttaacatg attcggccac ttcagatttg gtttgccca catatgacat accgacatag   360
aaggttaaat ccacgtggga aatgccaata ttcaatgttt ggttttcaaa agagaatcat   420
ttctttatat gatctcaaaa gtatggaatt gaaatgacta atgagcacat gcaattggtg   480

```
ctatcttaaa aaccgaacgt ctttgaattt aatttgtttt tcaccaaagg tacctaatga    540
aaccctttca ttaaaaaata aaggtaacaa acaaaatttt gtattggaaa aaacatttt    600 tggaatatat aatttggtaa tagaattatg agcaaaaaag aaaaagaaaa gaagaataa    660 tgagcataat aaagccttta cagtattact aattgggccg agcagttttg ggctcttgat    720
catgtctagt aatcttaaac agacgataaa gttaactgca atttagttgg ttcaggtgag    780
ctaccaaatc caaaaatacg cagattaggt tcaccgtacc ggaacaaacc ggatttatca    840
aaatccttaa gttatacgaa atcacgcttt tccttcgatt tctccgctct tctccactct    900
tcttctctgt tctatcgcag acatttttgt ttatatgcat acataataat aatacactct    960
tgtcaggatt tttgattctc tctttggttt tctcggaaaa                         1000
```

<210> SEQ ID NO 39
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter PT0660

<400> SEQUENCE: 39

```
caagtcaagt tccaatattc taaggagaaa taatagtata ctaaacatac attagagagg     60
ttaaacttct ttttggattt aagtgtgtat gcataggcta tttattctta agtataacta    120
ttaactgtag ctagatttat acaagaaata cataaaactt tatgcatgtg aggtagccat    180
gaatatacgt acatgttgca atcgattata catgttgtat ttggatttct ctatacatgt    240
tttaacttgt cattctctaa gtatatacat accattaata ctgtgggcat gagtttatga    300
taagactttt cttttggaga ccagttttgt tttcctttcc acctatattt gtctataggc    360
ttcacggtac actagtttac aagtgttttt atatgttcta aataaaattg agattttccg    420
gaacggtatg atctgtttgc aaataaggac gtatatataa cagtatcaaa tatatttgtt    480
gttataaggc aataatatat tttctgagat attgcgtgtt acaaaaaaga atatttgtt    540 aagaaaaaaa aagatggtcg aaaaagggga gtaggtgggg gcggtcggct tttgattagt    600
aataaaagaa accacacgag tgacctaccg attcgactca acgagtctac cgagctaaca    660
cagattcaac tcgctcgagc ttcgttttat gacaagttgg tttttttttt ttttttttaat    720 tttttcatct tcttgggttt ggttgggtca ctcttcaggt caggtgtgta aaaaagaaag    780
aaagaaaaga gagattgttg tgttgtaacc cctttgacta aaatctaatg aacttttta    840 acacaacaaa actccttcag atctgaaagg gttcttcttc tctcttagtc tcttcgtcct    900
tttattctcc gtcgtcgttt catgatctga ctctctggtc ttctcttctt cttcttcttc    960
ttctattttt tcttacttcg tcactgttgt gtctgaac                           998
```

<210> SEQ ID NO 40
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0665

<400> SEQUENCE: 40

```
aaaaaggatg ggtaatggga cctatttttcc ccaacatccc acatgcacac ttccctctcc     60
```

```
attctctcac atttatttct ttcattctaa tttatccatt ccgtgtgtaa catattcact      120
aataatctca tctcactaac tcattcattg attgtgatat gtttatctag aattagtgtt      180
ttaacactgt gtctacatat gatttccttt tcattgtatg tgaacatgtt aactcactaa      240
tcattttgta ttttcgagtt aacatgagtc tccacttcgg tagactaaag taaagatagg      300
tttgagtata ataaagttta aaatttgctt taaaatcaat atttataaat aagttttat       360 cataagtgat ttttgtatgt tatattggac cttgtataaa cagactacag aagaaaatta     420
tttatgagaa cttgtaatgt tagagtggac ctcgtataaa ctaattatgt gggcttttac      480
cataaactat ttatgaaaat tattatggcc cacaccacta taactaaagc ccacatattt      540
agcagcccag tttcattgta agagacatgt tcgctctgga actagaattt tctggttttt      600
gggtatttgt tttcttatgt gtagagaaat gatggtaacg attaaatgtt gtgtattaca      660
atttacaatg gtaagacgat taatatattt acacacaatt tgttgttgc tgtaacacgt       720 tagtgtgtgt gatgatagaa tttcataaag ctttaactac gaggggcaaa atgttaattc      780
taaatagttg acagcagaaa aagatatgta tacataatat aaggattaaa acgtaaataa      840
taataaataa ggcgagttaa attaaaaccc tgttaaaacc ctagcttgaa acacatgtat      900
aaaaacactt gcgagcgcag cttcatcgcc atcgccattc tctctctcat caaaagcttt      960
tctccttgat tttcgcattc tttagagtct taacgcaaag                           1000

<210> SEQ ID NO 41
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter PT0672

<400> SEQUENCE: 41
cagccgtaaa tcctccataa atttattttg caagttttgc tcattatata atgagcggaa       60
tttatgatat aatcgtttgt aataatgtta tgttttgatc aaaatttgaa attaaaagta      120
ggtgagaact tgttatacag tgtagataag gtggatcttg aatataaaaa taaaatttat     180
aagatgtatt taaagcagaa aagcataaaa ctttagataa aataatgtaa aaatgtgtta     240
gcatcaatgt tgggatattg gccgacccga acttaatcaa tgtcggaagc cattacttct      300
ctcccaaaag acctttttcc ttcggagaac taggaacttc ctcactacct ttcgcttaac      360
gtgaaagcca taaatttcat atattcataa aaatcagaaa atctaaaact gtttagtatc      420
acctgttttt ggtatagact attggttttg tgttacttcc taaactatat gatttcgtac      480
ttcattggat cttatagaga tgaatattcg taaaagata agttatctgg tgaaacgtta      540
cttcagtcat gttgggtcta gatttacata ctactatgaa acattttaag ataataatta     600
tcctagccaa ctatatgttc tatattatgg gccaagaaga tatagaacta aaagttcaga      660
atttaacgat ataaattact agtatattct aatacttgaa tgattactgt tttagttgtt      720
tagaataaat agtagcgtgt tggttaagat accatctatc cacatctata tttgtgtggg     780
ttacataaaa tgtacataat attatataca tatatatgta tattttttgat aaagccatat     840 attactcctt gacctctgcc cccatttcct tttactataa ataggaatac tcatgatcct     900
ctaattcagc aatcaacacc aacgaacaca acctttttcca aagccaataa taaaagaaca    960 aaagcttta gtttcatcaa agacgaagct gccttagaa                             999
```

<210> SEQ ID NO 42
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0676

<400> SEQUENCE: 42

```
aagatagtac agtttcagtg ttttgagaaa aaaagctgaa ctaaaactaa aatgtttaag      60
gacacaatat ttagtttcaa ttagataatt caacagtttg aacaattttt tttttttttt     120
tttgaagtca tttatttata caatgtttta aaacgcatta agcatttagg cagccgacaa     180
acgcctattg tctaactgta aataggcgct tccacttagg ttcatattgc atatttacta     240
tatgtgtata gtgacaaaaa ccaatatttc tcttattttg gatgaaggta tagtagttgt     300
taaatgttca atataattaa gcattaatga caaataaaat aaaattaatt tagttgataa     360
aaagataatc ttataaaaag atcgatgaat agatataatg gtttactgaa ttctatagct     420
cttaccttgc acgactatgt cccaaggaga ggaagtacct taactataat tctgaacata     480
attttgtcta tcttggtgag tattatatga cctaaaccct ttaataagaa aaagtataat     540
actggcgtaa cgtaataaat taacacaatc ataagttgtt gacaagcaaa aaaacataca     600
taatttgttt aatgagatat attagttata gttcttatgt caaagtacaa ttatgcctac     660
caaaattaat taatgattc aacaggaagt ctgagatgat gggccgacgt gtagttacgt      720
ttcttgaatt gtgagagatg gtatttatta tactgaagaa acattatttt actaaataaa     780
ttttcatttc acatcttctg taatcaatgc gggtagatga agaagttgtt aatacgatgg     840
ccaaccatat ggatctcttt tttggcgttt ctatatatag taacctcgac tccaaaggca     900
ttacgtgact caataaaatc aagtcttttg tttccttta tccaaaaaaa aaaaaagtc       960
ttgtgtttct cttaggttgg ttgagaatca tttcatttca                          1000
```

<210> SEQ ID NO 43
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter PT0678

<400> SEQUENCE: 43

```
aattaaatga aaccgcccct aaattaggag ggatttgggt aagtggtaac acattcactg      60
gaaacatgtg aagaaaggag gatgtcaagt agctgaaaac tcagtatagt aaccaacggc     120
ttctcaccaa cctttcatta ataatttggt catccctata tttttattca acattttgtt     180
tttcaatagc ttagagcacc ttaatacctt tcagtgtttt tttataaaaa aaacaaaaat     240
tgggattaat catcaatccc caaatgtaac gtttacttag attatgttca ttttttctata    300
cacacaaatc atattctttt gttttaatct tcgaaaaacg agaggacatt aaataccccct    360
aaaaaggag gggacattac taccaacgta cattaacatg tttgatagca aacgatttat      420
tttgttcgtt ttgaaaaggg gaaagtaatg tgtaaattat gtaaagatta ataaactttt     480
atggtatagt aacattttcg aataataaga gagggaaaac actcgccatt gtcggcaatt     540
tagaaccaat attagaaggg ttttttttaga gaaaaaggac ttaaaagttt agagacctta    600
acaacaactt atttagaaat agacatgctt aagttgacaa cagcgagttt attttctata    660
```

```
tcgaagaaaa atacgaactt tttcttaatt agatttcgaa tgcatgcact atcgagaatc    720
gaccgtcaca agaaaaaact aatatacata ctgtacatat ctatattcaa tattggtggg    780
gatgggttta atgtgtattt ataattcatg gataaattca cacaataagg tccatgaaac    840
tagaaggtac caaaaataag cattaatgac tctttgccac ttatatatat gattctctca    900
tagtaccatt ttattctccc aaacctatct tcttcttcct ctcttgtctc tctcgctctc    960
tctcttctac attgtttctt gaggtcaatc tattaaaa                            998
```

<210> SEQ ID NO 44
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0683

<400> SEQUENCE: 44

```
gattgaatga tgagtgtgca cccttgtatt actaataaaa aatttagcaa cagttataag     60
ctaacgtcat ccatgagtca ttcattagat tcactatttg cgttctcaaa aatcgaattg    120
ttaaaatttg agaagctcta atatacgagt caatgagatg tggcaaaagc atgtccttga    180
ccataaaatt tcgagggtc aactcattag ataaggacaa gaatcaacca attgaaggcg    240
tcttctataa caagtttctt tattactaat attaaagtcc aatggggtga ggggagaag    300 aacttaaata aaaggaaata attggtaagt gaataaaatc taaatacgat actagatgat    360
tgatttgtgc tagtgcatgg tattagatca gatatgtgtt actattcgaa ttcaaattgg    420
catattccat gttgttgata agaaaattgt agaagtgtaa aagctgagtt actatattca    480
aactagtggt ttacataaag tgagacaaca actgtttcac aaaaatgact ataaaatagt    540
aagtagtatt aggtcaattg attttaaaat tttaatcaaa ttcaaatttg tgatataatc    600
aaatttgttt atagaaaatg ttaagaaatc aattttggca gaactaattc agtgagaaac    660
aatcatttac aaaaacaatt ttaacattat ttaacagtaa gatttgacat ttaacccgtt    720
cgtgtgaacc catcatatct aacatggctc tacccatgac gcctccatgc catggacaat    780
tttgacagat cagaagttct gaacgtggac gaggtaagaa caccatgatg atacgattgg    840
agttagttat gtcgccaccg acatcactgc caatctcatt aataaaagtg gtactaaatc    900
tctaatctct attaactata aatataacaa agaaccaaaa gaaagtttct tatctctctt    960
atctttcata atttccaaga aacacaaacc ttttctacta                         1000
```

<210> SEQ ID NO 45
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0688

<400> SEQUENCE: 45

```
acgttcagag gcatcgcttt tgtacaaatt gaagcgggtt tgttcaatat ttaaaataac     60
acaggaaaca ttcaaatgta ttattgatgt tgcttaggtt tgtgaaatga tatgaaccat    120
atcgtatata ttactagatt tttcttatat gttttaaggg tagtggggct gacctatcat    180
tctgtttggc attaccaatc agactatcag agtattcacc attcaggatt ccataactag    240
aaaaagaagg ggtttacatt ttctcatact gtataatttt ctactatcag agattttatc    300
```

```
gattacatta atctcatagt gattattctg atttataaaa aagttgacaa ataattaaa      360 accagtattt tataacaaga ttgtctctct cccatggcca ttattttgac ctctgactta     420
tttaaatctt aattaacagc ataatactgt attaagcgta tttaaatgaa acaaaataaa     480
agaaaaaaag aacaaaacga aagagtggac cacatgcgtg tcaagaaagg ccggtcgtta     540
ccgttaaggt gtgtcgaact gtgattgggc cacgttaacg gcgtatccaa agaaagaaa      600 gggcacgtgt atagatctag gaaaaaagaa agaatggacg gtttagattg tatctaggta     660
ccaggaaatg gaacgtcaca ccaaacggta cgtgtcggat cctgcccgtt gatgctgacg     720
gtcagcaact tccccttatt catgcccccc tgcccgttaa ttacgtgtaa cccttccatg     780
cgaaaatcaa accctttttt tttttgcgt tcttcttcaa cttttctttt taaatcaaac      840
cttttctttt taaatcaca ttgcatttcc taacgctcaa caaaatctct ctctactaat      900
atctctctct ctctctctct attgttgaag aagactcata atcggagatt gtttgttttt     960
ggtttgctct gtaaattgga gaagttttgt tagagatcaa                          1000

<210> SEQ ID NO 46
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0695

<400> SEQUENCE: 46
aacattttct ttaacttact cttaaatttt aatagtaagt tgatgcatgt tatgttgatc      60
cgtcttgatc acaaatattg ttttatggac gaattctttg acagtaaatg gctatagtga     120
ctcagcttgg agcatcccga tatgaaaaca aagtgcagta ttgtgtcgtg gtcatcacta     180
acgcactttc ctagaactat cgcgcgtgtt tgacctatgc aacacaccag atgtcatgaa     240
cgtatactta aatagaaaca atgatataga caattggcta tattctgtca tggaacgcaa     300
accggataac atgtctatta gattcatcgg acttgatcat ggttatgtct taatagacga     360
attctttgtt aacgattggt taaaacggct cacgttagag catcctacta tgacttcaaa     420
attgataaat attacatgga aatcactta atttagtta gaaggtagtt aatttagata      480
ttcttattta ataattaaa aaatagaaga aaaaagatg agaagagttt tgtttataa      540 aataagaaat atcttttatt gtaattttaa aattaaacaa atttaattta tattaaaatt    600
atctttgttt tattgttaag gcaataatta ttttttggt gggaattgtt aaaacaataa    660
ttagtatact gttaagtggt cctttaataa taagataacg tgatttaaaa aagaacgaga    720
caggctaata tagtagagag gaaaaaatac aatttaggcc caataaagcc caatatagag    780
ttgtgctcaa acacaggtct tcgccagatt tcctatgacg ccgtgtgtca atcatgacgc    840
caagtgtcat tcaagaccgt cacgtggcgt tgtttctaca cataggcgat ccatacaaat    900
cagtaacaaa cacgaaaaga gcattcatat gtacgaaagt agaaagaag agactctttg    960 tgataaaact aagtaagaaa tagcataaaa gtaaaaggga                         1000

<210> SEQ ID NO 47
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
```

<223> OTHER INFORMATION: Ceres Promoter PT0708

<400> SEQUENCE: 47

```
gtttccaaaa ctagtattct ttatttgctc tattcattat attttatat ttgtaacgtc      60
ccgaccgtct ttattaggtt tcgacaatca cttctcggaa ggtcgtccat cctgaaatta     120
ctctatccta aacatgttta actataaaat tctctcgaaa cttttgtaac gtatataacc     180
acataaattc tcttaaactt atttgcatac accattatat ttctgaaatc gatatgttac     240
aatattattt aatatttaga ttacttttac tgaatcgaat taaatatcaa atcgaaacaa     300
atctaatcta ccaaaaataa ttttgttata aacatttctt gcctagttct acctcatata     360
cattttagtt aaagaaagaa atcacaacaa ttcccataat tcataatta aatccacaaa      420
atcttggagt aagtaagaga aataaaaaga tagtatctta acataaacaa ttcaaagatg     480
ctctctcaca caattcacac acacttacaa aacaaaagac agaaacaatg ttttcattca     540
aatcaaaaga agttataaca ctagtacaaa aaaagctcaa attctaatag taactctttt     600
tatttcccaa ttacccaaag attctctctc acttcacaaa actagctttg agagtcgtgt     660
tccacaaaat ccattaaagc tgaaacggtt ttgctcacca ttcaaacaaa tacaaaattg     720
caaaacccca aattataaca aaataatata aaaattaaac cgctaaaaag agtgaaccaa     780
caaaaatcgc cgaatgtgtg tgtaatgaga aaaccgaccc atcatcccaa tcatctcttc     840
ccgtgtcact ctcttcctct cccacgtttc ttctctcttc cctttatggg ttttaacttc     900
tccttcttct tcttcttcaa tcttcagttt tcaaattcaa caacaattca cattttgatt     960
tcttcatcat ctctctctct ctcgcttctc tctcaaatcg                          1000
```

<210> SEQ ID NO 48
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0710

<400> SEQUENCE: 48

```
tagtgcgcgt ggggagaggg aatggtgaaa ccttagtggt taagttatga ggaaaatgat      60
aaaaggataa aacaatcaaa tgcagcttga aacggccata acataaagta ccttatggtg     120
gtgcgaatat ttttgtgttt ctttcactct tttattgctg aaagctacga cacttgtctt     180
aatatattgt ttccgcaagt cacatgatct actttttatt taacgtctag aaacgccgag     240
atatatgatg attagtatat cacgtctatg caaattgtta gttcgtgttt ggccaaaaga     300
tatcgagaca tgtctgaaga accgagtctg gttttgagat atttcttcaa gcattactat     360
acaatagaaa aaggagacac gcgaatatga taatagcaaa aggcataaaa aggcgaaaat     420
taagaaaaaa cgtaaagtga tttggcctca atcaacggga acgtatctta attttagagg     480
ttcttctttt acttttgaga cgagagagtt tgcgtctttg cgagctgctt tggttgacta     540
aacattatca tattgaaaac caaaatacaa cggaggaata tttgtcacag tttcactttc     600
acattgtttc cttaacgttt aatcaacctt gttcaaaatt tctatagttg taatcatcat     660
tgtttacaaa attttcgttc aaagatgatt ttaaataaaa ttgtgaaaga aaacctttc     720
tgaaataagg attggatgat agtgttaaaa gaaaaatatg aactgaggca aaaagaggag     780
tggtccccgg aagattgtga aatgtgtcat ctaaaccagc cagacgtagt cacgtgttct     840
ctctagcttt atgaacttcc ttagccagca ccatcattgt gattgtagta tatatgtaac     900
```

```
cctaccttca tctctcccat tttccattct ccatatagac tccttttacaa tatacaaaac    960 ctatccaaaa gcgaagaagc caagcaaaca tattataaaa                          1000
```

<210> SEQ ID NO 49
<211> LENGTH: 1002
<212> TYPE: DNA
<213> ORGANISM: Arabidopsis thaliana
<220> FEATURE:
<221> NAME/KEY: misc_feature
<222> LOCATION: (1)..(1002)
<223> OTHER INFORMATION: Ceres Promoter PT0723

<400> SEQUENCE: 49

```
gtcatatctt atcaacacgt caacgatcaa aacctttagc ctattaaatt caacggctta     60
gatcaaaacg aaactaggtg ggtcccactt ttaatatcgt ggctgcataa catttcctcg    120
ataactgaag ccgttgtggt ctttctcaga atctggtgct taaacactct ggtgagttct    180
agtacttctg ctatgatcga tctcattacc atttcttaaa tttctctccc taaatattcc    240
gagttcttga ttttttgataa cttcaggttt tctcttttg ataaatctgg tctttccatt    300 ttttttttt tgtggttaat ttagtttcct atgttcttcg attgtattat gcatgatctg    360
tgtttggatt ctgttagatt atgttattgg tgaatatgta tgtgttttg catgtctggt     420 tttggtctta aaaatgttca aatctgatga tttgattgaa gctttttag tgttggtttg     480 attcttctca aaactactgt taatttacta tcatgttttc aactttgat tcatgatgac     540 acttttgttc tgctttgtta taaaattttg gttggtttga ttttgtaatt atagtgtaat    600
tttgttagga atgaacatgt tttaatactc tgttttrcga tttgtcacac attcgaatta    660
ttaatcgata atttaactga aaattcatgg ttctagatct tgttgtcatc agattatttg    720
tttcgataat tcatcaaata tgtagtcctt ttgctgattt gcgactgttt cattttttct    780
caaaattgtt ttttgttaag tttatctaac agttatcgtt gtcaaaagtc tctttcattt    840
tgcaaaatct tcttttttt ttgtttgta acttttgttt ttaagctaca catttagtct      900 gtaaatagc atcgaggaac agttgtctta gtagacttgc atgttcttgt aacttctatt    960
tgtttcagtt tgttgatgac tgctttgatt ttgtaggtca aa                      1002
```

<210> SEQ ID NO 50
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter PT0740

<400> SEQUENCE: 50

```
tgtggccact aaagatttac ccttaaccgg gcccatataa gcccacgtca agtggcgctt     60
atacgctctc cgtaagagag ccaacatttg gtatgtaatg ttgcaaatta ttcttcaaga    120
caataaattc aaatataatt caatattgtc caaatatagt gatgtacttc agttgtgcac    180
atagaaactc cactaaaacca actttttagat agatgcattc acaaattttc aacaatgtcg    240
cgaaagtcta atccatcacc agattctaac attttaatta ttatatttaa ctatacatac    300
tctaatcagc atgagtcaaa cgtgtacaat agcccaagca tataataaga ccaaagtcaa    360
actcaaataa atgtctccaa actcaaaact tgaaaaagac ctaattatta catggtagat    420
atgactttgt cgacaagtaa accaactaat cctcgaagct accttctctt cccagttatt    480
```

```
atgtgtgatc gatttataaa tctcttcttc taataacacc tatatttttc ttatgatgtg      540
aataaatata aaacttttaa ctttaaaaca tatttatccg aaatattgca cttagatttc      600
aaatagataa ataatagtac tatctaactg atattgaaaa gacctaacac ggaaaacagt      660
tttataaaaa atcccaaatg tgggtaatta tcttgatttc ttgggggaaa cagaaaatgg      720
attaagatta atcggagtcg tgtcaagcag ctcgttaata actgtagcaa gttgactgag      780
taagcatcaa cgtgtcatct ccgtaaagcc cattatttct agtctcgccg cgtcttctct      840
tccacgtagc acttcacttt ttctctcctt ttgtttcctt tggaacacaa acgtttctat      900
ttataggaat aattacgtcg tccgtatctg tgtcggaaca tagatccaaa ttaaaagcga      960
cttacttaat tacatatcgt tcgtgttttt ttcttcaaaa a                        1001
```

<210> SEQ ID NO 51
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter PT0743

<400> SEQUENCE: 51

```
tcgattggcc cgatcggccc caaaatcaag ctgagccgct tcaaacttca gcttttgaaa       60 tcaccccccaa actcatgtcc tcttatcatt ataactaaag gatctttcat tttatttaac     120
tcatcgtctt gcactaccca acccaaaggt tccaactata cccgaagctt tctaaaggtc     180
caaagacttt ttttttcgag ccagactatt caagccaaga aaagccaaac cccacaagcc     240 agtactttc aattccatat tataaactta tctgtcttgt tttagtccca ctaaaaacaa      300
cagaatttaa tttaggttga gctaaaaccc ttgacaaaag tgtatagtcg tcgattcagt     360
agcacactca tcactcatca gatttgatag ttgacctaaa gtatgactac tccatttcaa     420
ctaacaaatg aaaataaaag agacctaagg gttagaggat tgaaactata ctctcaagtc     480 tttatcact aggctactac cagctagtta acttgatgga tttaagcaag aaaacgtaga      540
atttatattc gagcagattg tttagctaaa aaagcttggg tttgaaattg ccttttctcc     600
catataagca cgtcggttcc taaataactc tttctagcgg agagtgtctt tccaataatt     660
taataaaaat ggtgtttgta tatcaaaaaa aaaagaaaaa agaaactgat cgagatagaa      720
cgtttgcagt tttataaaca atttaaaaaa caaaaaaaat taaactcaat gtatttttta    780
ttaattcaca aacaataata aatcatagga tcgaatattt acacggtatc aaaacctact    840
cgccgctact atataaaaat tgaagtcaaa tatcaaccgc aattattaaa ccagcaagac    900
aataattcat aaacttaata taaacataaa taaattaatg ttacacaacg atatatggtg    960
agggttatta ctatcttctt cctctcaaaa cacatctcct aaccttaagc tttagacggc   1020
ctgc                                                                1024
```

<210> SEQ ID NO 52
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0758

<400> SEQUENCE: 52

```
agctagccac atcagtgacc aaaaaagata attaacaaac caaataaaat aacaaatttt       60
```

```
gatcatttgg aataaaattt ataaaaggaa cgaaagcgcc ttctcacggg tcccatccat      120
tgaaatatat tctctctttt tgctctatat aataataacg cgtactaatt tgtagtatat      180
attattacaa agtcgatatt tgattgtttt gtgaacgttg atatattaat tttcttggat      240
gatgacaaaa aaagtcatag aaagtaacgt gtgaacatag cattaacaaa atacaaacat      300
aatatataac caaatatatg aaaataggat aaaatctcat tgaatagatc ttcttctatt      360
caaatatata aatatttgtt tgtctataaa attaacagag cattcacatt atctaaaata      420
atagtaaaat caaaataaaa ctaaataaaa ataactctgg ttttataacg attgatttta      480
aatattagtt tttgttgtaa agagatcatt atatatgtct gtaatatttt tatactgagt      540
tacatgatat ttagttatta tagcgtaatt aactaagata agaaattaac taaagtgata      600
ttctgattat tattattttt gttaggacac gtacgtggaa aaactaaaca ctataggtta      660
caaaacggta aataaactc accattactg gaaaatgttt gcatttgact caataagtaa      720
cttattataa gttactgata taatgcatag ttttgaaatt cttaaataaa ttattttggt      780
ttcgcatgaa aatatgaaag gagagaaatt tattattgtc acttatatat atatacatcg      840
taatcatttt ttcgtgaata attctctctc ccattccatt atttctcagt atctctcttt      900 cttccctta ctttattgtt gcttttaaac cttcaatttg ctcataaacc aaatatataa      960
tatcaaaaca aacaaacaaa aaatcagaat tcccctaata                          1000

<210> SEQ ID NO 53
<211> LENGTH: 921
<212> TYPE: DNA
<213> ORGANISM: Arabidopsis thaliana
<220> FEATURE:
<221> NAME/KEY: misc_feature
<222> LOCATION: (1)..(921)
<223> OTHER INFORMATION: Ceres Promoter PT0829

<400> SEQUENCE: 53
aaagttttga attattggga atcaatttcg aagttttgta attctttggg ggctaatagg       60
atattttatt ttcttggttt cgtctattgt tgttttttcta tttatggttg ggcttttaga      120
actctggaca ggcccatgtc atatgttttc ccttctcctt atattttttca ttttttcattt     180 tgttaaatta atgcataata tccaaaaaca atttaaattt ttgaaggaac cctttagtta      240
cggctccgaa gctttcacaa gtgagaatgt gagatcaaag aaggcaaatg gaggatttta      300
aaagttaaaa tcatctttta tctgcaaaag ttgacaattt ttttgtatca aatctaaatc      360
atcaaactct cttaaactac aagagcataa caacctctat gtaatccatg aaataatctg      420
cttgaaggac ataacataaa tcattatggc tagagtgact aacttcaatc aaatcctctt      480
aactctagct cccttacaat ggtatcgtaa acattatgc attagggatt gttgtcctag       540
gaaaataaaa taaaatccc cacagaccaa ctaccatttt aacttaaaaa taagcttcgt      600
ccgcgacgaa ttgttttcca tcctaaaaat agaatggtgt aatctgctaa tggtttagtt      660
ccattaactt gcaagttcta ttgaaagcct aaatgtcaat aaagatatta aaattcggag      720
tcaaaagaca aatgaatcaa aagcaacaag acaagtcagc tccattcttc actacccatc      780
ttttacaata aatcatctct cttttcacaa atttcaaact actctcattg ccctttagct      840
ttgttataga gccaacacta cagagagact cacacacttg tttcaataat taaatctgaa      900
tttggctctt cttataaact a                                               921

<210> SEQ ID NO 54
```

```
<211> LENGTH: 763
<212> TYPE: DNA
<213> ORGANISM: Arabidopsis thaliana
<220> FEATURE:
<221> NAME/KEY: misc_feature
<222> LOCATION: (1)..(763)
<223> OTHER INFORMATION: Ceres Promoter PT0837

<400> SEQUENCE: 54
aactacaagg gagacataat atcaccatct ggttcctgtt atcatctgaa gatttcttgt      60
tttaccttcc agtgataaaa tgatccttat aatacatata gatatattaa attgctgtat     120
tttaagatta tagatatata aggtacatga gagtgtttat ttaaaaaaat tcacttggaa     180
ttcatgtttt gtgatacgtt agattggaat ccatttggga aaagaagaat catctgttct     240
tatgtctcaa attttgactt cattcacttt tcttcttgtc ttttaagaaa gcttccacaa     300
tctaactgtt cgatgtgaaa actgagattc gagtaagaaa atgtgaactg tgttatactg     360
ttttttaatt agataattta gattgcactc agataaatta ataacattcc tcgaatactt     420
ttatgtgatt ggatatatta ggtatatctg ccaaccaacc aataaactgc tatgtttaaa     480
caaattaaat aaattagtat atgtttactc aagaataaag aagatagaaa agaaaattct     540
atatgagcta aatttgctgg aggaggcatc ggacgtgggt accagacctt ccaagcaca      600
cgagtagtgc ttagccatgt catgctaaca tacaccattt ggttcataca aaatccaaat     660
caaaatctat ttttaaaatc ttttgcacac gtctttgaaa aacacctctc atactatagc     720
tacggaagct tcaatttcaa ggtttgtcta aaagctaacg att                       763

<210> SEQ ID NO 55
<211> LENGTH: 751
<212> TYPE: DNA
<213> ORGANISM: Arabidopsis thaliana
<220> FEATURE:
<221> NAME/KEY: misc_feature
<222> LOCATION: (1)..(751)
<223> OTHER INFORMATION: Ceres Promoter PT0838

<400> SEQUENCE: 55
atactggtat gcttaaggtt gaagccaaga tctctgtctt acccaagtaa ccactttcta      60
ttagaaggga tcaacactaa gaatatggag atttaagcct aagggctaag gcggttctca     120
acaatacatg atgtgaatac aatcacagac gatttactga ggtttgttga taagatcttg     180
atcagtctct gcatcatctg ttcaacaatc tcaatctttg actgtttgct ttcggagcca     240
taaacagagg aatcccttat tccctgttat aggagcaata caccaagtat tatttccatg     300
gctgaaattc tcttatggaa acctaattgt tccattgaag ctgtaaaatc gaatctggtg     360
aatattctcg agcaaagccg catgctaatt atgtcaattc agaagagttt gattaggaga     420
ctcgaagcga gtttgatgat cttcttgat gttcaactcc gattgtaagg gtataattga      480
ctttcatgt attacggctc caccacctga cactaaggca ctcttgtcc atctcgttgg       540
tatcatcgga ttcggatggt aaaaataaaa agagcagagg aaacttgtta ctcatgcaag     600
cttctcaggt gccacgtcac tccattacgt gtcatcttca cacaccatct cgctcaaaac     660
cgatctcatt tttcaaacct taaggcaga agcaactgat taagttaaca ctcttgagaa      720
gctctcgatt aagcttgaac ttggaggatc a                                    751

<210> SEQ ID NO 56
<211> LENGTH: 669
<212> TYPE: DNA
<213> ORGANISM: Arabidopsis thaliana
```

<220> FEATURE:
<221> NAME/KEY: misc_feature
<222> LOCATION: (1)..(669)
<223> OTHER INFORMATION: Ceres Promoter PT0848

<400> SEQUENCE: 56

```
tctctttaaa tcagttaact aaccgtttat atatttacga taaggtttga agagattatt      60
gataaaataa tacatttcat aatcccgcgt tcaaccgttt aaagtaacat ttaagttgac     120
tatatctaat ttttttccca ttaaatatgg agctggtaaa ctttatcaac ttctaaaaag     180
tgtaacaaca aaaattaggt caatcacaat tctgttttt ttattattt ggattgactt      240
ccaattgcaa atagtcttag tgatcaccat tatcatacat atatacatca gtaggtttc     300
atcatgatat accacaaagt atttgacaag ccatatggtt ttggatcaaa aagtcggtcc     360
aaaattaatg ttttatgtgc aagaaccgac ccattgtaca cacgtgttaa catcttcaag     420
actttcatct ctattttct tttggtcatt aagatacca ttgatccgaa tctgttacat       480
tcccacctac ttttttaatt tttactatcc actccaaatt aaacacaacc gatgatttta    540
ataattggaa gcttttaaaa atatttcaaa acaagcctct ttgtgtttgt ctatatatat     600
acacgtaata agaaggtgaa tgaatctcac agcttacttg ttctaaggct tccaataacg     660
aaaacagta                                                             669
```

<210> SEQ ID NO 57
<211> LENGTH: 702
<212> TYPE: DNA
<213> ORGANISM: Arabidopsis thaliana
<220> FEATURE:
<221> NAME/KEY: misc_feature
<222> LOCATION: (1)..(702)
<223> OTHER INFORMATION: Ceres Promoter PT0863

<400> SEQUENCE: 57

```
cgggaaacga caatctgatc tctagtccag tcgattggcc cgatcggccg attataaact      60
tacatgagac aagtataaat aattattata aacttattaa gtttaagatc aaggcttttg    120
tgcaatgtat caatgaatgt tagatgtgat atgatgaaag caatgttta aacacataca     180
tagtcattga tcggaatgtg tgttattaga aatgcatgcc taagccgata gggttatcta    240
tgtttggtct tggacattat agccaaattt cgaatctaat tcttccaata tatatttttt   300
ttttttttgct tagggccact actagtattg cttatcaatt ttaagagctc atgaaaatgc   360
aacaatatag tagttgcaaa tccttgtttc aagagaaatc aaagggccac ttgtgaattg   420
aataataata atatttgcaa ataacctttc actaaaccat accaacaaaa ccacacagat   480
ttggcaaaga cataaccttt gggagacgtg aaaaggctca aaatttgaca attgtcctta   540
caaattcgct cattagtgca attgtgagat tgtttgcat ccaaatccaa ttcataactc    600
acactcgtct caaattcgaa aaggcctgca gggccagtgc actgggatcc aacaatgtcc   660
tccgactcgt ccaagatcaa gaggaagcgg aaccgcaccg cg                       702
```

<210> SEQ ID NO 58
<211> LENGTH: 435
<212> TYPE: DNA
<213> ORGANISM: Arabidopsis thaliana
<220> FEATURE:
<221> NAME/KEY: misc_feature
<222> LOCATION: (1)..(435)
<223> OTHER INFORMATION: Ceres Promoter PT0879

<400> SEQUENCE: 58

```
ttctaggaag actggtcaag ctaagctgtt tctgttttt gttttgtac tttacttttt    60 gtttgctagt gggaactggg tttattgggc cttgaagttg ataaagatg aataaaagac   120 atatcgccta aagcccatat gagaagcaga agacaaaaac ctccaacttt gggcataaat   180
tttgattata gttaaaagtc cagacccaat ttggcacctg gcttagttac gattctaagg   240
catgacacct gcctaatatg tttattacag aaaataaaga gaatcagcta ggtgtccctt   300
attgaacaca ttaacaaact ccaacgacac tacgtgtctt cgtgactctt actatatcca   360
aaaacctata gctaaagctg aattttccat gattagtata gtcccaacca aaaaatact   420 gaagaaggca taagc                                                   435

<210> SEQ ID NO 59
<211> LENGTH: 397
<212> TYPE: DNA
<213> ORGANISM: Arabidopsis thaliana
<220> FEATURE:
<221> NAME/KEY: misc_feature
<222> LOCATION: (1)..(397)
<223> OTHER INFORMATION: Ceres Promoter PT0886

<400> SEQUENCE: 59
agtgtatttg aaaacgacat tgaagaatta atatatttt ttttaatttt agtttttat    60 agtacaaata ttaaaacaaa caatcctacc atatcataac atttgtaaat aacattttaa   120
gttttgtttt gagttttaat taattttcta tgacaaaaaa atgaagtcaa tagactaagt   180
gaatcatata gtataaataa acacaattta aatagtttca aataaattta gaaagaataa   240
aacaaataga aatcagaagg tgtctgtttc ctcctcgcaa catacgatca aagagaaaca   300 acttgacccct ttacattgct caagagctca tctcttccct ctacaaaaat ggccgcacgt   360
ctccaacctt ctcccaactc cttcttccgc catcatc                           397

<210> SEQ ID NO 60
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0007

<400> SEQUENCE: 60
agcagaacaa ctatatttat tgtgtcacat aaatctgaga tcatttataa ccaccaaaga    60
acctatacac agtaaatgac aaatgtatct ccctctatct ctattgccca tatgtagatg   120
ctaaagtaag atttctcttt tttttaatgt acttttttt gtataaagta tattccataa   180
gaaaaaggaa aagcttgttt atggatcaat tgaccccaaa aaaagttttt agatcaaagc   240
ccaatataaa aaaaaaacac agtagtgaca caaggaact taaataaacc atgaattgat   300
ctataaacag tagagatcga taaggcgaac attttccatg tgaagtgtct tctttcatct   360
ataatatttt tgacatccaa taatttcctc tataatatca ttcacataat tgatagaaac   420
attatgttag aattgtccac atcatttgag ctgtaatata ttctgtttta acaaattata   480
tggtagttgc ttaatcttat gtccatcttc ttctatgcat cgttttcgcg cctagttgtc   540
cagtccattt caactaccta cctctaattc ttatcttaaa acaacatttt ttaatttaag   600
tattatgctc aaagactaac tagatagaaa accgttatta acattaaac gaattaaaag   660 tcttacatgg aaaatgtagg tttataaacc acgagttatg attgacaata aaaaaaatgc   720
aaatcatcaa tcaaaagaga cttgagtgcg actctatatc aaccattgca attaaaatta   780
```

| | |
|---|---|
| tctatcacaa aaattttaga cagattaagt taatttagtc taaattcact aatttatttt | 840 |
| ctataattag taattaacta tatttattta tttacacatt ttctgataat ttagaaattt | 900 |
| gcatgaataa caaatataag attttggaaa ttagtagcaa atttaattaa taattatttt | 960 |
| tgcctaaatg aaccaaacta taaaacctcc acatacacca gtcatcaaat ttacagagac | 1020 |
| aaca | 1024 |

<210> SEQ ID NO 61
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0008

<400> SEQUENCE: 61

| | |
|---|---|
| ctcgagagat gaagtcttag taatgtttga acaaacaata atcacgtttt ccatcaaatt | 60 |
| cgagcattta agtttatat tactacatgc cccaagatga taccgtccat ctcatccgaa | 120 |
| aatatttctg aaattgcgct aagacaacaa tgtttgctca aattcgatca tttaaagttt | 180 |
| acaaatctct catcaatctt acaaacttct cacactaaac agaggtacat attttcttat | 240 |
| aaagacaaaa ggttcgaaca gctggcttct caactcgagt tgtttgtcag ggcctctctt | 300 |
| cactaactac aagttggtac ttcaaatatt ggtggctagc ttcacgtgat attgtctaca | 360 |
| aattaaaccc atgaaaaagc tgcattaatt gttccaagtg aaccctgagg agtgtcaata | 420 |
| gtctttgctt tagtgtgatc attaaaccaa atctctaaat tcctaatttg tactaacatt | 480 |
| tggaacgtat ttcctactct tctccctgct ccaactccca aaaataagat tagttagatt | 540 |
| tctataacta atatacatgt atactcccaa aaacagtaaa accatattaa taaagctaat | 600 |
| tttgcataga tttatttcgg taaaccggcg gttcaagttg gggaaaaaaa agacaaacgg | 660 |
| tctaaagtca tccaaagaca aaaaaccaaa gacaagttga gagagacgag accaatcaca | 720 |
| acattgcttc gtagattgcg tgacatcatc cttgacggct actttcattt gtgtcttatt | 780 |
| tggataaaac gcacgtgttt aattcacgaa ccttcatagc aataagaaat ttccattact | 840 |
| ttcatatttt caacttttt tattacccat tacatgctta aaatattaat tcacaagtct | 900 |
| ttgtcaaaat tcaatatttt ccaggttcat gaacccttt tatctcaatc tactctataa | 960 |
| tatctcccta taaattacaa caaaacctct ttattttttca | 1000 |

<210> SEQ ID NO 62
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0019

<400> SEQUENCE: 62

| | |
|---|---|
| gatataagta gaatcatttt ttgccgccgt ttctcgctaa cacaccgaaa actgaatcaa | 60 |
| atctcctagc tcttctacgc aaaatcgagt gcatcgacaa tggcggaacg tggtgtcgaa | 120 |
| cgtggtggag atcgcggcga tttcggacgt ggattcggtg gtcgcggcgg tggaagaggt | 180 |
| ggtccgagag gtcgtggtcg ccgtgcaggt cgtgctccag aggaggagaa atgggtgcca | 240 |
| gtgactaagc ttggtcgtct cgtaaaggaa ggtaagatca caaagattga gcagatctac | 300 |

```
ctccattctc tcccagtcaa ggagtaccag atcatagatt tactcgtcgg tccttcattg    360
aaagacgaag tgatgaaaat catgccggtt caaaaacaaa ccagagccgg tcagagaacg    420
agattcaagg ccttcatcgt cgtcggagat agtaacggtc acgtcggatt aggagtcaaa    480
tgctccaagg aagttgcgac ggcgatcaga ggcgcgatca ttctcgcgaa attgtctgtg    540
gttccgatac gaagaggtta ttggggtaac aagattggaa aaccacatac ggttccgtgt    600
aaggtaaccg ggaaatgtgg atctgttact gtacgtatgg ttccagctcc gagaggttct    660
ggtattgtgg cggctagagt tcctaagaag gttcttcaat tcgctggaat tgatgatgtc    720
tttacttctt ctagaggatc caccaaaact cttggaaact tcgtcaaggt atgtactttc    780
acaatggctg ttttggtttg atgaactctg aattaggcag tgaaaaagta atcattacca    840
gttaagtgaa tttatattga agattaggat ttagctgatt gtattggttt gagcatgtga    900
gtttgtgttt aagattgctt gaattgaaat gctttaggtt gtttgattac gctaaattct    960
gactaatgta attcaaattg ttgttgtttt tttttggtc                           999

<210> SEQ ID NO 63
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0028

<400> SEQUENCE: 63
gtcagtgaag tcgattggta gtacttgaaa cacttggttg gtttcatgta tttggcctat     60
atataaacaa acatcgtaat tatatacgga ttttttttcgg aattttacgc catatctgta   120
agtatatata acatgcatgt cgttttcaaa ttcatatgat gaacgatcca cgtaagtgct   180
actactccta caatattgca tgagagagat atgtatttat aaattttatt ttgaagaaga   240
aataagaggg aaggttactt gggtggatcg atgtgaaaac aaaagaagaa aaagcgaaac   300
ccactaagcc attacatgat atcgaccttc ttatcttttt cctctttatt ttatttttct   360
catcttcttt ttgtcaggac ttttttctac ttaatgaaac ctccaaacta tctaactaat   420
acactcccat gtagaataaa gaaaattata taagatattg ttgatatttt gtaactagaa   480
aatatatttg ctctgtaatt tttcgtaagt taaatcaaca ttttaaagta gaaacaaata   540
ttactgcaaa aagtaggatc attattttg tccaaaatct cagttagcta tagggttgta   600
gtaaaaacaa aacacattct tgatttgccc caaaaaataa agagagagaa gaatattgtt   660
caaaagtggt ctcttctctc tctaattatg ttttcactaa acccaattag attcaaacag   720
tctacaaagt ccaaaagata aacatgggac aacaattcga tgcaaaaaat cctctttca   780 tgctcttttt ttattctcta gtcttttaaa ttactaataa aaactcacaa atccaccaaa   840
cccattctct acaactcacc ttcatctaga tttacccact cccaccgaga aacacaagaa   900
aaaaaatata catatataaa tatacaagac aacacatgat gctgatgcaa tatacacaac   960
aaagtattaa atcttagata ttgtgggtct cccttcttc tattcatttt cttattcatt   1020
aaaa                                                                1024

<210> SEQ ID NO 64
<211> LENGTH: 1024
<212> TYPE: DNA
<213> ORGANISM: Arabidopsis thaliana
<220> FEATURE:
<221> NAME/KEY: misc_feature
```

<222> LOCATION: (1)..(1024)
<223> OTHER INFORMATION: Ceres Promoter YP0039

<400> SEQUENCE: 64

```
ccgttcgagt atttgaaaat ttcgggtaca cccgcctaaa taggcggacc ttatctagta    60
tatatataca tttgaactat attgtttact ttttagttga tttaggctat gtcatgacat   120
tgacataaat ctacctgtta tttatcacgt gtaattcgtg taaagtgtaa actagaaagt   180
tcaaatacgt atttgttttt gttctgttat ataggattgt catagttgta aatctacaat   240
ttattacaac atgaataagt acacaagcaa tgtaattgga tttaattgct aaactcttta   300
catggtcaat ctaaatttga taagaaatac gtcacatatt actaagactg atagtttttt   360
tgttgtcacc aattatttt gttaaattga cgaaaacaat tccaaaaact caaatgtaca    420
aaatcataca gtctcacaaa catctcatag agaaagatat aaatctccca tatgggaacg   480
ataacacgag gtcgaaatac tattcgtaaa actaaaacgc cttagttata aatcgttagt   540
tgtaaccgcg gtcgagaata catacagatc cacgaaacta ctactacaca tgctgctgaa   600
ttggaatttg gaaaagacca tcttctttag gaagagctca cccaatgagt gacaaaggtg   660
tcggtggctt gttttctacc catatgtata catcaaatgg tagtttcatt aacgtttggt   720
tttgagaaaa gtaagacttt ggctagtagc taggttcgta taataaaac tcttttgaga    780
aagttcatca ctggtggaaa atgttaaacc ggttttttct catttttcc gccatgttaa    840
ccaccggttt aaaaagaccg taacacattg aaagattaat aagggtatat ttgtaattac   900
ggtttgctgg cattttttaa ttattatttt aattagagaa aatagagaag ccctatcaat   960
gtacatggta tatatataaa aggcaaaacc ctagaaaacg atactattcg actcagccgt  1020
cctt                                                               1024
```

<210> SEQ ID NO 65
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0050

<400> SEQUENCE: 65

```
aatctgatct ctagtccagt cgattggtac ttgagggaaa catcatattt ttaaaccttg    60
tctcagtaag ctaacacaca ccccttgtga ttacttatcc atgtttatcc acaagaatgc   120
agttggattg agatattttc ttctttgttg aaatcaggcc tcaaggtgtt catgtggtct   180
gcaaaaaaat tcccaaaaat aaagatagtg acatctgaaa tcgataatgg attagacgaa   240
gagtttcgtg ttattccttg gtatgggcgg gtttggggac agatattttg gcacagacga   300
ggactaggcc actgtggtcc tgcagcatta ggtgtcccctt ccatgtcctg cattacattt   360
tattgatgga ttcatcaccc tatctactac aacggctaca caaactatga gagtttttgt   420
ttactaataa atgcccaagt gaggggtcga tcgaacccgg gacacgtttt tcagtttacc   480
atatagaatt atccttggaa cccttgatac tccatagaac atcaccacct ctgttgtcat   540
ctcaggaatc caggttcaaa cctagtctct ctctccctag tgggaggtat atggccactg   600
ggccaatgat gacaaaatgc aaaaaaaata aaatacattt gggttcatta tctaaaatat   660
ctcttgtgtt tgtaagtttt ggttgcacac tcgtgtggtt gaagtgtgtg tgagaggtac   720
tatacaatac actctgcttt tgttttgtac ctatctcttt ctcttctcca catatccaag   780
```

-continued

| | |
|---|---|
| actttgggga taaagctgag atcattggtt gccatttggt tgtgtagaag caatcaccca | 840 |
| tttgctttat ccgaggttga taaatttcct cgggttctcc ttctgacacg tatgacaaat | 900 |
| tctaatagta tattcctcgt agatattacc tatatattct caatagttgc aggtacttaa | 960 |
| ggctttgtct tggcatcctc gtcctcttca gcaaaactcg tctctcttgc actccaaaaa | 1020 |
| gcaa | 1024 |

<210> SEQ ID NO 66
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0086

<400> SEQUENCE: 66

| | |
|---|---|
| cttatccttt aacaatgaac aggtttttag aggtagcttg atgattcctg cacatgtgat | 60 |
| cttggcttca ggcttaattt tccaggtaaa gcattatgag atactcttat atctcttaca | 120 |
| tacttttgag ataatgcaca agaacttcat aactatatgc tttagtttct gcatttgaca | 180 |
| ctgccaaatt cattaatctc taatatcttt gttgttgatc tttggtagac atgggtacta | 240 |
| gaaaaagcaa actacaccaa ggtaaaatac ttttgtacaa acataaactc gttatcacgg | 300 |
| aacatcaatg gagtgtatat ctaacggagt gtagaaacat ttgattattg caggaagcta | 360 |
| tctcaggata ttatcggttt atatggaatc tcttctacgc agagtatctg ttattccect | 420 |
| tcctctagct ttcaatttca tggtgaggat atgcagtttt ctttgtatat cattcttctt | 480 |
| cttctttgta gctggagtc aaaatcggtt ccttcatgta catacatcaa ggatatgtcc | 540 |
| ttctgaattt ttatatcttg caataaaaat gcttgtacca attgaaacac cagcttttg | 600 |
| agttctatga tcactgactt ggttctaacc aaaaaaaaaa aaatgtttaa tttacatatc | 660 |
| taaaagtagg tttagggaaa cctaaacagt aaaatatttg tatattattc gaatttcact | 720 |
| catcataaaa acttaaattg caccataaaa ttttgtttta ctattaatga tgtaatttgt | 780 |
| gtaacttaag ataaaaataa tattccgtaa gttaaccggc taaaaccacg tataaaccag | 840 |
| ggaacctgtt aaaccggttc tttactggat aaagaaatga aagcccatgt agacagctcc | 900 |
| attagagccc aaaccctaaa tttctcatct atataaaagg agtgacatta gggttttgt | 960 |
| tcgtcctctt aaagcttctc gttttctctg ccgtctctc | 999 |

<210> SEQ ID NO 67
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0088

<400> SEQUENCE: 67

| | |
|---|---|
| tcgattggga ttactacttc atctagtaag gttctgaaaa cgtttgttgt tgataaggaa | 60 |
| gattcgtctc aggttattac tgttgatctt caaggtttgt gattgtgacg cttatacatg | 120 |
| tgctgaaact gtggtgttta tttattgaaa acaaaaaaaa agtctctctt gtagtttcat | 180 |
| tgtactaaat agaaaacaag aaacgttttt tctttaatc ttctacattg ataatattgg | 240 |
| atcaaaggat tgtttctgca agacacaaca caaacatact tatactagtt tacttctact | 300 |
| aagtactaac tacatacccca tacacacact tgcacctaga ctttacttct agacatcatt | 360 |

```
accctaaggt agaaccaagc ttacaagcaa gttttaccga caactcttac attacaactc    420
tagtctgtag tctttaacgt agacttacta actagtcatt agtggtttaa ttttttaaat    480
tttcatccat atgttttgt tgtagatata aactaaagtc ggtcacattt aataattgtc     540
attatgtccg cgtaaaagtc aattcagcta ttggacattt atgaaatgta agattttctc    600
tctcatttcc ccgtgcgtga agacatgcat tggtttttct gtaataatca acaaatccaa    660
accccttttc gatctttatt tggacattgt tagagacaaa atttctctat agtcttttc     720 ctaatttgat accatgtttt tgtttctgca caaatttact cactggttta actaactatc    780
cacttattta tgattttacc attaggcgtc agctagccct agtcaaattt gtaaacaagc    840
caagctatct acataaatcg agatgtcatt aacgttaatc gtcgttaatt cgaatttgaa    900
aacatagata gctttagcag tacaatgggc aatggtaaga agaatagcaa aaggcccaat    960
atttggtttg cagaaattaa agccttaaaa aaaagcccac agatatttgt caaagaaccc   1020
taat                                                                1024

<210> SEQ ID NO 68
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0092

<400> SEQUENCE: 68
aaagattgag ttgagagaga tggtggagac gcagaacaga caaagggagt ttaccatata     60
gtgctctaaa gggcaatgag attgcagtga tgtggctatc cggggaatca tcgcaggtta    120
ttccttccca tgagcaacaa tcaatggatg ggttccaatt cagaggagaa acagaagaag    180 aaacgttttcc agagaaccac agtagggatt ctcgatcttg cgagttgcag agagcctctg   240
aaactgcaat agaaaggaca ctgatgaaaa gaacacactg aaggagtatg ccaatcatgt    300
gaaaactcag agcttgtatt ggtcttgtgg ttgatgaagt tctcacaaaa cctttggctt    360
tgaatctccc ctcattagtc atggtgagaa caagaacaag acgagaaaca gacaaagaag    420
atgaaaaaac ttgttggcca gtgttgacta aggggaata gccccagaca taacaaaatt     480
agacttgtcg tacatcttta atattttttt atctgtttct ttgtcctgac gctttcatta    540
ttcctgtgat caattttctc ataccattgg tccatcgtta atcctttctt aatttcattt    600
tctacgtaac atgagaggag accaagtcct atgagaacag ttgacgtaac agtggttgtt    660
aagttaagtt aaaagagga agctagtgag agtgaccgtt aggtagagaa gtgagatctt     720
taaccactct tctttctctc tctctctgct tttttcgtcg tctttcacat ctactgttcg    780
caaactctct tatgcttcca ataatggtga taccaattga gacttgcagg agaatctcct    840
cttctccaca ctctatcaac tggtcagcca tggaatggtc gtttcagttt caatattcct    900
ggattctttt taaggattcc tgtttctctt ctgttcctgg tatattctta acgacgaaat    960
tagtatcgga tcctggtaat acattttgaa gcttttaagt accattgcac tgggatccaa   1020
caat                                                                1024

<210> SEQ ID NO 69
<211> LENGTH: 1020
<212> TYPE: DNA
<213> ORGANISM: Arabidopsis thaliana
<220> FEATURE:
```

<221> NAME/KEY: misc_feature
<222> LOCATION: (1)..(1020)
<223> OTHER INFORMATION: Ceres Promoter YP0096

<400> SEQUENCE: 69

```
gaggtcagtg agtcgattgg tgcaaaattg aaaaattgaa gggtgaaaca aatttaaaga     60
taatatctat taaatcctct aattttaaaa atttagcaaa aattgtattt tcttatggat    120
ctgttagttc acacgtatct taattagtac caaatcatat ctaatgatta gtgataaaac    180
tagttagata tctatatgtg tctttaccat ttaacttgaa tccttcttct tttttttacg    240
taaacaactt gaatccttcg ttaatacata aatttaaagc attttttctt taattctatt    300
gatcggtata tatttactat aagttttagc tcatatgcaa tttcaaatga tatgctttta    360
aattttgtct aggtgtgata gttgtatctt taacataaat cttatagcaa aattatactt    420
gatattctaa atttatctat ttgctcttgt gaacctcata ttagtctaga gaaactttga    480
aatcctttca attagttgta tgtccaatac atttttacta acattattta gtcttttttaa   540
ttaagattat tgttagaaaa aaaaagattt tttaaaaata aataatatgt tttagataca    600
atgtgagtta ggcttcttat attttaaaaa ataaatttat ttcatactta aaaatagttt    660
ggaatttcaa tttatttggc tgaataccat aaaatatgtc aatttgaacc ttatacccat    720
tgactatttg gtgttagaaa ccctttaaca aaaaaaaact atttggtgtt agatatcaaa    780
ataaaaaaag tttaaccatt ggtttcttat attgaattgg atattgttac atgtattaaa    840
gtttttttgg tttaattttg aaacgttgat agaaactatt aagtttaagt ttggtagtat    900
atttatttgt ggaaaattta attgccatta aatataacgt caactttttt tggttttttt    960
tgagaagtta cgttgtgatt ttgatttcct atataaagt tagattacgt catttttaa    1020
```

<210> SEQ ID NO 70
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0097

<400> SEQUENCE: 70

```
ttcatcttta tatttaagag tttaaaaact gcaacttttg ttttttcttc actaagtctt     60
atggccacag ttaattaaaa gcagatgaaa ggtggtccaa tggaaaagga gaatgtgatt    120
gggctagttg ggagagttct gatgtctagt gttgggtaca cgtgtccgtc agttacacat    180
agcattaaat cagacggcat gtcattattc aaatctagtt cacatagtac gactaatagc    240
tgataaatta atgattatac agcatatgaa ttatgaattc aaaaaaaaaa aaaaattgaa    300
aatgttaagg agatgctata ttttacaaaa ttcatcgcaa tgcttctac taatttgcta    360
agtggtcttc tccagttagt cttgtcgatt ccaagcgata ttattaaatc ttgaagcatc    420
gctcaaagca ttatagctta agataaccaa attgttatta aaaacaccta gtgaaatttt    480
taaattaaaa caattttgat atctttgtaa tatctaatac tactctttct gtgtctaaaa    540
ggattaattt tcaaaaattt cacacatatt aaaaaaaaaa aaaattact agctaaacaa    600
ttttcaataa tcataaaaca atagtaactt aataatttt ttttattttc aaaatagtcc    660
ttcaagttta caattcattt tagtattata atcaacaaaa tttgtattaa aaagttggaa    720
aattaatctt tgtggaacaa aaaaatctag aaatcatttt ttagaattag agagaggttt    780
```

```
gataaaaaaa aataaaaaaa aatagagaga ggtagtacat actaaacgat gtgatactac    840
tattgacaaa atcttaattc tcagtttagt agaataaact agaaggaatg aatgaagtaa    900
atgcgaatcc aactactaac aaaccctact tagtcatcat attttcccat atgaaatccc    960
tatataaacc catcatcatc tcccactttt ttcatatcca                         1000
```

<210> SEQ ID NO 71
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter YP0101

<400> SEQUENCE: 71

```
ttctcgttct ctagaatatt gctggaccgg attaggtcaa tattattggg ccagattaga     60
tattgaattg tcgacgttgc ttacgttacg ttatatcttg tttaagaatt aaacctatcg    120
acttagtctt aattaagaaa acattgcctt aaattctctg gtctgcgacc gttttttga    180 ccgttaaccc ctaattaaag aaacaaaata attatagaaa gagcactgaa atgtgattat    240
tttaacagta ctcttatgag aaaattcgta cttttttagtt ttttttttgt acaaatctct    300
aagaaaaaca ctactactaa ttaagaaacg tttcaaacaa tttttatttttc gttggctcat    360 aatctttctt tctcggtccg ggactaaccg ttggcaaaaa aaaaaaaaaa gttgacaata    420
attattaaag cgtaaatcat acctctcaaa taaaaacttg aatttggaaa caagacaac     480 taaaaaactc gaatttaaga gaattcctaa atcaagtga agtatcatca cttggtaaaa    540
tttcataacc gttggcttct atttctatgt gtgccttggt ttgcaggaga taatatttca    600
tttccaacca atgatattcg tacacatagt caaacaaatg tttgtctttg ttattatatt    660
gagaaagaaa caagaaagag agagagagat agataagacg aaggaagtga agcttccaag    720
cgcccaccgt taaaaatctc gtgtgcaagt ttcaaataca agtggccggt ggtctccata    780
atttgatcgt catccaatta aaaggaaga aaaagcgtgt tttatacaag aaaactcatt    840
aaaatagcaa gtctagaaat atctcaacac taatctacca cgtctattac acacacacac    900
acacacactt gatcttaatt tattttcaag attcaagaaa atacccattc cattaccaca    960
acttgaccac acgcctatat ataaaacata aaagcccttt cccc                   1004
```

<210> SEQ ID NO 72
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0102

<400> SEQUENCE: 72

```
atttggttga taacgttttc actcgactaa ttatatactt cagaaggata gtaatagaat     60
accaaaataa ttaaatgatt ggttagtgcc ttagtggaga ctttttaacc gattctaata    120
gactaatgat gtagctaagc atttatttgg gatcatcact gtttgaaaac gtgaaatgtg    180
ataaaagtta tgaaacgatt aaaatataaa ataaccgtac aaaacattat gtaccgtttt    240
tttctctgtt cttttggcga tttggtttag ttcgttacac tctaaatgtt attgcagata    300
tatatataat gatgcatttg catctgagga acatataatt ccggttaaca cttccaaatc    360
```

```
ttatatccgt ctaggtaggg attttataaa tcatttgtgt catcatgcgt tatgcttgtc    420
ggctttgacc ataacgcaga gatatagaac tagcttttac ttaactttta gatttattat    480
ttgatctaga gttaagtgga gatatatagt gttttgtta gattattggt ggatgtgaga    540
gtttgtcttt agtttcaagt tgagaatata aggcaagagg agactctgag gcaatcagag    600
gttttgattg gcaaaatatc caaaaggccc aaaccaagtc gaagcccatc tcgtacaaaa    660
aaagaaagag atctgtaaga aaaatattc tttgatattc ttacaaaaat aagtgtaaaa    720 ctttattag tcaaaatctt caatctttaa aaactctcat cactcctacg aaagcgcgtg    780
agagttatga gacattcctt aatagcatta ctcacaagtc acaagttcaa aacgtctgac    840
tgaaacagaa acaagccttt gttgaagtct tgaagaagag acattagtac tcgtcgtata    900
gccataaaag gtaatatacg aaatttcttc gctaatctct tcaccttcct ctacgcgttt    960
cactttcact ttataaatcc aaatctccct tcgaaaacat                         1000
```

<210> SEQ ID NO 73
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter YP0103

<400> SEQUENCE: 73

```
gttttgaaga acaatctgga tcgaaatcta acataaggtc atcgtattca agttacgcag     60
tcaaggactt gacatcatcc tactctggtc tgaggttacc acttccaaag atgggatttt    120
tcgactcggt atgcttccta agaaattcgt tttattgaac ctagcaaata tcttgtaatg    180
taagattcct gagatgatga agaaaaaaca aacttttgtt acagcaggag aacggagaga    240
aagaaaacag agaaccaaat gctcttgaag caaacagaag aagaagacac aaatccaaac    300
ttgagacttc ttctacacca gaaaaccgca gcattctggg acaacgcaaa acacgaaagt    360
gaaacgggca atgatatata tgtcttgggt gcgttacaag gcatcgtttg caactgttga    420
gttggataag tcaactgtct tcttttcctt tggttgtagt agctgccttt ttttttcctt    480
gttgctttaa gaaatagccc gaaaaaaaga atgttctaca tttcggagca gaaaactaac    540
cgaatgagtt tttggtcgga tcatcggatc gatcagatat attttgagtt acgaactgtt    600
ataaaaaaag ccataatttt gtgttgagtt tgcaaaatac cttataactt gttatttgag    660
attgcacctc catatatatt aattcgtaag agtatttatt aagtaagctt tagtataaat    720
ccttttttcc tttaaagtaa gttaatgttc tactaaataa tagtaaagtt gaagaaccgc    780
tccgttttta caccatgcac gtgttatcta acaaagaaaa tatggtacac ctaatggcta    840
atgcaaagga caacacaatg aaactaactt gactctgtgt tatagaaacc catagacatc    900
tgcatacatc ctagtatttg tataaattgg actcaaattc ctgaggacaa tcatagcaaa    960
caatcacatc atcgcaatat acataaacaa agaggaaga aaaa                    1004
```

<210> SEQ ID NO 74
<211> LENGTH: 1003
<212> TYPE: DNA
<213> ORGANISM: Arabidopsis thaliana
<220> FEATURE:
<221> NAME/KEY: misc_feature
<222> LOCATION: (1)..(1003)
<223> OTHER INFORMATION: Ceres Promoter YP0107

<400> SEQUENCE: 74

-continued

```
taacaatcct tgggaacatt gcatccatag atatccggtt aagatcgatc tttgaactca    60
taaaaactag tagattggtt ggttggtttc catgtaccag aaggcttacc ctattagttg   120
aaagttgaaa ctttgttccc tactcaattc ctagttgtgt aaatgtatgt atatgtaatg   180
tgtataaaac gtagtactta aatgactagg agtggttctt gagaccgatg agagatggga   240
gcagaactaa agatgatgac ataattaaga acgaatttga aaggctctta ggtttgaatc   300
ctattcgaga atgttttttgt caaagatagt ggcgattttg aaccaaagaa aacatttaaa   360
aaatcagtat ccggttacgt tcatgcaaat agaaagtggt ctaggatctg attgtaattt   420
tagacttaaa gagtctctta agattcaatc ctggctgtgt acaaaactac aaataatcta   480
ttttagacta tttgggcctt aactaaactt ccactccatt atttactgag ttagagaat    540
agacttgcga ataaacacat tccccgagaa atactcatga tcccataatt agtcggaggg   600
tatgccaatc agatctaaga acacacattc cctcaaattt taatgcacat gtaatcatag   660
tttagcacaa ttcaaaaata atgtagtatt aaagacagaa atttgtagac tttttttttgg   720
cgttaaaaga agactaagtt tatacgtaca ttttatttta agtggaaaac cgaaattttc   780
catcgaaata tatgaattta gtatatatat ttctgcaatg tactattttg ctattttggc   840
aactttcagt ggactactac tttattacaa tgtgtatgga tgcatgagtt tgagtataca   900
catgtctaaa tgcatgcttt gtaaaacgta acggaccaca aaagaggatc catacaaata   960
catctcatag cttcctccat tattttccga cacaaacaga gca                    1003
```

<210> SEQ ID NO 75
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0110

<400> SEQUENCE: 75

```
gggatgcggt tccgcttcct cttgatcttg gacgagtcgg aggacattgt tggatcccag    60
tgcaatggta atataaaaca agaaaacaag agattttata ggacaatcac taaatgacat   120
ttaattgatt aaacatttat tcattaataa ttgtatgtta ctaacttcaa catttaataa   180
ttttgtttaa gatacgtttta catcagagac tattaatatt tttacaggtt gtaactttaa   240
actttgtctt gaatcgaaca tgactataga ttttgggcaa acttaaagat aacaacattt   300
ccgttttttt tcaaattatt acaaatcaaa ctgatatatt agacacaaca cgattacacg   360
taatgaaaaa agaaaaagat aaaaagataa agaagggat cgattctgtt tggtctggtt    420
tagtgagatt caaagttaag ctcttccttt caagacatgc cttcttaaac cgggaatgtg   480
aacgtttgta atgtagtccg tccagttaat gcttccaaca tcaaatccaa attctctctt   540
ctcgtcctct gacatattct ccattaatct ctggggtatt gctgttatca aatctgtaaa   600
agaaaccaaa aaaaaagat gaaactttg cgggtaccgg ttttgtctgc tctaagaatt    660
agaatgttaa tgagttctgt cttaccttcc accatagaaa gtgtatggct cataaatagt   720
agcaaggtgt ttggcttgtt caacagattt cttgcatata aactttagct tctgcatcat   780
cttactatcc actgaactca taccactcat caacccactc cgttcttgag catctctcca   840
caaatgatcc gagaaatcat caacggaatt gaaaagtttc atcaaacgca ccataatagg   900
atcacccttta gagtccatgc atggagatgt tttgtagtgg ttataaagaa gctccgctaa   960
```

```
gtcttcgaaa accagcgggt ttatcgccga agaagcgatc tgatacacgt ttatttcagg    1020
ttcc                                                                 1024

<210> SEQ ID NO 76
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0111

<400> SEQUENCE: 76
cgattggatt tagtctatac attatagggc gcaagtttgt ggatttaaga attatataaa      60
aacttgaaat atatagtttt tatgcattct cctcttgtgt aatacataaa ccaaatatga    120
gataggttaa tctgtatttc agataatatt aaattccaaa caatattttt acttgttata    180
agaaggcaat aatatctctc tgttaatgg caagtggtac caagtagtat taaactatta     240
atgcaatgga agagtactgt tggaaattat aatcctctat cacacattca aacagatctc    300
ctgaaatctt ctcttccaaa cttgtacttc tctgatccaa atgtaggctc caaaatatag    360
acatttacca tttactaagt ccacaactcc tttcttgtct ccttcaaaaa tgactcttgt    420
gtaaccacca tatgactccg acagttcggc attgccatga tgagagctta aaaattcacc    480
ttcctgagca tttcaagtct tcactcccctt agcttgacct gaaccaagat aaaatgcctt   540
tgtcgtcccg taatatccat cctgctttgg acggcatcat agttacattc gatccatcct    600
atttacaatg ttattttagt attaaaaaca tgacaataaa tttgttgtta aacatattca    660
aatacaatat gattggattt ataagtaatt gtaaatgaa atgtccttag taatatgtta     720
aaaaatacat agatacacac acgtactaaa agaggcaacg cgggagatgt cattagagga    780
agaactagga agcagagcgt tcatgcaaaa tgctaccaaa aacgttaatg caatatctca    840
actaatcagc acagtccatt tcatactgag aatgtaaaaa ccaatcagca tcgtccattt    900
tttcatctaa ttattgtta actcttaatt ggccacaact tccaaccaca tgacgctctt    960
tctattccct ttatatattc ccatctcaaa tgttcttgga gacacaaaat atcataaaca   1020
tata                                                                1024

<210> SEQ ID NO 77
<211> LENGTH: 996
<212> TYPE: DNA
<213> ORGANISM: Arabidopsis thaliana
<220> FEATURE:
<221> NAME/KEY: misc_feature
<222> LOCATION: (1)..(996)
<223> OTHER INFORMATION: Ceres Promoter YP0115

<400> SEQUENCE: 77
gtcgattgga tgatgaacat tctacatata taattattat gtttaagcac ttagacagca      60
taaattcttt ctaattatat aaatctaacc ttgttacatt gtacatctat aaattacttg    120
aagaaataac gagttctatt tcttttttaaa aattaaaaat actataccat atctcagtga   180
ttaagttgaa ccaaaaggta cggaggagaa acaagcattt gattcttcct tattttattt    240
tattcatctc tcactaatga tggtggagaa aaaagaaaa tacctaacaa acaaatatat     300
attgtcatac aaaaatattt ctatatttt agttaattag tttatattcc tcacttttca    360
gggcttatat aagaaagtga gcaaacacaa atcaaaatgc agcagcaaat actatcatca    420
cccatctcct tagttctatt ttataattcc tcttcttttt gttcatagct ttgtaattat    480
```

```
agtcttattt ctctttaagg ctcaataaga ggaggtacta ttactacact tctctctact      540
tttacttgta ttttagcatt aaaatcctaa aatccgtttt aaattcaaaa ataaacttag      600
agatgtttaa tctcgattcg gtttttcggc tttaggagaa taattatatg aaattagtat      660
ggatatcttt actagtttcc attcaaatga ttctgatttc aatctaatac tctcactctt      720
taattaaact atatgtagtg taatttcaca ctgttaaatt tctaccatgt catgtatatt      780
agagttgcat agaaaattgt aaaacatcca tttgaattcg aatgaaacaa aatgttttaa      840
aataaaattt tggttttttaa aagaaaaatc taaaactgaa ttatatcgtt taaccaagtt     900
gtaaaagtca taaaacgtag tatcttgtaa atcgctcttc cacggtccaa atagacttct     960
agtaataaac aagtaaaact aattttggtt tcttac                                996

<210> SEQ ID NO 78
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0117

<400> SEQUENCE: 78
gtcagtgagt cgattggatc acagtccttt atgataaaac aaactcataa ttattccacc       60
gacaacatgc gttttaaatt atttttttctt aaattatatt atattatatt gatatcaacc     120
tagctaaaat aattcggatg gcgaaatcgg acaatttta atagaaaaaa tgggtatgaa       180
gatagtctat gattccgttc ttagcgacta gagggacctg ctcaaatctc ccgggtgata     240
cgcgatgtca agctcaatag aaccccacaa ccgacgagac cgagaaatcc ttgatttggg     300
ctagaagatt ttgaaataaa tttaatatat tctaagtaac ttgcttaaat ttttttttcaa     360 actctaaaga cataactaac ataaagtaaa aaaaaaaaag ttaatacatg ggaagaaaaa     420
aattaaacta atgattagct ctctaacgtg tttaatctcg tatcaagttt ttttttaaaa     480
attatattgc tattaaaaca ttgtactatt gtttctattt tgtttagcta ttattcttgt     540
gaaatgaaaa gttgtgttta ttcaattact aaatggcaat atttatcttg gaaaactata     600
cctctaattg gattaggccc tagacatcct ctttagctta ttgacgttaa aattattccc     660
aaaactatta agtttagta gtttgaaaga tgcatcaaga cctactcaga taggtaaaag     720
tagaaaacta cagttagtgt gattatattt taaaatatat aaaacaatct tattaaacta     780
aatattcaag atatatactc aaatggaaga taaaaacatt tagtctgtta ccactaccag     840
cctagctagt cactaatagt cactttggaa ctgagtagat atttgcatct tgagttacca     900
tggactcaaa agtccaaaaa gagaccccga gtgaaaatgc taccaactta ataacaaaga     960
agcatttaca gcggtcaaaa agtatctata aatgtttaca caacagtagt cataagcacc    1020
attg                                                                  1024

<210> SEQ ID NO 79
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0119

<400> SEQUENCE: 79
```

```
taccaaaaat aaggagtttc caaaagatgg ttctgatgag aaacagagcc catccctctc      60
cttttcccct tcccatgaaa gaaatcggat ggtcctcctt caatgtcctc cacctactct     120
tctcttcttt cttttttct ttcttattat taaccattta attaatttcc ccttcaattt      180
cagtttctag ttctgtaaaa agaaaataca catctcactt atagatatcc atatctattt     240
atatgcatgt atagagaata aaaaagtgtg agtttctagg tatgttgagt atgtgctgtt     300
tggacaattg ttagatgatc tgtccatttt ttttcttttt cttctgtgta taaatatatt     360
tgagcacaaa gaaaaactaa taaccttctg ttttcagcaa gtagggtctt ataaccttca     420
aagaaatatt ccttcaattg aaaacccata aaccaaaata gatattacaa aaggaaagag     480
agatattttc aagaacaaca taattagaaa agcagaagca gcagttaagt ggtactgaga     540
taaatgatat agtttctctt caagaacagt ttctcattac ccaccttctc cttttgctg      600 atctatcgta atcttgagaa ctcaggtaag gttgtgaata ttatgcacca ttcattaacc     660
ctaaaaataa gagatttaaa ataaatgttt cttctttctc tgattcttgt gtaaccaatt     720
catgggtttg atatgtttct tggttattgc ttatcaacaa agagatttga tcattataaa     780
gtagattaat aactcttaaa cacacaaagt ttctttattt tttagttaca tccctaattc     840
tagaccagaa catggatttg atctatttct tggttatgta ttcttgatca ggaaaaggga     900
tttgatcatc aagattagcc ttctctctct ctctctagat atctttcttg aatttagaaa     960 tctttatta attatttggt gatgtcatat ataggatcaa                          1000

<210> SEQ ID NO 80
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0120

<400> SEQUENCE: 80
tagtttttga tttaatctac gttttctta atcataaatg ggtaattatt agttttgca       60 aaatcaaat ccaaaaattg ttctaaacac tgcaaccatt taaggcctat atcactcaga     120
aaatttctgg tgggagaact aatcgtttgt cctttctaaa tctcacatat tagaatttag    180
aattagtgtg ctacataaga atattagttc agctcggaac aactatttt tggtaaaaca     240 gagaacttaa acaaatgcat tatttatca acatgcattt tgaattgaat ataaaatttc     300
ataattgtaa agacataaat tacataaaat tttacatgaa aaaatagata tagaaagaaa    360
atgaaactaa ctgatgatat gctctctaaa ttttttaatc tcataacaag aattcaaatt    420
aattagttca tattttggt taatataaca tttacctgtc taagttggaa ctttcatttt     480
tttctgtttt gtttagtcag tattcttaat gtgaaacgga aagttgaatt tattcaaact    540
taaattcaat agcattaatt aaaggcgaaa gctattatct ctacatgtgg ttcaaactag    600
acatccaatt taattagctt attgacgttg aaatgttttc caaaactact atagtttggc    660
aatttgaaag atgcatcaga actactcaga caggtaaaag tagaacctct agctgtgtga    720 atttgtatgtt agtccataaa gaacatcttg taaacttcat acttaagata tatattacaa   780
tatatacttg aatggtagat aaaaacgatt agtctgattg ctagcatact cacaactatt    840
tggaaatgag taagatattg gcattctaga gttactacta tggagacaaa agtcgaataa   900
aagagacctc acgtgaaaat gttacgagct agtaaaaaaa gcatttacac taacggtaaa   960
aaaagtatct ataaatgttt acacaaggta gtagtcatt                           999
```

<210> SEQ ID NO 81
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0121

<400> SEQUENCE: 81

```
ttggattttt ttttttgttga gtcagcagac catctaatct ctcttttttcc accacagcct    60
gctttctatg aagcatttgg gcttacggtt gtggaatcaa tgacttgtgc actcccaacg   120
tttgctacct gtcatggtgg acccgcagag attatcgaaa acggagtttc tgggttccac   180
attgacccat atcatccaga ccaggttgca gctaccttgg tcagcttctt tgagacctgt   240
aacaccaatc caaatcattg ggttaaaatc tctgaaggag ggctcaagcg aatctatgaa   300
aggttggccc attctccttg acaggcttaa caatacaact tgtatcgctt caacaagatg   360
atggcttaat aaggattttt gcatgtatag gtacacatgg aagaagtact cagagagact   420
gcttaccctg gctggagtct atgcattctg gaaacatgtg tctaagctcg aaaggagaga   480
aacacgacgt tacctagaga tgttttactc attgaaattt cgtgatttgg ttagtgtaac   540
ccactgttat tcttttgatg tctacatcta ctttacttac attattcttt tcttcggttt   600
gcaggccaat tcaatcccgc tggcaacaga tgagaactga tcatgacagg gtaggatttt   660
atttcctgca ctttctttag atcttttgtt tgtgttatct tgaataaaaa ttgttgggtt   720
ttgtttcctt cagtggtttg attttggact tatttgtgtt aatgttgttt tggctgttct   780
cttaatatca ataacaaata aatttactgg ttggtatcta agatctaaca atagttacta   840
tttttagagg taaagacacc aaccttgtta tattggtcag agagctaaaa ccttgacttg   900
ttgggaaaac aaaactctaa tgacagaaaa tctgacatga tgccttataa ttcacagcct   960
catgttctac ataaatccta acaatagcac tttgtttct                          999
```

<210> SEQ ID NO 82
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter YP0128

<400> SEQUENCE: 82

```
gataaactga taatggaaaa gaacaaagaa accagttttt aactatttgc atatgtaatt    60
tatttgttgc aaattatatt tagttaaaat gtttcctcta tttatatata tatatatcag   120
tcaagcacta tgtataagaa atgtcaattt ataaattttt acatgtcctt taacagaaag   180
aaaatgaatt tttacatgtc attcatagag agtcactcgt ttatttctta tatagagaat   240
aacacactca catgcatatg catgcaatat gatacatttt atgacaaaga taatcaacgg   300
aaacggtcaa gacataattt gataaacaac ttgcacgatg cacagatctg atcaaatata   360
taactcttta acatatccaa aatattcaaa aagaaaaact cgatccaaac tagcaacatc   420
acgctcacgc ggtaggctaa aaatttatta atctccaaaa gtctttctta tgaacactgc   480
aaacacaaca acttgaaaag tcatataggt ttagatgatg acgcgtattg gctatcgctt   540
accggagtgg ctcataaata caataaacaa tacgtaaaag tcaaagtcaa atatatttag   600
```

| tcaactataa | ccattaatcg | ggcaaaacct | ttagctgtca | aaacaacgtg | aaaacgatat | 660 |
| ttgtatatat | catcaagaat | cagtagataa | gagaatgatt | taatcccctg | actattacaa | 720 |
| ttttggtgta | ataaacagtc | tctattggtt | tttattcttt | gttttaatttt | ctcatgacct | 780 |
| atagagagaa | ttaggtagtt | tcgaaaattg | gctaatcaac | ttttgaaaac | tactgtctac | 840 |
| tttgcttaaa | ttctctacac | ttagtttcgg | ataagataat | tgtcggacta | atagttaatc | 900 |
| ccttgacaat | ctttgatatt | ataaaaggtt | tagttaatct | cttctctata | taaatattca | 960 |
| tacaccagct | ttcaaaaata | tataatccaa | acaccaaaaa | caaa | | 1004 |

<210> SEQ ID NO 83
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter YP0137

<400> SEQUENCE: 83

| gtggcacatg | ctgaaacccc | gagcatctct | ccggaagaca | cgcgtcgttc | gctccaaaga | 60 |
| aaacagtcac | agctgccgga | gaatctccgc | cgtcttcttc | tgccaccgga | aaaactctct | 120 |
| ccaccacttt | cagtgcccac | ctcgtgttat | atccactgta | tcctcgtagc | accatatcag | 180 |
| cctaataaaa | ttttatgtat | caaattttaa | gacatagccg | aaactacact | atactagaca | 240 |
| ataataatat | gatttgtttc | ctgaaaaatt | atggtttcat | gagaaacatt | aatcatctat | 300 |
| aaaacaaatt | agctatggca | tcgaagagtt | atcaatcaaa | actgatgaat | ctttacttaa | 360 |
| tatatacaac | atatctttac | cttgcggcgg | agaagatcgg | cgagagaagc | accccagcca | 420 |
| ccgtcactaa | aggattcttc | agtgatggaa | tcaccaaaga | gaaaaacctt | ccgtctcatc | 480 |
| atcttccaca | caatcttctt | gagaaaatct | gagagataag | aaaggtgtag | tggttttgct | 540 |
| gaagtgatcg | tgtttgattt | agtaaagaaa | tgctttattt | attgttgggg | gaaacataaa | 600 |
| taaataaagt | aaaagtggat | gcactaaatg | ctttcaccca | ctaatcaccg | acctttcatg | 660 |
| gtttattgtg | aaatacactc | atagatagac | atacaatacc | ttatgtacgt | aaataacatt | 720 |
| ttatttgtcg | acacttatgt | aagtaacgca | tagattattt | tctatgtgat | tgccactctc | 780 |
| agactctcag | tttcaaccaa | taataacaat | aactacaaca | acattaatca | taaacatatg | 840 |
| ctctggttta | caattaaagc | ttagattaag | aaactgtaac | aacgttacag | aaaaaaaatg | 900 |
| ttatttacgt | tttgtaagat | tagtctctag | aatcatcacc | gttttttata | tattaatgat | 960 |
| tctttcttat | atataaaacc | tttctcgaaa | tacccatgaa | a | | 1001 |

<210> SEQ ID NO 84
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter YP0143

<400> SEQUENCE: 84

| atacaacaga | tggcagatat | cgagttaaat | acgtgaatca | gccgttacga | tattttaaaa | 60 |
| ctagaaaatt | attttaaaaat | attgcaaaat | accatttaat | ttcattgttc | ataaaaaaaa | 120 |
| gaaattcaaa | aacttaaaaa | ctgattcaaa | aatttggatt | aattctcatt | aacagtcttc | 180 |
| aacactacaa | caacatgttt | ctaatttatt | ttatatttta | ataattaaac | aatatatacg | 240 |

-continued

```
tctgcacatt gttgctccga cataatctag tataaaaata gttgcagcat atgtgaaaag      300
caagcagcat ttatcactca atacttttaa ttttatctgt tgtatgtatt aaggttttgt      360
agctttaaga aaacgcttat aatataaaat aacttctaaa agatatttca tgcgtataca      420
ataaatattt gtgaaaaaac atttcgaaaa cgtgtacaat atataaacta ttgtgttatc      480
ttttgacatt caaacaaatg ttgacaatgt aattttatcc atgatatgat tggccaatta      540
gctgcgaggt aaaaatccgt atacgagtaa aagtaagata aaatttcgca agaagatttt      600
tagcaggaaa tctaagacaa gtgtcatgaa cgtgtcaatc aacaaacgaa aaggagaatt      660
atagaatcca gattcgacgt accacattaa taaatatcaa acatttat gttattttat       720 ttttgctctg gcagttacac tctttttcat tgctccaata aaaaaatcac tcgcatgcat      780
gcatatatat acaccatagt aaactccgcc tcttcttcat tttaaagta tcagtttaca      840 ctgacacaat ccttaactat tttcctttgt tcttcttcat ctttattaca cattttttc      900 aaggtaacaa ataatctttt taagtcactt ttatactctt taaatcttag attgatatat      960
gaatgcatgt taatatttca agatttatag gtctaccaaa c                        1001
```

<210> SEQ ID NO 85
<211> LENGTH: 1003
<212> TYPE: DNA
<213> ORGANISM: Arabidopsis thaliana
<220> FEATURE:
<221> NAME/KEY: misc_feature
<222> LOCATION: (1)..(1003)
<223> OTHER INFORMATION: Ceres Promoter YP0144

<400> SEQUENCE: 85

```
aaacgttgca agattattga ttgtgagaaa gagtgctcaa ggtagtactg atttctgtaa       60
agctcacggt ggtgggaaac gatgttcttg gggagatggg aaatgtgaga aaatttgcta      120
gaggaaagaa gcggtttatg cgctgcgcat aacactatta tgtctcggga gaacaaagat      180
ggaagcaaga gcggtttgat tggaccggga ctctttagtg gccttgtttt tggctctact      240
tctgatcatt ctcagtctgg agctagcgct gtctctgatt gtactgattc tgttgaacga      300
atacagtttg agaataggca gaagaacaag aagatgatga taccgatgca ggttctagta      360
ccttcatcaa tgaaatctcc aagtaattca catgaaggag aaacaaacat ctatgacttc      420
atggttccgg aggagagagt tcacggcggt gggctagtaa tgtctttact tggtggctcc      480
attgatcgaa actgaaagcc atttatggta aaagtgtcac attctcagca aaaacctgtg      540
taaagctgta aaatgtgtgg gaatctccga atctgtttgt agccggttac gttatgctgg      600
atcaaaaact caagatttgt tggatattgt tatgctggat cggtggtgaa accacttccc      660
ggttgctaaa taaataaacg ttttttgtttt ataatctttt tcactaaacg gcagtatggg     720
cctttagtgg gcttccttta agcgaccaat acaatcgtcg caccggaatc tactaccatt      780
tataggttta ttcatgtaaa acctcggaaa atttgagagc cacaacggtc aagagacaaa      840
aacaacttga agataaaggg ataaggaagg cttcctacat gatggacaac atttctttcc      900
acacaaattc tcataataaa aatcttataa tacaaatact tacgtcataa tcattcaatc      960
tagtccccat gttttaaggt cctgtttctt gtctgataca aat                      1003
```

<210> SEQ ID NO 86
<211> LENGTH: 1004
<212> TYPE: DNA
<213> ORGANISM: Arabidopsis thaliana
<220> FEATURE:

```
<221> NAME/KEY: misc_feature
<222> LOCATION: (1)..(1004)
<223> OTHER INFORMATION: Ceres Promoter YP0156

<400> SEQUENCE: 86
ttggtttgca ttgtgaagat ttgtattaac tatagaacat tgaattgatg gtgttaagtt      60
cttacacaag cgtgcttctc ggtttgaact gtttcttttg tatgttgaat cagagcttag     120
tttataggaa ccagagtatc tacttagtca ttctctgatg ctaagtgcta aggttctacc     180
tagttgccct ctaggccctt atgttattga taacttatga agctatttga acacttgatt     240
cttaggagac ctaagttggt acagccagat agagtgtatg ttcttgttct ctatgtgaca     300
ggatcaagct gccacacata gttcaagggt atgctctgtg tgggtttgct cagattgagg     360
acaaatctat acaaggaagt agagtctttg acattttgat gttgtatgat aagaagaaga     420
aaggagagta ataagaaag agaaaaggga aacagaaaca cgtgggagaa catcccaaag      480
aggaagcaca cgcggatctt catgcaaagc tccccgattc tcccatgtgg tccctttctc     540
cctttgtccc cctcctcttt cttcttttct cattttactc cttttttttac cattatacaa    600 cgaatctttt ttatcataat ttttttggttt tggtttattt tccaataaca ctttcttggt    660
tacttcccat tctcactttt tcatataaga aactcacttt gggaaactta tgtttgagaa     720
tgacaagtct tttagagaa agtgatgtaa caaatctaaa gtgattatat aataaccttg      780
cacaatgttt ttgattttt gtaagattcg aatattaggt ttattattcg tagggaataa     840
acttactttc aaaagcgttc ataagttaat actttcatat atgatcataa gtacggacac     900
tattgttttt tgtttgtttg tgtttattct aaaagaaagt agcttttaat tgaaatgtcc     960
tcggaggcac agtttaaagt tcgagtgtaa cagtttctaa ggca                     1004

<210> SEQ ID NO 87
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0158

<400> SEQUENCE: 87
ttattagatt aatagattgc attgcattgc ttgtgctttc aatttacaaa ttgtctccca      60
actccatcga cacatctctt tttgtgtata taagattcag acttgttata ttttttttat    120
aaatatgtta ttagcatctt aagttaaatt gattttttat atctgcatta aggattacac    180
gactatattt gcgattgtgt gttggttaaa atataattta ggattgtctt taactacatt    240
taggattata tgactatatt tggttaaata taaaatctag ctgtgattat tagtattcaa    300
aaataagtag cctaaccaat taaaacaacg gctattgggg caaattagaa catttttagtg   360 tgtccaaaat ataatggtca ttaggtcata ttcctcctag cttcatcgca gcataattga    420
atgattgcct tatttagaag agcttttcca ctttcccaaa atctaggtgg gatcttttg     480 ttttgaccctt cattttttctt gtttaccatt tttagctaaa ttatttacga ttacaaagaa    540
tatcaaaagt tggatcataa tacaatttat agacttactg tagaaaattc gtatgtacaa    600
gtacaacaaa ttcttcataa taaattttga aaattctatt acaatgttg taagaaatag     660 aatttgaaat atatataaac taaggagaaa aaaaagaga acatgcattg ctctagtcag    720
agtggaccaa catcaacgag ataagataac ataaaaacca actcaccata actaaaaaca    780
tcccaagaga tccaacgatt catatcaaac acaaaaacat cgaacgatca gatttaaacc    840
```

```
atctctggta tctccaaaac acaaacactt tttttttttct tttgtctgaa tggaacaaaa      900
gcatgcgaca tctctgtgtc tttatcttct ctctcctctt cttgaaaaac tgaacccttta     960 attctttctt cacatctcct ttagctttct gaagctgcta                           1000
```

<210> SEQ ID NO 88
<211> LENGTH: 1005
<212> TYPE: DNA
<213> ORGANISM: Arabidopsis thaliana
<220> FEATURE:
<221> NAME/KEY: misc_feature
<222> LOCATION: (1)..(1005)
<223> OTHER INFORMATION: Ceres Promoter YP0188

<400> SEQUENCE: 88

```
gattggtatg aaatttcgga gaccaacaaa aaaaacttta ttgagcttgg agtgaagcta      60
tatatatggg gcaagatcat aatatgttta tatcggcctt ttcgttaact gaaaataata    120
gttttgagaa atatatcaaa tggtaaacag acatcatctt tgaaaaatac catcaatgaa    180
gttaatattg ttattggcat atggtttacc catcttaatt ttaatgcaac caaacaaaca    240
agaaacaaaa actgtataag atacaaggtg ttttacgatt ttccgtctta aaaccgaaat    300 attttttgttc ctacgacttt aaacggactt tgcttaagtt gtgtgcatgt aagctcgtcg    360
tccctcgatt gtcatcaaca ttcaccaata tcagcctcta tcacacgagt gaaggtggtg    420
attcggctta atgaaaacag agaaatattt caatatgatt cctattaaat tttaaatctt    480
ttttctcaat ctctagattt tcattaaaag catcatgatt ttttttccact atgttcatat    540 atctctatca cagtttttagg tacattgtag aaattggata agatacgtca tacgtctaac    600 atgaattttgg tctagcaagg aaggtttgag ataataagtg aaaagaaaac acaagataat    660
aaattataat ttataaatgc tttatagtat tgaaaaataa gatgattttt ttttttttta    720
ataccggatt ggctgatcca cttatgatga ctcaaatgtt attaagtttc aagacaatttt    780 atgatgacac aaatcacaat gagtcaatag tagccacgaa gccagaaaaa aaaaatgtac    840
tacaaaaaga taatgatagt acaaaatgat acgtcgtact gccacatgta cgacacaact    900
cgattaccaa aaagcagagc catccaacca taaaactcaa aacacacaga ttccactggc    960
gtgtgctctc ctcacttcac tcgtccttga aacttgaggt actga                   1005
```

<210> SEQ ID NO 89
<211> LENGTH: 1002
<212> TYPE: DNA
<213> ORGANISM: Arabidopsis thaliana
<220> FEATURE:
<221> NAME/KEY: misc_feature
<222> LOCATION: (1)..(1002)
<223> OTHER INFORMATION: Ceres Promoter YP0190

<400> SEQUENCE: 89

```
taaatagtga cattggtaag aagaaaaaaa acactattaa atagtgaaaa aatggtttat      60
aactctctta attaacatta cttattattg ctagcaccta aaatctccca caaaatatttt    120 gttgtaaaac acaaatttac aaaatgatt tgttttttaaa ttagtaacac atgttcatat    180
atacgttaat aagaacatac cctatatgat tttatataaa aaaatttctt tgagacgtct    240 tattctttttt tctttaataa tatgcaattg tgagagtttg gatttgaatg gtagcattag    300
aagcaaactt gaaccaaaca tatttcatga agtcaaactt gaaccaatgt gatcactaat    360
cacagtgttc gcagtgtaag gcatcagaaa atagaagaag ggacatagct atgaatcata    420
```

```
taatcttgac acatgtttta taggttttag gtgtgtatgc taacaaaaaa tgagacagct      480
ttcttctaat agacttaata tttgggctaa atgtaccaca gttgtgaatt tcttacaaaa      540
atgggccgag ctacaaaaaa ctacaggccc actctcaact cttatcaaac gacagcgttt      600
tactttttta aaagcacaca ctttttgttt ggtgtcggtg acggtgagtt tcgtccgctc      660
ttcctttaaa ttgaagcaac ggttttgatc cgatcaaatc caacggtgct gattacacaa      720
agcccgagac gaaaacgttg actattaagt taggttttaa tctcagccgt taatctacaa      780
atcaacggtt ccctgtaaaa cgaatcttcc ttccttcttc acttccgcgt cttctctctc      840
aatcacctca aaaaaatcga tttcatcaaa atattcaccc gcccgaattt gactctccga      900
tcatcgtctc cgaatctaga tcgacgagat caaaaccta gaaatctaaa tcggaatgag      960
aaattgattt tgatacgaat tagggatctg tgtgttgagg ac                       1002
```

<210> SEQ ID NO 90
<211> LENGTH: 995
<212> TYPE: DNA
<213> ORGANISM: Arabidopsis thaliana
<220> FEATURE:
<221> NAME/KEY: misc_feature
<222> LOCATION: (1)..(995)
<223> OTHER INFORMATION: Ceres Promoter YP0212

<400> SEQUENCE: 90

```
agtcgattgg tacactctta atttaattag agtaagagat caacaaaaat atagaatttt       60
ctttatatcg aagtgctacg accttatata tatagaaaaa aaagcatagg tgaatctcta      120
aattgagatt gtgctgtagt aaacatatta agttttttagt ttttttaaga aatgaatctt      180
tttgttgatt aattcaaact agtagtcatt aagattccgg agattccaat ttagaaaagt      240
caaagattca aagaacaagt ccaggtccac atgttgaatc cgattcatca tccactcatc      300
cttcatatct tcctccaccg tctccgccca aaaaatcaat aacaataaaa atcctaaaa       360 aaacatattt gattttgaaa aactttatc atatattata ttaattaaat agttatccga       420
tgactcatcc tatggtcagg gccttgctgt ctctgacgtc cttaattatc attattttta      480
aatttgtctc tctcagaaaa ttacgccaca atcttcctct ttccctttc cgaaaacagc      540 taatatttgt ggacctaaac taaataacgt agcctctaga ttttatataa ttactaatac      600
tatatgctac tacttgttat tatttactcc aatcatatat gataccaatc aagaatcact      660
acataagtag aaaactttgc aatgagtcca ttaattaaaa ttaagaataa acttaaaatt      720
ttatggtatt ttaagattcc ctttggattg taatgacaag aaatcagcaa attagtcgta      780
actcgtaaga ataaacaaga tcaatttttta ctttctttac aaagattccg ttgtaatttt      840
agaaattttt ttttgtcact gtttttttat agattaattt atctgcatca atccgattaa      900
gaagtgtaca catgggcatc tatatatatc taacaggtaa aacgtgtatg tacatgcata      960
aggttttacg tgcttctata aatatatgtg gcagt                                995
```

<210> SEQ ID NO 91
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0214

<400> SEQUENCE: 91

```
ccagtcgatt ggcgcctcgc atgcctatca tatttaaccg tcaataatgg atttggcggt       60
```

-continued

```
tttggtaggc cgggtcaacc ggattaaaag aaaacggttt ggagtccttc cttgcaattg    120
aattttcaca cattcgggtt ttgtgatttc tctgtcataa tgggcccggc acatatggtt    180
cataacccat gtgggcctat ggtataattt ttccaattaa aactattgtt aggtcgataa    240
aacaaaaaac aataaaaacg agtggaatac acataccaaa aagaatgtga tgaacattag    300
taatttattt ttgatggtta atgaaaaaca aaataaatgc atcttggcat cttccgttgg    360
aaagcgcaaa tagggcagat tttcagacag atatcactat gatgggggt gagagaaaga    420 aaacgaggcg tacctaatgt aacactactt aattagtcgt tagttatagg acttttttt    480 tgtttgggcc tagttatagg atcataaggt aaaaatgaag aatgaatatt agattagtag    540
gagctaatga tggagttaag tatgcacgtg taagaactgg gaagtgaaac ctcctgtatg    600
gtgaagaaac tatacaacaa agcccttgt tggtgtatac gtattaattt ttattctttt    660
atcacaagcg atacgtatct taagacataa taaatatata tcttactcat aataaatatc    720
ttaagatata tatacagtat acacctgtat atatataata aataggcata tagtagaaat    780
taatatgagt tgttgttgtt gcaaatatat aaatcaatca aaagatttaa acccaccat    840 tcaatcttgg taagtaacga aaaaaagggg aagcaagaag aaccacagaa aaggggggcta    900 acaactagac acgtagatct tcatctgccc gtccatctaa cctaccacac tctcatcttc    960 ttttttcccgt gtcagtttgt tatataagct ctcactctcc ggtatatttc cccattgcac   1020
tgga                                                                 1024
```

<210> SEQ ID NO 92
<211> LENGTH: 911
<212> TYPE: DNA
<213> ORGANISM: Arabidopsis thaliana
<220> FEATURE:
<221> NAME/KEY: misc_feature
<222> LOCATION: (1)..(911)
<223> OTHER INFORMATION: Ceres Promoter YP0263

<400> SEQUENCE: 92

```
atctagctgt ggattccacc aaaattctgg cagggccatg atctaaaaac tgagactgcg     60
cgtgttgttt tgcagtgatt tgtatttcat atttgcacca tcctacacag tccacttggt    120
atcgtaacca aacataagga gaacctaatt acattattgt tttaatttcg tcaaactggt    180 tttaccttt tagttacata gttgattctt catttgtttt agtagttatg gagcacaata    240
atgtgcaaca aagaaagatc atagtggatt aatatgttga gaggtcagaa attcttggtt    300
aacaaaaaaa agttacaagg actgagattt tgggtgggag aaagccatag cttttaaaac    360
atgattgaac ttaaaagtga tgttatggtt tgaggggaaa aaggttgatg tcaactaaga    420
tagttgaagt aatgtcttaa actaaagtaa accaccggtc caaccgtggt ccggaagcat    480
ctctggtatg atttatccta aaaatcaaaa tagtagaaac atactttaaa tatatacatt    540
gatcggacga aaattgtaaa ctagtatagt ttcaaaaact agttgaacag gttatgtacc    600
ttaaacattt atttcaaact taaacactaa agaacatata tgaatagaag tttatataaa    660
ttactatata tctaccataa atctcttata attatgatgt cacgatgagg aagtgttgaa    720
acgttaaaat gccaaaatat aagcatgcga cggaattttg gcagaagatt gtagagttgt    780
aatctgtcgc aatcattact cgtgctagca ttttccattt tcccttcatt tgtggataac    840
gcacgatata acattctaca caccaacaag attctataaa aacgcaaagg ttgtctccat    900
agaatatcgt c                                                         911
```

```
<210> SEQ ID NO 93
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0275

<400> SEQUENCE: 93
aaacattaat atgtagtaac tatgggcgta tgctttactt tttaaaatgg gcctatgcta    60
taattgaatg acaaggatta aacaactaat aaaattgtag atgggttaag atgacttatt   120
tttttactta ccaatttata aatgggcttc gatgtactga aatatatcgc gcctattaac   180
gaggccattc aacgaatgtt ttaagggccc tatttcgaca ttttaaagaa cacctaggtc   240
atcattccag aaatggatat tataggattt agataatttc ccacgtttgg tttatttatc   300
tattttttga cgttgaccaa cataatcgtg cccaaccgtt tcacgcaacg aatttatata   360
cgaaatatat atattttca aattaagata ccacaatcaa acagctgtt gattaacaaa   420 gagatttttt ttttttggtt ttgagttaca ataacgttag aggataaggt ttcttgcaac   480
gattaggaaa tcgtataaaa taaaatatgt tataattaag tgttttattt tataatgagt   540
attaatataa ataaaacctg caaaggata gggatattga ataataaaga gaacgaaag    600 agcaattta cttctttata attgaaatta tgtgaatgtt atgtttacaa tgaatgattc   660
atcgttctat atattgaagt aaagaatgag tttattgtgc ttgcataatg acgttaactt   720
cacatataca cttattacat aacatttatc acatgtgcgt cttttttttt ttttactttg   780
taaaatttcc tcacttttaa gactttata acaattacta gtaaaataaa gttgcttggg   840
gctacaccct ttctccctcc aacaactcta tttatagata acattatatc aaaatcaaaa   900
catagtccct ttcttctata aaggtttttt cacaaccaaa tttccattat aaatcaaaaa   960
ataaaaactt aattagtttt tacagaagaa agaaaaca                            999

<210> SEQ ID NO 94
<211> LENGTH: 981
<212> TYPE: DNA
<213> ORGANISM: Arabidopsis thaliana
<220> FEATURE:
<221> NAME/KEY: misc_feature
<222> LOCATION: (1)..(981)
<223> OTHER INFORMATION: Ceres Promoter YP0285

<400> SEQUENCE: 94
gggattatat atgatagacg attgtatttg cgggacattg agatgtttcc gaaaatagtc    60
atcaaatatc aaaccagaat ttgatgtgaa aacactaatt aaaacatata attgacaact   120
agactatatc atttgttaag ttgagcgttg aaagaaaatg aaagagtgta gactgtagta   180
cgtatgagtt tcccaaaaga tggtgcttga atattattgg gaagagactt tggttggttc   240
ggttgaatga agatttttac ctgccatgtt gatagagaaa ggcaaataaa tgtagggtc    300 gatgtctaac gtaagactg atcaaccaa gagtcctcct cctcgtcttc accaaaaaaa    360
aagagtcctc ctcgtggaaa cttatttctt ctccagccaa gatctcatct catctcttca   420
ctctatgaaa tataaaggaa tcttatggtt tttctaaaaa ctatagtacg tctatatacc   480
aaaggaaaca atataaaatc agttaatctg ataaatttg agtaaataat aaagttaact   540
ttgtacttac ctatatcaaa ctaattcaca aaataaagta ataataacaa agaattttta   600
gtagatccac aatatacaca cacactatga gaaatcataa tagagaattt taatgatttt   660
```

```
gtctaactca tagcaacaag tcgctttggc cgagtggtta aggcgtgtgc ctgctaagta        720
catgggctct gcccgcgaga gttcgaatct ctcaggcgac gtttcttttg ttttcggcca        780
taaaggaaaa agcccaatta acacgtctcg cttataagcc cataaagcaa acaatgggct        840
gtctctgtct cactcacaca cgcgttttcc tacttttga ctatttttat aaccggcggg         900
tctgacttaa ttagggtttt ctttaataat cagacactct ctcactcgtt tcgtcaacat        960
tgaacacaga caaaaccgcg t                                                  981

<210> SEQ ID NO 95
<211> LENGTH: 996
<212> TYPE: DNA
<213> ORGANISM: Arabidopsis thaliana
<220> FEATURE:
<221> NAME/KEY: misc_feature
<222> LOCATION: (1)..(996)
<223> OTHER INFORMATION: Ceres Promoter YP0286

<400> SEQUENCE: 95
gaaaacaatc ataggttacg ctattatcat cgaaaggtat gtgatgcata ttcccattga         60
accagatttc catatatttt atttgtaaag tgataatgaa tcacaagatg attcaatatt        120
aaaaatgggt aactcacttt gacgtgtagt acgtggaaga atagttagct atcacgcata        180
catatatcta tgaataagtg tgtatgacat aagaaactaa atatttacc taaagtccag         240 ttactcatac tgatttcatg catatatgta ttatttattt attttttaata aagaagcgat       300 tggtgttttc atagaaatca tgatagattg ataggtattt cagttccaca aatctagatc       360
tgtgtgctat acatgcatgt attaatttt tccccttaaa tcatttcagt tgataatatt        420
gctctttgtt ccaactttag aaaaggtatg aaccaacctg acgattaaca agtaaacatt       480
aattaatctt tatatgagat aaaaccgagg atatatatga ttgtgttgct gtctattgat       540
gatgtgtcga tattatgctt gttgtaccaa tgctcgagcc gagcgtgatc gatgccttga      600
caaactatat atgtttcccg aattaattaa gttttgtatc ttaattagaa taacattttt      660
atacaatgta atttctcaag cagacaagat atgtatccta tattaattac tatatatgaa      720
ttgccgggca cctaccagga tgtttcaaat acgagagccc attagtttcc acgtaaatca      780
caatgacgcg acaaaatcta gaatcgtgtc aaaactctat caatacaata atatatattt      840
caagggcaat ttcgacttct cctcaactca atgattcaac gccatgaatc tctatataaa      900
ggctacaaca ccacaaagga tcatcagtca tcacaaccac attaactctt caccactatc      960
tctcaatctc tcgtttcatt tcttgacgcg tgaaaa                                 996

<210> SEQ ID NO 96
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0337

<400> SEQUENCE: 96
taattttttt attttggaa ctaacactta ttagtttagg tttccatcac ctatttaatt         60
cgtaattctt atacatgcat ataatagaga tacatatata caaatttatg atcatttttg       120
cacaacatgt gatctcattc attagtatgc attatgcgaa aacctcgacg cgcaaaagac       180
acgtaatagc taataatgtt actcatttat aatgattgaa gcaagacgaa aacaacaaca      240
```

| | |
|---|---|
| tatatatcaa attgtaaact agatatttct taaaagtgaa aaaaaacaaa gaaatataaa | 300 |
| ggacaatttt gagtcagtct cttaatatta aaacatatat acataaataa gcacaaacgt | 360 |
| ggttacctgt cttcatgcaa tgtggactt agtttatcta atcaaaatca aaataaaagg | 420 |
| tgtaatagtt ctcgtcattt ttcaaatttt aaaaatcaga accaagtgat ttttgtttga | 480 |
| gtattgatcc attgttaaa caatttaaca cagtatatac gtctcttgag atgttgacat | 540 |
| gatgataaaa tacgagatcg tctcttggtt ttcgaatttt gaactttaat agttttcttt | 600 |
| tttagggaaa cttaatagt tgtttatcat aagattagtc acctaatggt tacgttgcag | 660 |
| taccgaacca atttttacc cttttttcta aatgtggtcg tggcataatt tccaaaagag | 720 |
| atccaaaacc cggtttgctc aactgataag ccggtcggtt ctggtttgaa aaacaagaaa | 780 |
| taatctgaaa gtgtgaaaca gcaacgtgtc tcggtgtttc atgagccacc tgccacctca | 840 |
| ttcacgtcgg tcattttgtc gttcacggt tcacgctcta gacacgtgct ctgtccccac | 900 |
| catgactttc gctgccgact cgcttcgctt tgcaaactca aacatgtgtg tatatgtaag | 960 |
| tttcatccta ataagcatct cttaccacat taattaaaaa | 1000 |

```
<210> SEQ ID NO 97
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0356

<400> SEQUENCE: 97
```

| | |
|---|---|
| ttagttcatt gaaacgtcaa cttttactt gcaaccactt tgtaggacca ttaactgcaa | 60 |
| aataagaatt ctctaagctt cacaaggggt tcgtttggtg ctataaaaac attgttttaa | 120 |
| gaactggttt actggttcta taatctata atccaaata tgaagtatgg caataataat | 180 |
| aacatgttag cacaaaaaat actcattaaa ttcctaccca aaaaaatct ttatatgaaa | 240 |
| ctaaaactta tatacacaat aatagtgata caaagtaggt cttgatattc aactattcgg | 300 |
| gattttctgg tttcgagtaa ttcgtataaa aggtttaaga tctattatgt tcactgaaat | 360 |
| cttaactttg ttttgtttcc agttttaact agtagaaatt gaaatttta aaaattgtta | 420 |
| cttacaataa aatttgaatc aatatcctta atcaaggat cttaagacta gcacaattaa | 480 |
| aacatataac gtagaatatc tgaaataact cgaaaatatc tgaactaagt tagtagtttt | 540 |
| aaaatataat cccggtttgg accgggcagt atgtacttca atacttgtgg gttttgacga | 600 |
| ttttggatcg gattgggcgg gccagccaga ttgatctatt acaaatttca cctgtcaacg | 660 |
| ctaactccga acttaatcaa agattttgag ctaaggaaaa ctaatcagtg atcacccaaa | 720 |
| gaaacattc gtgaataatt gtttgctttc catggcagca aaacaaatag gacccaaata | 780 |
| ggaatgtcaa aaaaagaaa gacacgaaac gaagtagtat aacgtaacac acaaaaataa | 840 |
| actagagata ttaaaaacac atgtccacac atggatacaa gagcatttaa ggagcagaag | 900 |
| gcacgtagtg gttagaaggt atgtgatata attaatcggc ccaaatagat tggtaagtag | 960 |
| tagccgtcta tatcatccat actcatcata acttcaacct | 1000 |

```
<210> SEQ ID NO 98
<211> LENGTH: 1000
<212> TYPE: DNA
<213> ORGANISM: Arabidopsis thaliana
<220> FEATURE:
<221> NAME/KEY: misc_feature
```

<222> LOCATION: (1)..(1000)
<223> OTHER INFORMATION: Ceres Promoter YP0374

<400> SEQUENCE: 98

```
aagacacccg taaatgttgt catgtagaag aaactagaaa cgttaaacgc atcaaatcaa      60
gaaattaaat tgaaggtaat ttttaacgcc gcctttcaaa tattcttcct aggagaggct     120
acaagacgcg tatttctttc gaattctcca aaccattacc attttgatat ataataccga     180
catgccgttg ataaagtttg tatgcaaatc gttcattggg tatgagcaaa tgccatccat     240
tggttcttgt aattaaatgg tccaaaaata gtttgttccc actactagtt actaatttgt     300
atcactctgc aaaataatca tgatataaac gtatgtgcta tttctaatta aaactcaaaa     360
gtaatcaatg tacaatgcag agatgaccat aaaagaacat aaaacacta cttccactaa      420
atctatgggg tgccttggca aggcaattga ataaggagaa tgcatcaaga tgatatagaa     480
aatgctattc agtttataac attaatgttt tggcggaaaa ttttctatat attagacctt     540
tctgtaaaaa aaaaaaaatg atgtagaaaa tgctattatg tttcaaaaat ttcgcactag     600
tataatacgg aacattgtag tttacactgc tcattaccat gaaaaccaag gcagtatata     660
ccaacattaa taaactaaat cgcgatttct agcaccccca ttaattaatt ttactattat     720
acattctctt tgcttctcga ataataaac ttctctatat cattctacat aataaataag      780
aaagaaatcg acaagatcta aatttagatc tattcagctt tttcgcctga aagccaaaa      840
ttgtgaatag aagaaagcag tcgtcatctt cccacgtttg gacgaaataa aacataacaa    900
taataaaata ataaatcaaa tatataaatc cctaatttgt ctttattact ccacaatttt    960
ctatgtgtat atatataccc acctctctct tgtgtatttg                         1000
```

<210> SEQ ID NO 99
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter YP0377

<400> SEQUENCE: 99

```
tataaaccat tcctataaca ccatatttaa acataacaat gaattgcttg gatttcaaac      60
tttattaaat ttggatttta aatttttaat tgattgaatt ataccccctt aattggataa     120
attcaaatat gtcaactttt tttttgtaag atttttttat ggaaaaaaaa attgattatt     180
cactaaaaag atgacaggtt acttataatt taatatatgt aaaccctaaa agaagaaaa     240
tagtttctgt tttcacttta ggtcttatta tctaaacttc tttaagaaaa tcgcaataaa     300
ttggtttgag ttctaacttt aaacacatta atatttgtgt gctatttaaa aataatttta    360
caaaaaaaaa aacaaattga cagaaaatat caggttttgt aataagatat ttcctgataa    420
atatttaggg aatataacat atcaaaagat tcaaattctg aaaatcaaga atggtagaca    480
tgtgaaagtt gtcatcaata tggtccactt tcctttgctc tataacccaa aattgaccct    540
gacagtcaac ttgtacacgc ggccaaacct ttttataatc atgctattta tttccttcat    600
ttttattcta tttgctatct aactgatttt tcattaacat gataccagaa atgaatttag    660
atggattaat tcttttccat ccacgacatc tggaaacact tatctcctaa ttaaccttac    720
ttttttttta gtttgtgtgc tccttcataa aatctatatt gtttaaaaca aggtcaata    780
aatataaata tggataagta taataaatct ttattggata tttcttttttt taaaaagaa   840
```

```
ataaatctttt tttggatatt ttcgtggcag catcataatg agagactacg tcgaaaccgc    900
tggcaaccac ttttgccgcg tttaatttct ttctgaggct tatataaata gatcaaaggg    960
gaaagtgaga tataatacag acaaaacaag agaaaaga                            998
```

<210> SEQ ID NO 100
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0380

<400> SEQUENCE: 100

```
acaagtacca ttcacttttt tactttcaa tgtatacaat catcatgtga taaaaaaaaa      60
aatgtaacca atcaacacac tgagatacgg ccaaaaaatg gtaatacata aatgtttgta    120
ggttttgtaa tttaaatact ttagttaagt tatgatttta ttattttgc ttatcactta    180 tacgaaatca tcaatctatt ggtatctctt aatcccgctt tttaatttcc accgcacacg    240
caaatcagca aatggttcca gccacgtgca tgtgaccaca tattgtggtc acagtactcg    300 tcctttttt ttcttttgta atcaataaat ttcaatccta aaacttcaca cattgagcac    360
gtcggcaacg ttagctccta aatcataacg agcaaaaaag ttcaaattag ggtatatgat    420
caattgatca tcactacatg tctacataat taatatgtat tcaaccggtc ggtttgttga    480
tactcatagt taagtatata tgtgctaatt agaattagga tgaatcagtt cttgcaaaca    540
actacggttt catataatat gggagtgtta tgtacaaaat gaaagaggat ggatcattct    600
gagatgttat gggctcccag tcaatcatgt tttgctcgca tatgctatct tttgagtctc    660
ttcctaaact catagaataa gcacgttggt tttttccacc gtcctcctcg tgaacaaaag    720
tacaattaca ttttagcaaa ttgaaaataa ccacgtggat ggaccatatt atatgtgatc    780
atattgcttg tcgtcttcgt tttctttaa atgtttacac cactacttcc tgacacgtgt    840
ccctattcac atcatccttg ttatatcgtt ttacttataa aggatcacga acaccaaaac    900
atcaatgtgt acgtcttttg cataagaaga aacagagagc attatcaatt attaacaatt    960
acacaagaca gcgagattgt aaaagagtaa gagagagag                           999
```

<210> SEQ ID NO 101
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0381

<400> SEQUENCE: 101

```
cacggtcaaa gtattgctaa catggtcatt acattgaaaa agaaaattaa ttgtctttac     60
tcatgtttat tctatacaaa taaaaatatt aaccaaccat cgcactaaca aaatagaaat    120
cttattctaa tcacttaatt gttgacaatt aaatcattga aaaatacact taaatgtcaa    180
atattcgttt tgcatacttt tcaatttaaa tacatttaaa gttcgacaag ttgcgtttac    240
tatcatagaa aactaaatct cctaccaaag cgaaatgaaa ctactaaagc gacaggcagg    300
ttacataacc taacaaatct ccacgtgtca attaccaaga gaaaaaaaga gaagataagc    360
ggaacacgtg gtagcacaaa aaagataatg tgatttaaat taaaaaacaa aaacaaagac    420
acgtgacgac ctgacgctgc aacatcccac cttacaacgt aataaccact gaacataaga    480
```

```
cacgtgtacg atcttgtctt tgttttctcg atgaaaacca cgtgggtgct caaagtcctt      540
gggtcagagt cttccatgat tccacgtgtc gttaatgcac caaacaaggg tactttcggt      600
attttggctt ccgcaaatta gacaaaacag cttttttgttt gattgatttt tctcttctct     660
ttttccatct aaattctctt tgggctctta atttcttttt gagtgttcgt tcgagatttg      720
tcggagattt tttcggtaaa tgttgaaatt tgtgggatt ttttttttatt tctttattaa      780 actttttttt attgaattta taaaaaggga aggtcgtcat taatcgaaga aatggaatct      840
tccaaaattt gatattttgc tgttttcttg ggatttgaat tgctctttat catcaagaat      900
ctgttaaaat ttctaatcta aaatctaagt tgagaaaaag agagatctct aatttaaccg      960
gaattaatat tctccgaccg aagttattat gttgcaggct                           1000
```

<210> SEQ ID NO 102
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0384

<400> SEQUENCE: 102

```
tttaaaaaat tggataaaac accgataaaa attcacattt gcaaattta ttcagtcgga        60 atatatattt gaaacaagtt ttgaaatcca ttggacgatt aaaattcatt gttgagagga      120
taaatatgga tttgttcatc tgaaccatgt cgttgattag tgattgacta ccatgaaaaa      180
tatgttatga aaagtataac aactttttgat aaatcacatt tattaacaat aaatcaagac     240
aaaatatgtc aacaataata gtagtagaag atattaattc aaattcatcc gtaacaacaa      300
aaaatcatac cacaattaag tgtacagaaa aaccttttgg atatatttat tgtcgctttt      360
caatgatttt cgtgaaaagg atatatttgt gtaaaataag aaggatcttg acgggtgtaa      420
aaacatgcac aattcttaat ttagaccaat cagaagacaa cacgaacact tctttattat      480
aagctattaa acaaaatctt gcctatttg cttagaataa tatgaagagt gactcatcag       540
ggagtggaaa atatctcagg atttgctttt agctctaaca tgtcaaacta tctagatgcc      600
aacaacacaa agtgcaaatt cttttaatat gaaaacaaca ataatattc taatagaaaa       660 ttaaaagggg aaataaaata ttttttttaaa atatacaaaa gaagaaggaa tccatcatca     720
aagttttata aaattgtaat ataatacaaa cttgtttgct tccttgtctc tccctctgtc      780
tctctcatct ctcctatctt ctccatatat acttcatctt cacacccaaa actccacaca      840
aaatatctct ccctctatct gcaaattttc caaagttgca tcctttcaat ttccactcct      900
ctctaatata attcacattt tcccactatt gctgattcat tttttttgt gaattatttc       960 aaacccacat aaaaaatct ttgtttaaat taaaaacca                              999
```

<210> SEQ ID NO 103
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter YP0385

<400> SEQUENCE: 103

```
actcaacaat aggacaagcc aaaaaaattc caattattgt gttactctat tcttctaaat       60
```

```
ttgaacacta atagactatg acatatgagt atataatgtg aagtcttaag atattttcat      120
gtgggagatg aataggccaa gttggagtct gcaaacaaga agctcttgag ccacgacata      180
agccaagttg atgaccgtaa ttaatgaaac taaatgtgtg tggttatata ttagggaccc      240
atggccatat acacaatttt tgtttctgtc gatagcatgc gtttatatat atttctaaaa      300
aaactaacat atttactgga tttgagttcg aatattgaca ctaatataaa ctacgtacca      360
aactacatat gtttatctat atttgattga tcgaagaatt ctgaactgtt ttagaaaatt      420
tcaatacact taacttcatc ttacaacggt aaaagaaatc accactagac aaacaatgcc      480
tcataatgtc tcgaaccctc aaactcaaga gtatacattt tactagatta gagaatttga      540
tatcctcaag ttgccaaaga attggaagct tttgttacca aacttagaaa cagaagaagc      600
cacaaaaaaa gacaagggga gttaaagatt gaagtgatgc atttgtctaa gtgtgaaagg      660
tctcaagtct caactttgaa ccataataac attactcaca ctcccttttt ttttcttttt      720
ttttcccaaa gtaccctttt taattccctc tataacccac tcactccatt ccctcttttct      780 gtcactgatt caacacgtgg ccacactgat gggatccacc tttcctctta cccacctccc      840
ggtttatata aacccttcac aacacttcat cgctctcaaa ccaactctct cttctctctt      900
ctctcctctc ttctacaaga agaaaaaaaa cagagccttt acacatctca aaatcgaact      960
tactttaacc accaaatact gattgaacac acttgaaa                             998

<210> SEQ ID NO 104
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0396

<400> SEQUENCE: 104
catagtaaaa gtgaatttaa tcatactaag taaaataaga taaaacatgt tatttgaatt       60
tgaatatcgt gggatgcgta tttcggtatt tgattaaagg tctggaaacc ggagctccta      120
taacccgaat aaaaatgcat aacatgttct tccccaacga ggcgagcggg tcagggcact      180
agggtcattg caggcagctc ataaagtcat gatcatctag gagatcaaat tgtatgtcgg      240
ccttctcaaa attacctcta agaatctcaa acccaatcat agaaccctcta aaaagacaaa      300 gtcgtcgctt tagaatgggt tcggtttttg gaaccatatt tcacgtcaat ttaatgttta      360
gtataatttc tgaacaacag aattttggat ttatttgcac gtatacaaat atctaattaa      420
taaggacgac tcgtgactat ccttacatta agtttcactg tcgaaataac atagtacaat      480
acttgtcgtt aatttccacg tctcaagtct ataccgtcat ttacggagaa agaacatctc      540
tgtttttcat ccaaactact attctcactt tgtctatata tttaaaatta agtaaaaaag      600
actcaatagt ccaataaaat gatgaccaaa tgagaagatg gttttgtgcc agattttagg      660
aaaagtgagt caaggtttca catctcaaat ttgactgcat aatcttcgcc attaacaacg      720
gcattatata tgtcaagcca attttccatg ttgcgtactt ttctattgag gtgaaaatat      780
gggtttgttg attaatcaaa gagtttgcct aactaatata actacgactt tttcagtgac      840
cattccatgt aaactctgct tagtgtttca tttgtcaaca atattgtcgt tactcattaa      900
atcaaggaaa aatatacaat tgtataattt tcttatattt taaaattaat tttgatgtat      960
taccccttta taaataggct atcgctacaa caccaataac                           1000
```

<210> SEQ ID NO 105
<211> LENGTH: 1514
<212> TYPE: DNA
<213> ORGANISM: Arabidopsis thaliana
<220> FEATURE:
<221> NAME/KEY: misc_feature
<222> LOCATION: (1)..(1514)
<223> OTHER INFORMATION: Ceres Promoter p13879

<400> SEQUENCE: 105

```
tttcgatcct cttctttttt aggtttcttg atttgatgat cgccgccagt agagccgtcg      60
tcggaagttt cagagattaa aaccatcacc gtgtgagttg gtagcgaatt aacggaaagt     120
ctaagtcaag attttttaaa aagaaattta tgtgtgaaaa gaagccgttg tgtatattta     180
tataatttag aaaatgtttc atcattttaa ttaaaaaatt aataatttgt agaagaaaga     240
agcatttttt atacataaat catttacctt ctttactgtg ttttttcttca cttacttcat     300
ttttacttt ttacaaaaaa gtgaaaagta aattacgtaa ttggtaacat aaattcactt     360
taaatttgca tatgttttgt tttcttcgga aactatatcg aaaagcaaac ggaaagaact     420
tcacaaaaaa ccctagctaa ctaaagacgc atgtgttctt cttattcttc atatatcctc     480
tgtttcttgt gttctgtttt gagtcttaca ttttcaatat ctgactctga ttactatatc     540
taaaagggaa catgaagaac ttgagaccat gttaaactgt acaatgcctt caaacatggc     600
taactaaaga tacattagat ggctttacag tgtgtaatgc ttattatctt taggtttttt     660
aaatcccttg tattaagtta tttaccaaat tatgttcttg tactgcttat tggcttggtt     720
gttgtgtgct ttgtaaacaa caccttttggc tttatttcat cctttgtaaa cctactggtc     780
tttgttcagc tcctcttgga agtgagtttg tatgcctgga acgggtttta atggagtgtt     840
tatcgacaaa aaaaaaatgt agcttttgaa atcacagaga gtagtttat attcaaatta      900
catgcatgca actaagtagc aacaaagttg atatggccga gttggtctaa ggcgccagat     960
taaggttctg gtccgaaagg gcgtgggttc aaatcccact gtcaacattc tcttttctc     1020
aaattaatat ttttctgcct caatggttca ggcccaatta tactagacta ctatcgcgac    1080
taaaataggg actagccgaa ttgatccggc ccagtatcag ttgtgtatca ccacgttatt    1140
tcaaatttca aactaaggga taaagatgtc atttgacata tgagatattt ttttgctcca    1200
ctgagatatt tttctttgtc ccaagataaa atatcttttc tcgcatcgtc gtcttttccat    1260
ttgcgcatta aaccaaaaag tgtcacgtga tatgtcccca accactacga atttaacta    1320
cagatttaac catggttaaa ccagaattca cgtaaaccga ctctaaacct agaaaatatc    1380
taaaccttgg ttaatatctc agccccctta taaataacga gacttcgtct acatcgttct    1440
acacatctca ctgctcacta ctctcactgt aatcccttag atcttctttt caaatttcac    1500
cattgcactg gatg                                                      1514
```

<210> SEQ ID NO 106
<211> LENGTH: 1954
<212> TYPE: DNA
<213> ORGANISM: Arabidopsis thaliana
<220> FEATURE:
<221> NAME/KEY: misc_feature
<222> LOCATION: (1)..(1954)
<223> OTHER INFORMATION: Ceres Promoter p326

<400> SEQUENCE: 106

```
gtgggtaaaa gtatccttct ttgtgcattt ggtattttta agcatgtaat aagaaaaacc      60
aaaatagacg gctggtattt aataaaagga gactaatgta tgtatagtat atgatttgtg     120
```

```
tggaatataa taaagttgta aaatatagat gtgaagcgag tatctatctt ttgactttca      180
aaggtgatcg atcgtgttct ttgtgatagt tttggtcgtc ggtctacaag tcaacaacca      240
ccttgaagtt ttcgcgtctc ggtttcctct tcgcatctgg tatccaatag catacatata      300
ccagtgcgga aaatggcgaa gactagtggg cttgaaccat aaggtttggc cccaatacgg      360
attccaaaca acaagcctag cgcagtcttt tgggatgcat aagactaaac tgtcgcagtg      420
atagacgtaa gatatatcga cttgattgga atcgtctaag ctaataagtt taccttgacc      480
gtttatagtt gcgtcaacgt ccttatggag attgatgccc atcaaataaa cctgaaaatc      540
catcaccatg accaccataa actcccttgc tgccgctgct ttggcttgag caaggtgttt      600
ccttgtaaag ctccgatctt tggataaagt gttccactt ttgcaagtag ctctgacccc       660
tctcagagat gtcaccggaa tcttagacag aacctcctct gccaaatcac ttggaagatc      720
ggacaatgtc atcattttg caggtaattt ctccttcgtt gctgctttgg cttgagcacg       780
gtgcttcttt gtaaagctcc gatctttgga taagagcgga tcggaatcct ctaggaggtg      840
ccagtccctt gacctattaa tttatagaag gttttagtgt attttgttcc aatttcttct      900
ctaacttaac aaataacaac tgcctcatag tcatgggctt caaattttat cgcttggtgt      960
atttcgttat ttgcaaggcc ttggcccatt ttgagcccaa taactaaatc tagccttttc     1020
agaccggaca tgaacttcgc atattggcgt aactgtgcag ttttaccttt ttcggatcag     1080
acaagatcag atttagacca cccaacaata gtcagtcata tttgacaacc taagctagcc     1140
gacactacta aaaagcaaac aaaagaagaa ttctatgttg tcattttacc ggtggcaagt     1200
ggacccttct ataaaagagt aaagagacag cctgtgtgtg tataatctct aattatgttc     1260
accgacacaa tcacacaaac ccttctctaa tcacacaact tcttcatgat ttacgacatt     1320
aattatcatt aactctttaa attcacttta catgctcaaa aatatctaat ttgcagcatt     1380
aatttgagta ccgataacta ttattataat cgtcgtgatt cgcaatcttc ttcattagat     1440
gctgtcaagt tgtactcgca cgcggtggtc cagtgaagca aatccaacgg tttaaaacct     1500
tcttacattt ctagatctaa tctgaaccgt cagatatcta gatctcattg tctgaacaca     1560
gttagatgaa actgggaatg aatctggacg aaattacgat cttacaccaa cccctcgac     1620 gagctcgtat atataaagct tatacgctcc tccttcacct tcgtactact actaccacca     1680
catttcttta gctcaacctt cattactaat ctccttttaa ggtatgttca cttttcttcg     1740
attcatactt tctcaagatt cctgcatttc tgtagaattt gaaccaagtg tcgattttg      1800 tttgagagaa gtgttgattt atagatctgg ttattgaatc tagattccaa tttttaattg     1860
attcgagttt gttatgtgtg tttatactac ttctcattga tcttgtttga tttctctgct     1920
ctgtattagg tttctttcgt gaatcagatc ggaa                                 1954
```

<210> SEQ ID NO 107
<211> LENGTH: 2016
<212> TYPE: DNA
<213> ORGANISM: Arabidopsis thaliana
<220> FEATURE:
<221> NAME/KEY: misc_feature
<222> LOCATION: (1)..(2016)
<223> OTHER INFORMATION: Ceres Promoter p32449

<400> SEQUENCE: 107

```
gatcggcctt cttcaggtct tctctgtagc tctgttactt ctatcacagt tatcgggtat       60
ttgagaaaaa agagttagct aaaatgaatt tctccatata atcatggttt actacaggtt      120
tacttgattc gcgttagctt tatctgcatc caaagttttt tccatgatgt tatgtcatat      180
```

| | | | | |
|---|---|---|---|---|
| gtgataccgt | tactatgttt | ataactttat | acagtctggt | tcactggagt ttctgtgatt | 240 |
| atgttgagta | catactcatt | catcctttgg | taactctcaa | gtttaggttg tttgaattgc | 300 |
| ctctgttgtg | atacttattg | tctattgcat | caatcttcta | atgcaccacc ctagactatt | 360 |
| tgaacaaaga | gctgtttcat | tcttaaacct | ctgtgtctcc | ttgctaaatg gtcatgcttt | 420 |
| aatgtcttca | cctgtctttc | tcttctatag | atatgtagtc | ttgctagata gttagttcta | 480 |
| cagctctctt | ttgtagtctt | gttagagagt | tagttgagat | attacctctt aaaagtatcc | 540 |
| ttgaacgctt | tccggttatg | accaatttgt | tgtagctcct | tgtaagtaga acttactggg | 600 |
| accagcgaga | cagtttatgt | gaatgttcat | gcttaagtgt | cgaacgtatc tatctctact | 660 |
| atagctctgt | agtcttgtta | gacagttagt | tttatatctc | cattttttg tagtcttgct | 720 |
| agttgagata | ttacctcttc | tcttcaaagt | atccttgaac | gctcaccggt tatgaaatct | 780 |
| ctacactata | gctctgtagt | cttgctagat | agttagttct | ttagctctct ttttgtagcc | 840 |
| tagttctta | gctctccttt | tgtagccttg | ctacagagta | agatgggata ttacctcctt | 900 |
| gaacgctctc | cggttatgac | caatttgttg | tagctccttg | taagtagaac ttaggataga | 960 |
| gtgagtcaac | tttaagaaag | aacctagtat | gtggcataac | cagattgcag gctctgtctc | 1020 |
| ggctacagta | acgtaactct | atagctcttt | gttttgttca | gaaagaacca gtgattggat | 1080 |
| gattcgtcct | tagaaactgg | acctaacaac | agtcattggc | tttgaaatca agccacaaca | 1140 |
| atgcctatat | gaaccgtcca | tttcatttat | ccgtttcaaa | ccagcccatt acatttcgtc | 1200 |
| ccattgataa | ccaaaagcgg | ttcaatcaga | ttatgtttta | attttaccaa attctttatg | 1260 |
| aagtttaaat | tatactcaca | ttaaaaggat | tattggataa | tgtaaaaatt ctgaacaatt | 1320 |
| actgattttg | gaaattaac | aaatattctt | tgaaatagaa | gaaaaagcct ttttcctttt | 1380 |
| gacaacaaca | tataaaatca | tactcccatt | aaaaagattt | taatgtaaaa ttctgaatat | 1440 |
| aagatatttt | ttacaacaac | aaccaaaaat | atttattttt | ttccttttt acagcaacaa | 1500 |
| gaaggaaaaa | cttttttttt | tgtcaagaaa | aggggagatt | atgtaaacag ataaaacagg | 1560 |
| gaaataact | aaccgaactc | tcttaattaa | catcttcaaa | taaggaaaat tatgatccgc | 1620 |
| atatttagga | agatcaatgc | attaaaacaa | cttgcacgtg | gaaagagaga ctatacgctc | 1680 |
| cacacaagtt | gcactaatgg | tacctctcac | aaaccaatca | aaatactgaa taatgccaac | 1740 |
| gtgtacaaat | tagggtttta | cctcacaacc | atcgaacatt | ctcgaaacat tttaaacagc | 1800 |
| ctggcgccat | agatctaaac | tctcatcgac | caattttga | ccgtccgatg gaaactctag | 1860 |
| cctcaaccca | aaactctata | taaagaaatc | ttttccttcg | ttattgctta ccaaatacaa | 1920 |
| accctagccg | ccttattcgt | cttcttcgtt | ctctagtttt | ttcctcagtc tctgttctta | 1980 |
| gatcccttgt | agtttccaaa | tcttccgata | aggcct | | 2016 |

<210> SEQ ID NO 108
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter PR0924

<400> SEQUENCE: 108

| | | | | |
|---|---|---|---|---|
| atctataacg | agttaacatg | ttgccagttt | gaatcaagaa | gcttggatga tgaatgaatg | 60 |
| gatcggtttg | tggtacaatt | cttaaaattg | tagtagagga | gacagagaaa aaacatgata | 120 |

```
agactttggt atttacaact tgacggagac aagacagtaa gccaaatctg tcacaaaaac      180
actcaaactc ttttctcagt gttttgagtt taaagagaga cttattcact tcccctttcg      240
taacacttat ttgtctccca accaaacagt ttctgtcctt tcccttgtcc tcccacgtgc      300
atctttatat ctcatgactt ttcgtttcta gatcttgaat aatgtcttag tggattaggt      360
ttgttgtcgg taaattaggt gaccgttttt ttcttatatt tggaagatcg cgggatgaag      420
cagatactga gtttcagggc atacacacct aatttgaaaa tcattgttag tccaatttca      480
ctttaatctt gtttacaaaa aaattgatct gaaaatgttg atgggataag taaaaatgta      540
agttttgcta gtagtcatga tataataata gcaaaaccag atcaattttg agcaaaagga      600
agaaacaaaa aacagatcga tcccacgagc aagactaagt gtaaagtggt tcccacaaga      660
gccatatgga tatggtcctt caacttttaa agcccattac ttcagtggtc gacccgacat      720
tacgccacga gtagtcacgc acgcacgact ccgttcacgt gacattcacg ttgatatttc      780
cccctctact ctcttctgct tggttgatct aaaaaacatg aagagaccaa cctaatttca      840
tattaatata tgatatagac ttcatactca acagtcactt tcgtaatcca aatccatatc      900
ttacgaaatt agttcttaat aaaggttgtg gattaagtta taatattgtg ttaagagtta      960
agacacagca tataaccttg taccaacagt gctttattct taaatggaaa caaaacatat     1020
gtca                                                                  1024
```

```
<210> SEQ ID NO 109
<211> LENGTH: 857
<212> TYPE: DNA
<213> ORGANISM: Arabidopsis thaliana
<220> FEATURE:
<221> NAME/KEY: misc_feature
<222> LOCATION: (1)..(857)
<223> OTHER INFORMATION: Ceres Promoter PD1367
<220> FEATURE:
<221> NAME/KEY: misc_feature
<222> LOCATION: (116)..(116)
<223> OTHER INFORMATION: n is a, c, t, g, unknown, or other
<220> FEATURE:
<221> NAME/KEY: misc_feature
<222> LOCATION: (136)..(136)
<223> OTHER INFORMATION: n is a, c, t, g, unknown, or other
<220> FEATURE:
<221> NAME/KEY: misc_feature
<222> LOCATION: (154)..(154)
<223> OTHER INFORMATION: n is a, c, t, g, unknown, or other
<220> FEATURE:
<221> NAME/KEY: misc_feature
<222> LOCATION: (159)..(159)
<223> OTHER INFORMATION: n is a, c, t, g, unknown, or other
<220> FEATURE:
<221> NAME/KEY: misc_feature
<222> LOCATION: (168)..(168)
<223> OTHER INFORMATION: n is a, c, t, g, unknown, or other
<220> FEATURE:
<221> NAME/KEY: misc_feature
<222> LOCATION: (172)..(172)
<223> OTHER INFORMATION: n is a, c, t, g, unknown, or other
<220> FEATURE:
<221> NAME/KEY: misc_feature
<222> LOCATION: (175)..(175)
<223> OTHER INFORMATION: n is a, c, t, g, unknown, or other
<220> FEATURE:
<221> NAME/KEY: misc_feature
<222> LOCATION: (679)..(679)
<223> OTHER INFORMATION: n is a, c, t, g, unknown, or other
<220> FEATURE:
<221> NAME/KEY: misc_feature
<222> LOCATION: (680)..(680)
<223> OTHER INFORMATION: n is a, c, t, g, unknown, or other
<220> FEATURE:
<221> NAME/KEY: misc_feature
```

-continued

```
<222> LOCATION: (686)..(686)
<223> OTHER INFORMATION: n is a, c, t, g, unknown, or other
<220> FEATURE:
<221> NAME/KEY: misc_feature
<222> LOCATION: (724)..(724)
<223> OTHER INFORMATION: n is a, c, t, g, unknown, or other
<220> FEATURE:
<221> NAME/KEY: misc_feature
<222> LOCATION: (737)..(737)
<223> OTHER INFORMATION: n is a, c, t, g, unknown, or other

<400> SEQUENCE: 109
ttggaattaa ttctgcggcc atggggctgc aggaattcga tggcccgatc ggccacagtt      60
ttcttttctc atcttacaac aagtttccag gaggatagag acataaacga agctcnggat     120
tgtatcgttc tttttnagct tttattcaca tccngaaang tcctgtangt tntangattc     180
tgttatcttg cggttttgag ttaatcagaa acagagtaat caatgtaatg ttgcaggcta     240
gatctttcat ctttggaaat ttgttttttt ctcatgcaat ttctttagct tgaccatgag     300
tgactaaaag atcaatcagt agcaatgatt tgatttggct aagagacatt tgtccacttg     360
gcatcttgat ttggatggtt acaacttgca agacccaatt ggatacttgc tatgacaact     420
ccaactcaag agtgtcgtgt aactaagaac cttgactaat ttgtaatttc aatcccaagt     480
catgttacta tatgttttt tgtttgtatt atttctctc ctacaattaa gctctttgac      540
gtacgtaatc tccggaacca actcctatat ccaccattta ctccacgttg tctccaatta     600
ttggacgttg aaacttgaca caacgtaaac gtatctacgt ggttgattgt atgtacatat     660
gtacaaacgt acacctttnn ctcctncttt cacttcatca cttggcttgt gaattcatta     720
attncctgcg aaggccntgc agggccatca ccactgcagt ggaacaatga agactaatct     780
ttttctcttt ctcatctttt cacttctcct atcattatcc tcggccgaat tcagtaaagg     840
agaagaactt ttcactg                                                   857
```